US005097013A

United States Patent [19]

Osawa et al.

[11] Patent Number: 5,097,013

[45] Date of Patent: Mar. 17, 1992

[54] NOVEL PEPTIDES POSSESSING A MACROPHAGE CHEMOTACTIC ACTIVITY

[75] Inventors: Toshiaki Osawa, Tokyo; Naonobu Yoshizuka, Tochigi; Masaaki Yoshimura, Tochigi; Eisaku Yoshida, Tochigi, all of Japan

[73] Assignee: KAO Corporation, Tokyo, Japan

[21] Appl. No.: 379,025

[22] Filed: Jul. 12, 1989

[30] Foreign Application Priority Data

Jul. 14, 1988 [JP] Japan ................................ 63-173785
Jun. 22, 1989 [JP] Japan ................................ 1-158432

[51] Int. Cl.[5] ........................ A61K 37/02; C07K 7/06

[52] U.S. Cl. ........................................ 530/328; 514/15; 514/16; 435/70.2

[58] Field of Search ........................ 435/70.2; 530/328; 514/15, 16

[56] References Cited

U.S. PATENT DOCUMENTS 3,888,837 6/1975 Tsumita et al. .
4,579,840 1/1986 Hahn .
4,675,295 6/1987 Osawa et al. ...................... 435/70.2

FOREIGN PATENT DOCUMENTS 8601211 2/1986 PCT Int'l Appl. .

OTHER PUBLICATIONS

Osawa et al., "Macrophage Chemotactic Factor (MCF) Produced by a Human T Cell Hybridoma Clone, Cellular Immunology", 123, pp. 212-225.

*Primary Examiner*—Lester L. Lee
*Assistant Examiner*—S. G. Marshall
*Attorney, Agent, or Firm*—Browdy and Neimark

[57] ABSTRACT

The present invention relates to physiologically active peptides and more particularly, to novel peptides having a specific amino acid sequence which possess a macrophage chemotactic activity.

2 Claims, 63 Drawing Sheets

SEPARATION OF M C F BY ANIONIC EXCHANGER ON DEAE SEPHADEX A25 COLUMN
+0.2M NaCl
+0.5M NaCl
MACROPHAGE CHEMOTACTIC ACTIVITY
10
5
20
40
60
80
CONDUCTIVITY (---)
NUMBER OF FRACTION (2.0 ml/tube)

SEPARATION OF MCF BY CATIONIC EXCHANGER ON MONO S COLUMN

SEPARATION OF MCF BY REVERSED PHASE COLUMN 0
1
2
3
4
5
6
7
8
9
10
PPM

NOVEL PEPTIDES POSSESSING A MACROPHAGE CHEMOTACTIC ACTIVITY

FIELD OF THE INVENTION

The present invention relates to physiologically active peptides and more particularly, to novel peptides having a macrophage chemotactic activity.

PRIOR ART AND ITS PROBLEMS

In general, a macrophage chemotactic factor (hereinafter simply referred to as "MCF") is known to be a lymphokine secreted from lymphocytes or lymphocytic cell lines. It is already known that after stimulating, for example, peripheral blood lymphocytes (hereinafter merely referred to as "PBL") with lectin, e.g., phytohemagglutinin (hereinafter merely referred to as "PHA"), a high macrophage chemotactic activity is recognized in the supernatant obtained by culturing the stimulated lymphocytes.

Macrophage chemotactic activity is also recognized in the culture supernatant of hybridoma obtained by fusing leukemia cells and the stimulated lymphocytes for purposes of rendering its life permanent (Japanese Unexamined Patent Application Laid-Open No. 60-181018).

On the other hand, when an elicit respondent is caused on a sensitized animal with delayed-type hypersensitivity, infiltration of both lymphocyte and macrophage into the tissue is remarkable after about 48 hours when skin reaction reaches the maximum. It is thus considered that MCF would take part in delayed-type hypersensitivity.

As described above, since MCF is defined to have an activity of collecting macrophage in the inflamed lesion, it is expected to apply MCF to drugs as antitumor agents.

However, a concentration of MCF is still low either in the culture supernatant of lymphocyte or in the skin where an elicit respondent has been caused and its structure is not clarified yet.

MEANS FOR SOLVING THE PROBLEM

Figure 1:
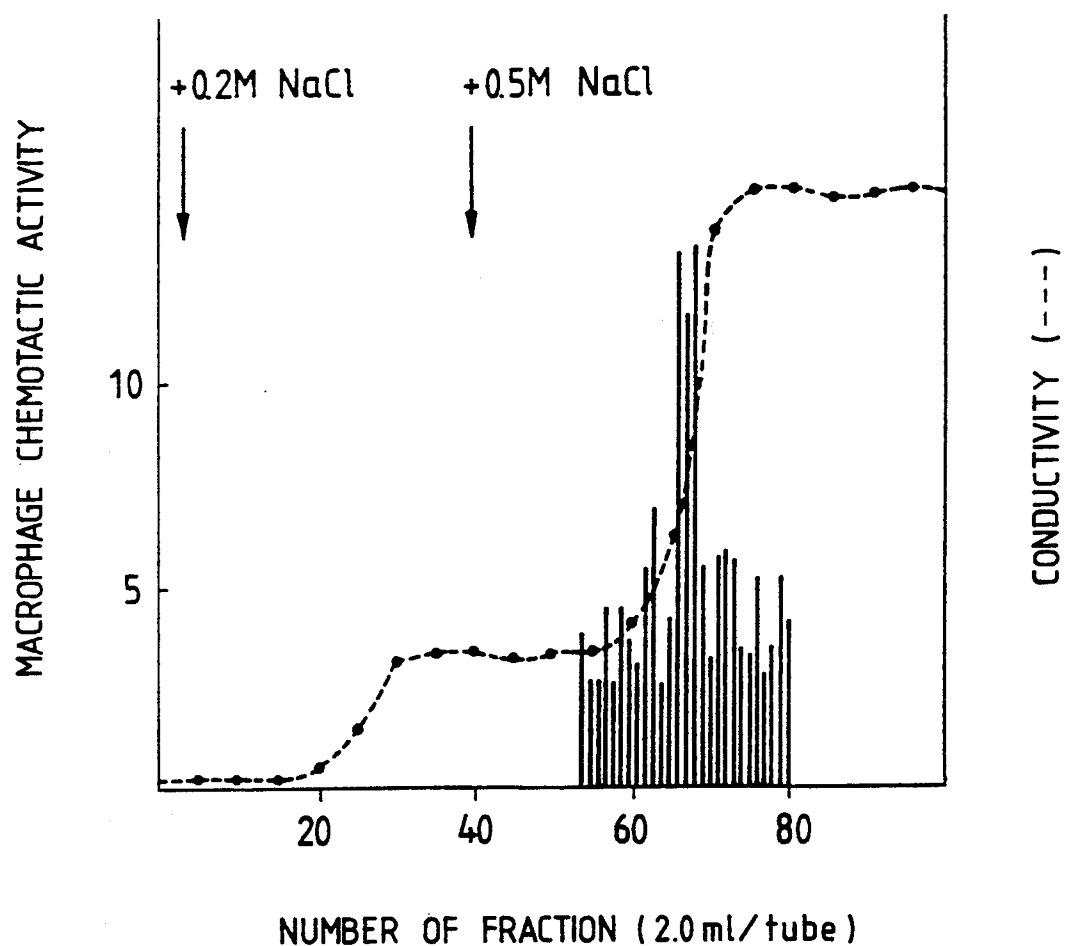
FIG. 1 shows separation of MCF with anionic exchanger DEAE-Sephadex A-25 in Example 2.

As a result of analyses of compounds having MCF activity, the present inventors have found that peptides having a specific amino acid sequence and derivatives thereof exert on high MCF activity and have reached the present invention.

That is, the present invention relates to a novel peptide in which amino acids are arranged through peptide bond in the order of:

Trp-Leu-Gly-Arg-Glu (or Gln)-Arg-Gly-Ser-Glu or
Arg-Leu-Gly-Arg-Glu (or Gln)-Asp-Gly-Ser-Glu and a novel peptide represented by general formula described below:

m-A-B-C-D-E-F-G-H-I-n wherein m is:
(a) hydrogen,
(b) H-Lys,
(c) Fmoc or
(d) L-Met;

A is:
(a) absent,
(b) L-Trp,
(c) L-Phe,
(d) D-Trp,
(e) L-Arg or
(f) L-Lys;

B is:
(a) absent,
(b) L-Leu,
(c) L-Ala,
(d) L-Pro,
(e) D-Leu,
(f) L-Ile,
(g) D-Nle,
(h) Gly or
(i) L-Val;

C is:
(a) absent,
(b) Gly or
(c) L-Ile;

D is:
(a) absent,
(b) L-Arg,
(c) L-Lys,
(d) D-Arg,
(e) L-Tyr,
(f) L-Asp,
(g) L-His or
(h) L-Gln;

E is:
(a) absent,
(b) L-Glu,
(c) L-Gln,
(d) D-Glu,
(e) Gly or
(f) L-Arg;

F is:
(a) absent,
(b) L-Asp,
(c) L-Asn,
(d) L-Glu,
(e) D-Asp or
(f) L-Ser;

G is:
(a) absent,
(b) Gly or
(c) L-Lys;

H is:
(a) absent,
(b) L-Ser,
(c) L-Cys,
(d) L-Ala,
(e) D-Ser or
(f) L-Leu;

I is:
(a) absent,
(b) L-Glu,
(c) L-Asp,
(d) L-Glu or
(e) L-Leu;

n is:

(a) hydroxy or
(b) amino group.

The novel peptide of the present invention has a high MCF activity and is effectively used as reagents for research of delayed-type hypersensitivity and further for drugs as antitumor agents.

The peptide of the present invention can be produced by (1) a biochemical method using a vital specimen or its culture or (2) chemical synthesis which comprises chemically binding amino acids in sequence.

(1) Biological Method using a Vital Specimen or its Culture a) Method using Human Peripheral Blood Lymphocyte There is a method using human peripheral blood lymphocytes (hereinafter simply referred to as PBL) as raw materials for producing the novel peptide of the present invention.

PBL can be obtained by using human peripheral blood and separating lymphocytes depending upon their specific gravity.

That is, peripheral blood is laid over a solution of a suitable specific gravity such as Histohypaque solution made by Sigma Inc., or Ficol or Percoll solution made by Pharmacia Fine Chemicals Inc., which is then centrifuged at, e.g., 1500 rpm, for 20 minutes to give a lymphocyte-rich fraction. The fraction is adhered to a plastic Petri dish and non-adhesive cells can be used as lymphocytes.

To produce the peptide of the present invention, PBL is suspended in medium conventionally used, for example, 10% fetal calf serum (FCS)-containing RPMI 1640 medium, lectin (concanavalin A, phytohemagglutinin, etc.) is supplemented to the suspension and the resulting mixture is cultured. Preferably, lymphocytes cultured for an appropriate time period, e.g., for 20 hours, etc. are cultured since a culturing efficiency is good.

In order to obtain the peptide of the present invention, PBL is resuspended in serum-free medium, the suspension is cultured in a conventional manner, for example, at 37° C. for an hour to several days in the presence of 5% $CO_2$ and the resulting supernatant is used.

PBL cells may also be broken as they are without performing resuspension of PBL in serum-free medium and the following incubation; centrifugation is performed to remove relatively large cell organs and the thus obtained supernatant (cell lysate) may also be used. In this case, it is sufficient to conduct centrifugation, e.g., at 10,000×g for about 20 minutes.

To collect the peptide of the present invention from the culture supernatant of PBL or cell lysate, the high molecular fraction is firstly removed by a method for separation depending upon molecular size such as ultrafiltration, etc. The solution is adsorbed to an anionic exchanger to increase a salt concentration, whereby the peptide can be eluted. As the anionic exchanger, there may be used DEAE (diethylaminoethyl exchanger), QAE (quaternary aminoethyl exchanger) and further Mono Q manufactured by Pharmacia Fine Chemicals, Inc., and the like.

Furthermore, the active fraction obtained herein may also be adsorbed to a cationic exchanger to increase a salt concentration, whereby the peptide can be eluted. As the cationic exchanger, there may be used Mono S manufactured by Pharmacia Fine Chemicals, Inc., carboxymethyl exchanger, and the like.

Moreover, the active fraction thus obtained may also be subjected to reversed phase chromatography to increase a concentration of an organic solvent usually such as acetonitrile, etc., whereby the peptide can be eluted and obtained in almost a pure form.

b) Method using Non-established Cell Line

As the raw material for producing the novel peptide of the present invention, established cells can be used. If an efficiency as the raw material is not taken into account, it is preferred to use a hybridoma of peripheral blood lymphocyte and leukemia cell line, since the peptide of the present invention can be efficiently produced.

To produce the peptide of the present invention using established cells, the procedures adopted for producing the peptide of the present invention using PBL apply without modification.

(2) Chemical Synthesis for Chemically Binding Amino Acids in Sequence

For chemical synthesis of peptide, solid phase synthesis has been widely used. This method can also apply to synthesis of the peptide of the present invention.

In the solid phase synthesis, by protecting reactive side chains on various amino acid moieties with an appropriate protective group, chemical reactions which might occur on reactive side chains can be prevented until the protective group is finally removed. As the side chain protective group of, for example, Asp and Glu, OBzl and OtBu can be used and as the side chain protective group for Ser, Thr and Tyr, Bzl, Br-Z and tBu can be used. As the further protective group, there may be used Cl-Z and Tos for Lys; Tos, MTS and Mtr for Arg; Tos, DNP and Trt.OH for His; CHO for Trp; and 4-MeBzl and 4-MeOBzl for Cys. Met can be protected in the form of sulfoxide.

As the solid phase synthesis, Boc method and Fmoc method are representative and both methods can be utilized for synthesis of the peptide of the present invention. According to the solid phase synthesis, synthesis can start from the C-end of peptide using, for example, an a-amino-protected amino acid. An appropriate starting material can be prepared by adding a necessary α-amino-protected amino acid to, for example, chloromethyl resin, oxymethyl resin or benzhydrylamine resin. 4-(oxymethyl)phenylacetamidomethyl resin, which α-amino acid, α-amino group and side chain groups are protected is commercially available and can also be used for synthesis of the peptide of the present invention. The peptide of the present invention can also be synthesized utilizing an automated solid phase synthesizer.

Typical steps for peptide synthesis according to the Boc method are shown below. As the starting material, for example, an amino acid resin which α-amino group is protected with Boc group is used.

1. washing with DCM (3 times)
2. removal of Boc with TFA/DCM
3. washing with DCM (3 times)
4. neutralization with DIEA/DMF
5. washing with DMF (5 times)
6. reaction with Boc amino acid anhydride
7. washing with DCM (5 times)
8. repetition of Steps 2 through 7
9. washing with DCM (twice)
10. drying with Ar gas
11. addition of anisole/methyl ethyl sulfide 12. addition of HF at −70° C. followed by reaction at −20° C. for 30 minutes and 0° C. for 30 minutes
13. removal of HF by distillation
14. washing with chloroform-ether (3 times)
15. extraction of synthesized peptide with 5N acetic acid aqueous solution
16. purification of synthesized peptide by HPLC Typical steps for peptide synthesis according to the Fmoc method are shown below. As the starting material, for example, an amino acid resin which α-amino group is protected with Boc group is used.

1. washing with DCM (3 times)
2. removal of Boc with TFA/DCM
3. washing with DCM (3 times)
4. washing with DMF (3 times)
5. reaction with Fmoc amino acid anhydride
6. washing with DMF (5 times)
7. removal of Fmoc with piperidine/DMF
8. repetition of Steps 4 through 7
9. washing with DMF (5 times)
10. washing with DCM (twice)
11. drying with Ar gas
12. addition of anisole/methyl ethyl sulfide/1,2-ethanedithiol
13. addition of HF at −70° C. followed by reaction at −20° C. for 30 minutes and 0° C. for 30 minutes
14. removal of HF by distillation
15. washing with chloroform-ether (3 times)
16. extraction of synthesized peptide with 5N acetic acid aqueous solution
17. purification of synthesized peptide by HPLC Hereafter the present invention is described in more detail by referring to the examples below. In case that amino acid, peptide, protective group, active group, etc. are indicated with symbols, ordinary symbols defined in IUPAC and IUP or used in the field of peptide chemistry are used. Examples of the symbols are as follows.

L-Ala . . . L-alanine
L-Arg . . . L-arginine
L-Asn . . . L-asparagine
L-Asp . . . L-aspartic acid
L-Cys . . . L-cystein
L-Gln . . . L-glutamine
L-Glu . . . L-glutamic acid
Gly . . . glycine
L-His . . . L-histidine
L-Ile . . . L-isoleucine
L-Leu . . . L-leucine
L-Lys . . . L-lysine
L-Met . . . L-methionine
L-Phe . . . L-phenylalanine
L-Pro . . . L-proline
L-Ser . . . L-serine
L-Thr . . . L-threonine
L-Trp . . . L-tryptophan
L-Tyr . . . L-tyrosine
L-Val . . . L-valine
D-Ala . . . D-alanine
D-Arg . . . D-arginine
D-Asn . . . D-asparagine
D-Asp . . . D-aspartic acid
D-Cys . . . D-cystein
D-Gln . . . D-glutamine
D-Glu . . . D-glutamic acid
D-His . . . D-histidine
D-Ile . . . D-isoleucine
D-Leu . . . D-leucine
D-Lys . . . D-lysine
D-Met . . . D-methionine
D-Nle . . . D-norleucine
D-Phe . . . D-phenylalanine
D-Pro . . . D-proline
D-Ser . . . D-serine
D-Thr . . . D-threonine
D-Trp . . . D-tryptophan
D-Tyr . . . D-tyrosine
D-Val . . . D-valine
HPLC . . . high performance liquid chromatography
ODS column . . . C18 column
HMP resin . . . hydroxymethylphenoxyacetic acid resin
PAM resin . . . phenylacetamide resin
BHA resin . . . benzhydrylamine resin
DCM . . . dichloromethane
DMF . . . dimethylformamide
TFA . . . trifluoroacetic acid
Ar gas . . . argon gas
Bzl . . . benzyl group
tBu . . . t-butyl group
Z . . . benzyloxycarbonyl group
Boc . . . butyloxycarbonyl group
Tos . . . tosyl group
MTS . . . mesitylene-2-sulfonyl group
Trt . . . trityl group
DNP . . . 2,4-dinitrophenyl group
Mtr . . . 4-methoxy-2,3,6-trimethylbenzenesulfonyl group
Fmoc . . . 9-fluorenylmethoxycarbonyl group Hereafter the present invention is described in more detail with reference to the examples below.

Macrophage chemotactic activity in the examples was determined as follows.

Peritoneal exudate cells (usually more than 95% were macrophage) collected from guinea pig in which liquid paraffin had previously been peritoneally injected 3 or 4 days before were used as macrophage in a cell concentration of $2\times10^6$/ml.

A sample which activity was to be determined was charged in lower wells of a 48 well chemotaxis chamber and a polycarbonate membrane having a pore size of 5 μm was put thereon, and the macrophage suspension was charged in upper wells followed by incubation at 37° C. for 90 minutes in a $CO_2$ incubator. After the incubation, adherent cells on the non-chemotactic surface was removed, fixed and subjected to Giemsa staining and then to inclusion treatment. Then, the cells on the chemotactic surface were microscopically (×400) counted and the cell count was made MCF activity.

In the present invention, MCF-A51 strain was used as established cells, which production is given below.

Production of Human T Cell Hybridoma

It is known that T cells produce a variety of lymphokines considered to exert on various physiological activities, in addition to the factor for regulating the immune system. In recent years, attempts to produce a hybridoma have been made using cell fusion technique. Among them, for production of human T cell hybridoma, the emetin-actinomycin method (J. Immunology, 128, 2714 (1982)) developed by Kobayashi et al. is known to provide hybridoma with a high fusion efficiency in high frequency.

Human acute T cell leukemia cell line CEM-11 which is the parent of human T cell hybridoma MCF-A51 strain was publicly reported by Kobayashi, Y. et al. (J.

Immunology, 128, 2714 1982) and Higuchi, M. et al. (Cell Immunol., 78, 257, 1983) and is accessible.

MCF-A51 strain was produced by fusion of human acute T cell leukemia cell line CEM-11 and human peripheral blood lymphocyte stimulated with phytohemagglutinin (PHA) by the emetin-actinomycin method. The fused strain was confirmed by determining its macrophage chemotactic activity (supra) of the culture broth.

PBL was cultured in RPMI 1640 medium (containing 10% FCS (fetal calf serum)) at 37° C. in a 5% $CO_2$ incubator for 2 days in the presence of PHA-P (manufactured by Smiles Inc.) (10 μg/ml). The cells were dispersed in 0.1M lactose solution. The dispersion was stored at 37° C. for 30 minutes and centrifuged (1000 rpm, 5 minutes) to remove cell aggregation with PHA-P. The thus prepared peripheral blood lymphocyte was used for fusion.

On the other hand, human acute T cell leukemia cell line CEM-11 was dispersed in RPMI 1640 (serum free). The dispersion was stored at 37° C. for 2 hours in the presence of $5\times10^{-5}$M of emetin and 0.25 μg/ml of act with phosphated isotonic buffer (PBS) 3 times. The cells and the peripheral blood lymphocyte described above were mixed in a ratio of 1 : 10 to prepare loose pellets. 45% Polyethylene glycol 4000 and a solution of 5 μg/ml of poly-L-arginine were gradually added to the pellets to cause fusion. After centrifugation (800 rpm, 4 minutes), the supernatant was thoroughly removed and the precipitates were dispersed in RPMI 1640 (10% FCS, 2 mM glutamine, $5\times10^{-5}$M 2-mercaptoethanol) in a concentration of $1\times10^{9}$/ml and 0.1 ml of the resulting dispersion was charged in a 96 well flat microplate. Further as a feeder cell, 0.1 ml of mitomycin C-treated (5 μg/ml) cell line CEM-5 was added in a concentration of $4\times10^{5}$/ml. The plate was cultured at 37° C. under the condition of 5% $CO_2$. After then, the culture solution was exchanged every other day. About 2 weeks after, hybridoma was obtained.

In order to collect the macrophage chemotactic factor as a monoclonal factor, a hybridoma having a high macrophage chemotactic activity was cloned by limiting dilution. That is, using a 96 well flat microplate, a hybridoma dispersion diluted to 0.5/well was inoculated onto each well. Mitomycin C-treated cell line CEM-1 was added as a feeder cell and allowed to stand at 37° C. for 2 weeks under the condition of 5% $CO_2$ to obtain 39 clones.

With respect to the culture supernatant of these hybridoma clones, macrophage chemotactic activity was determined by the method described above and a hybridoma clone showing a high macrophage chemotactic activity was used as MCF-A51 strain.

EXAMPLE 1

Human T cell hybridoma MCF-A51 strain was dispersed in Hanks' medium in $5\times10^{5}$/ml. The dispersion was incubated at 37° C. for 90 minutes in the presence of 5% $CO_2$. The culture broth was centrifuged (1000 rpm ×5 minutes) to give the culture supernatant. The supernatant was passed through ultrafiltration membrane UM10 manufactured by Amicon Company and the filtrate was passed through Sephadex A-25 column which had been previously equilibrated with 5 mM HEPES (N-2-hydroxyethyl-piperazine-N'-2-ethanesulfonic acid), pH 8.0 (Buffer A). The column was then thoroughly washed with Buffer A. When stepwise eluted with Buffer A containing 0.2M sodium chloride and with Buffer A containing 0.5M sodium chloride, macrophage chemotactic activity was found in the fraction eluted with 0.5M sodium chloride The fraction was passed through Mono S (manufactured by Pharmacia Fine Chemicals, Inc.) column which had been previously equilibrated with 10 mM HEPES, pH 7.2 (Buffer B). After thoroughly washing with Buffer B, elution was carried out by linear density gradation method using sodium chloride up to 2M of its concentration, whereby the activity was eluted in the fraction near about 1M.

Further, the fraction was applied to reversed phase column ODS-120T (manufactured by Toso Co., Ltd.) which had been equilibrated with 1 mM acetate buffer, pH 5.7. After thoroughly washing, elution was carried out by linearly increasing the concentration of acetonitrile. The state of eluting the peptide was monitored by absorbancy of 215 nm and the activity of the obtained peak was determined, whereby the activity was found in the peak at the elution site of about 25% acetonitrile. The fraction was used as purified MCF.

EXAMPLE 2

After the same A51 strain as used in Example 1 was washed with Hanks' medium, the cells were homogenized by means of high pressure nitrogen gas cell homogenization and then centrifuged (10,000× g, 20 minutes). The obtained supernatant was further centrifuged at 150,000×g for 27 hours to separate into the supernatant and pellets. The precipitate fraction was suspended in 5 mM HEPES, pH 8.0 (Buffer A). After ultrasonic treatment, centrifugation was again performed at 60,000× g for an hour to give the supernatant. After the supernatant was filtered through ultrafiltration membrane UM10 (manufactured by Amicon Company), the filtrate was applied to Sephadex A-25 column which had been previously equilibrated with Buffer A. After the column was thoroughly washed with Buffer A, stepwise elution was effected using Buffer A containing 0.2M sodium chloride and with Buffer A containing 0.5M sodium chloride, whereby macrophage chemotactic activity was found in the fraction eluted with 0.5M sodium chloride. The results are shown in FIG. 1.

Figure 2:
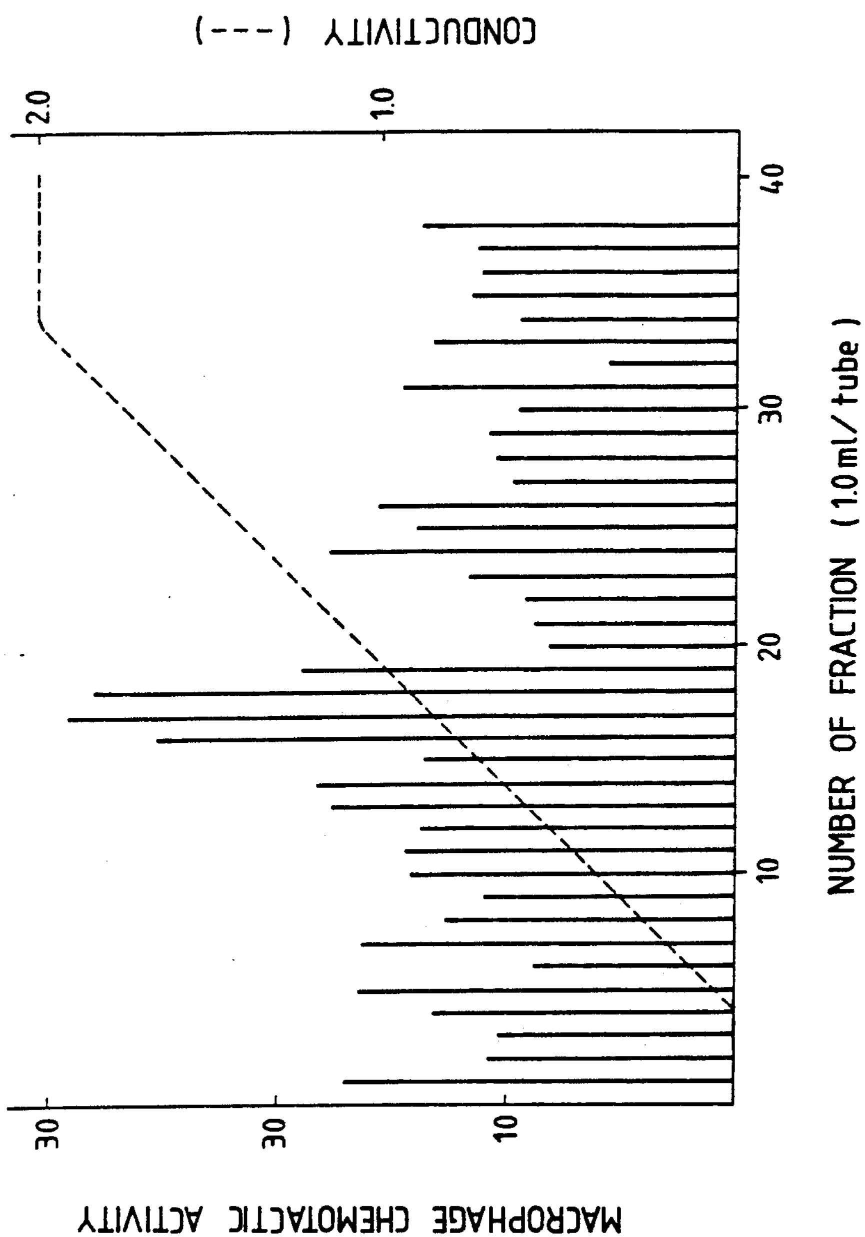
FIG. 2 shows separation of condensed MCF fraction through cationic exchanger Mono S column.

The fraction was further applied to Mono S (manufactured by Pharmacia Fine Chemicals, Inc.) column which had been previously equilibrated with 10 mM HEPES, pH 7.2 (Buffer B). After thoroughly washing with Buffer B, elution was carried out by the linear density gradation method using sodium chloride up to 2M of its concentration, whereby the activity was eluted in the fraction near about 1M. The results are shown in FIG. 2.

Figure 3:
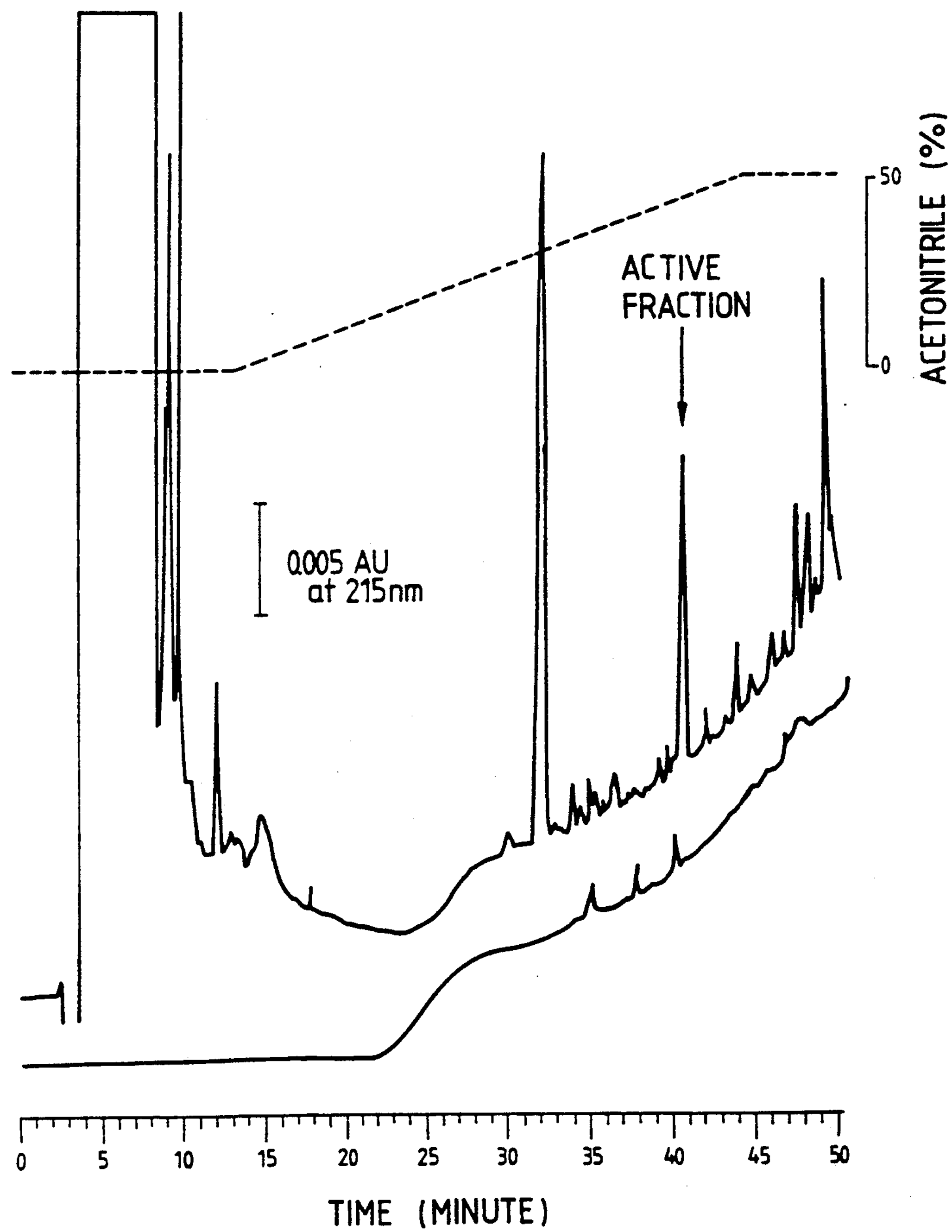
FIG. 3 shows separation of further condensed MCF fraction through reversed phase column.
Figure 4:
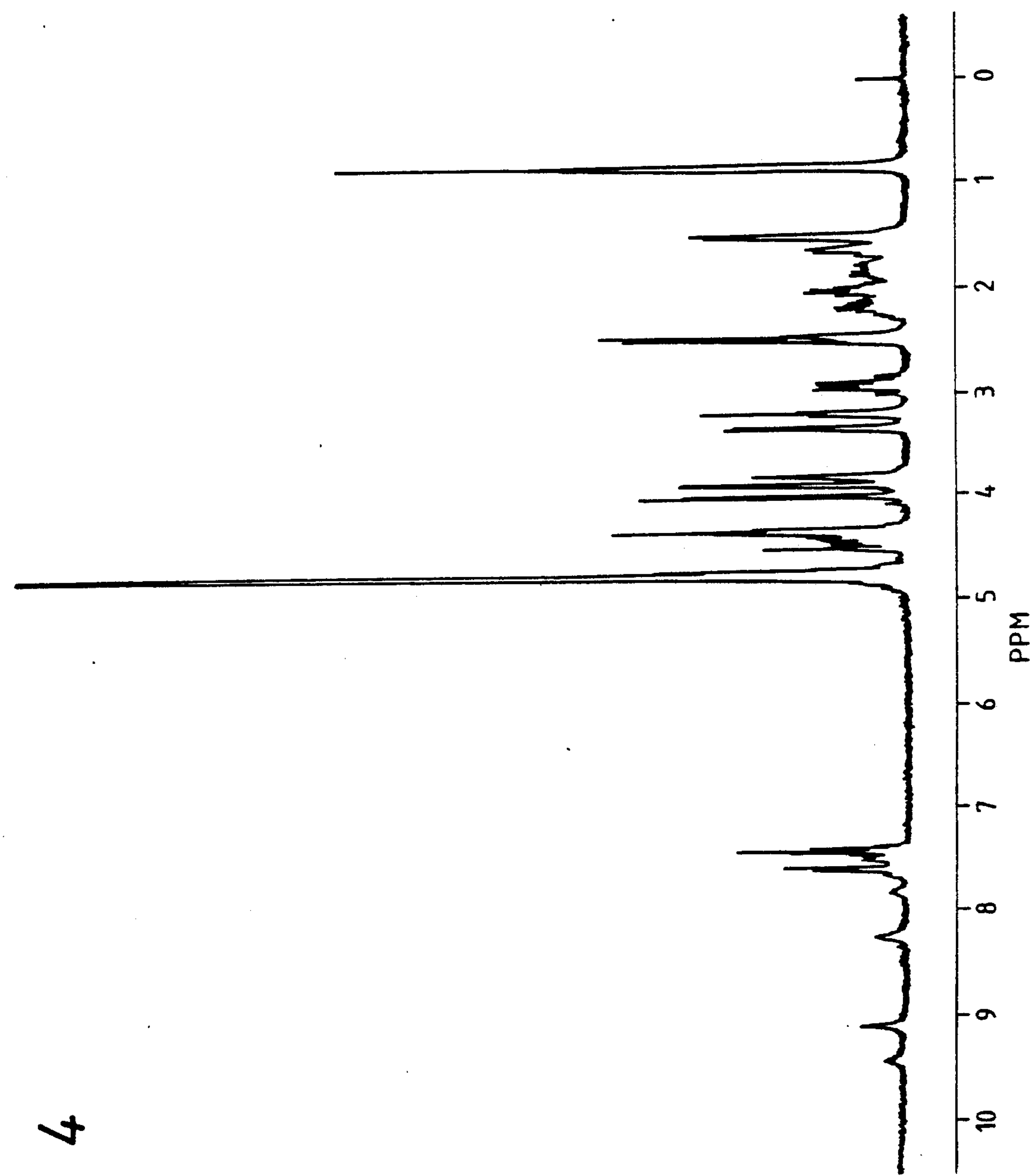
FIGS. 4 through 63 are charts for N.M.R. of each of Compound Nos. 1 through 60 shown in Table 2.
Figure 5:
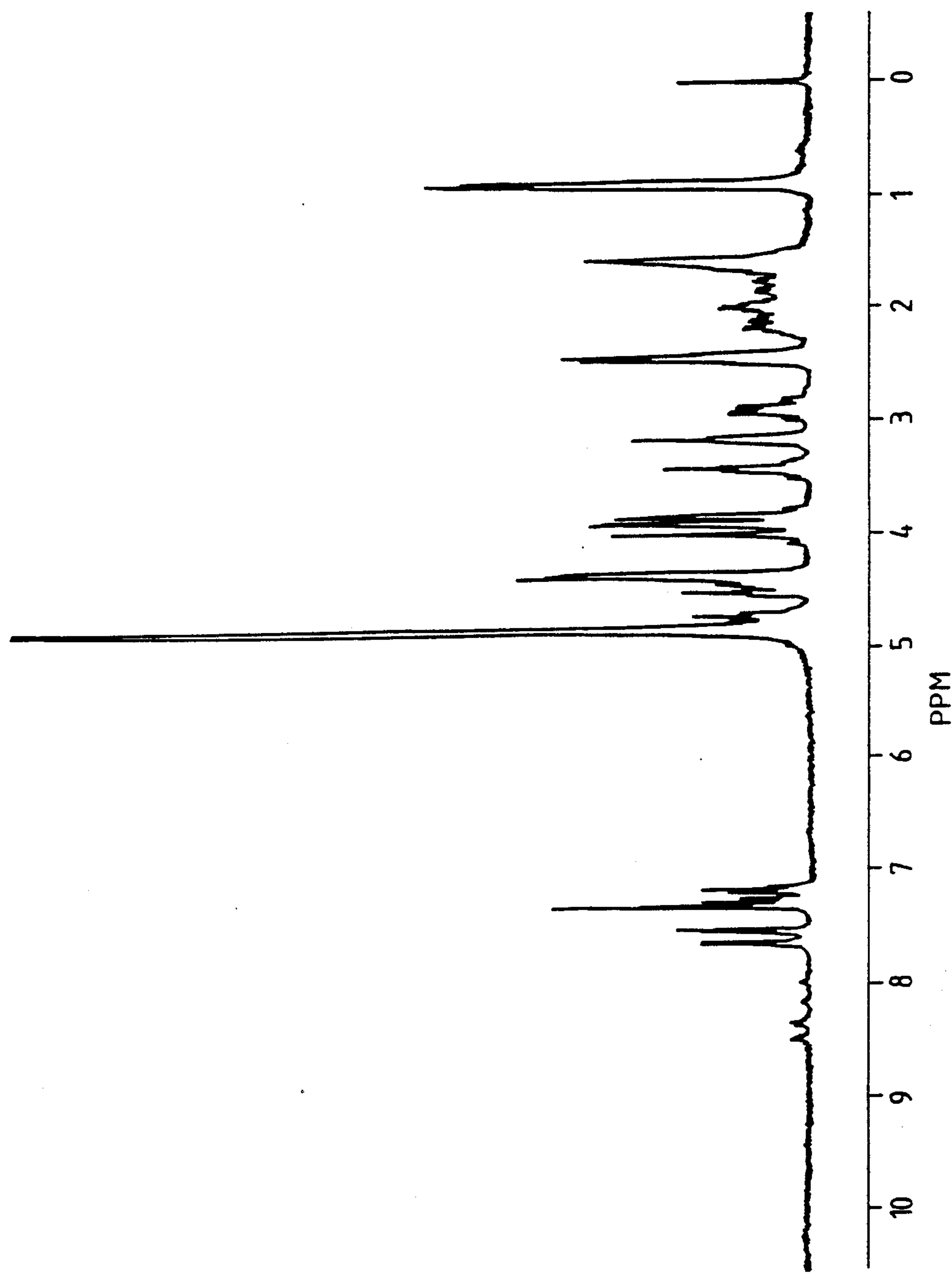
Figure 6:
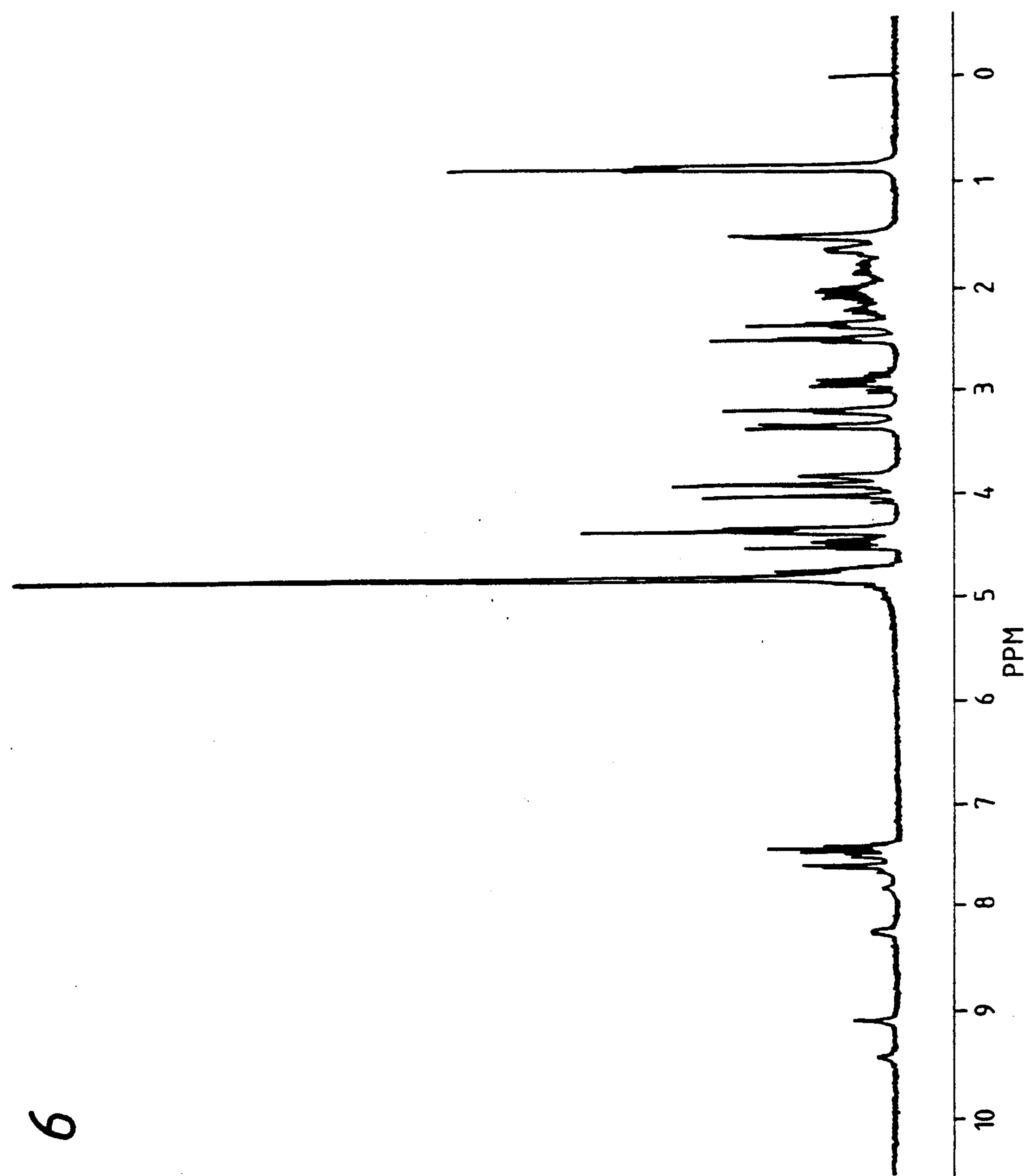
Figure 7:
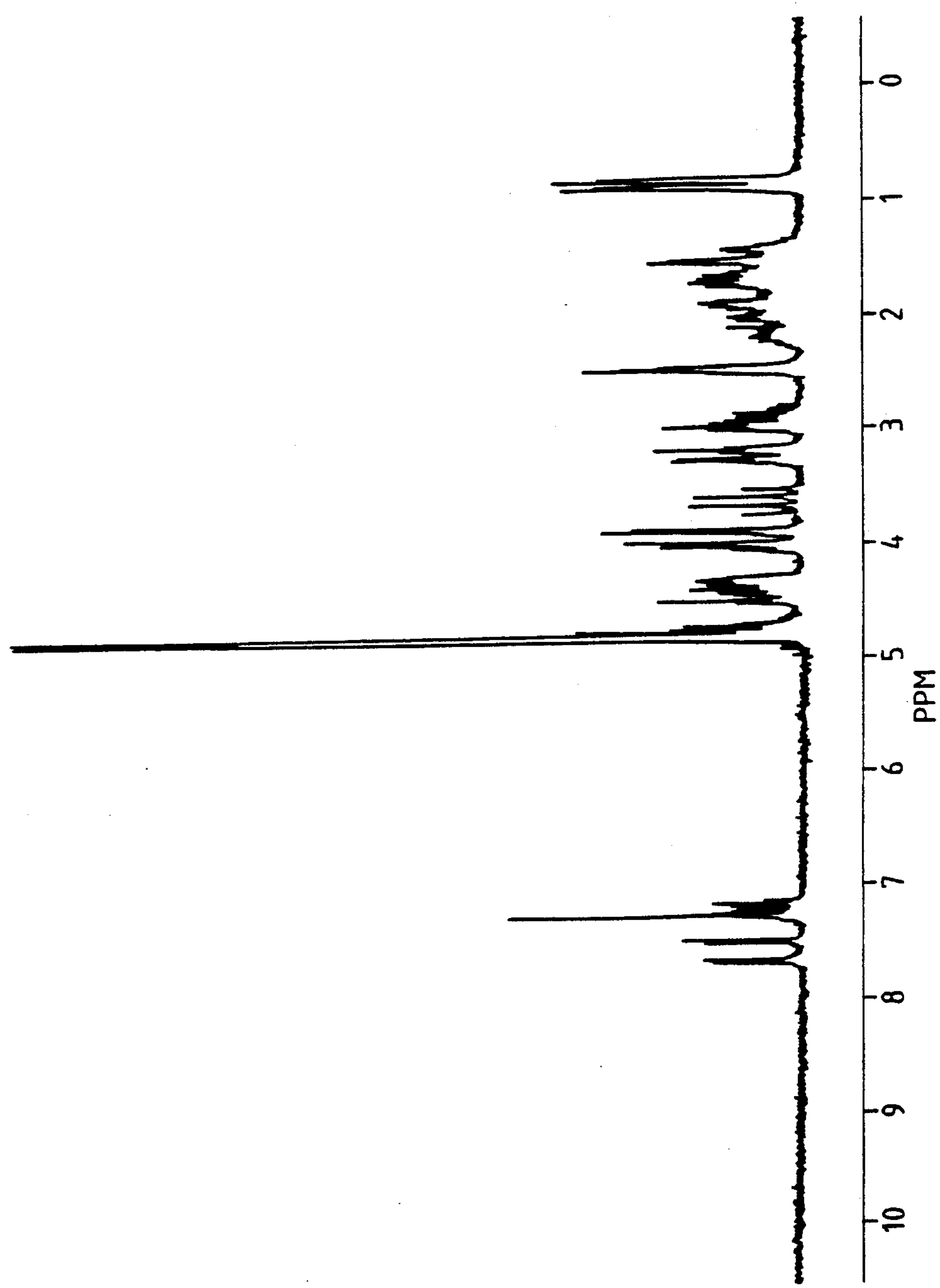
Figure 8:
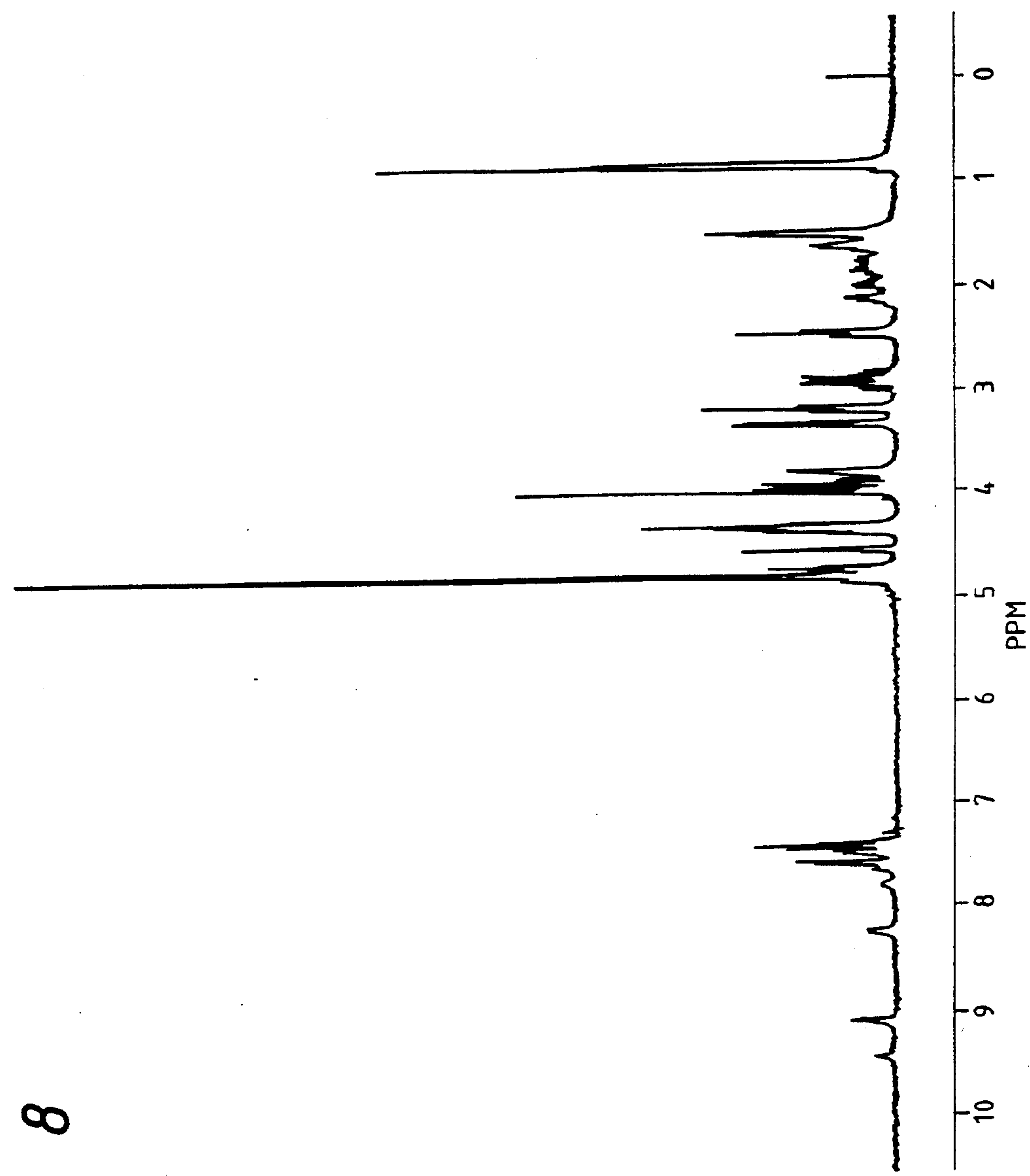
Figure 9:
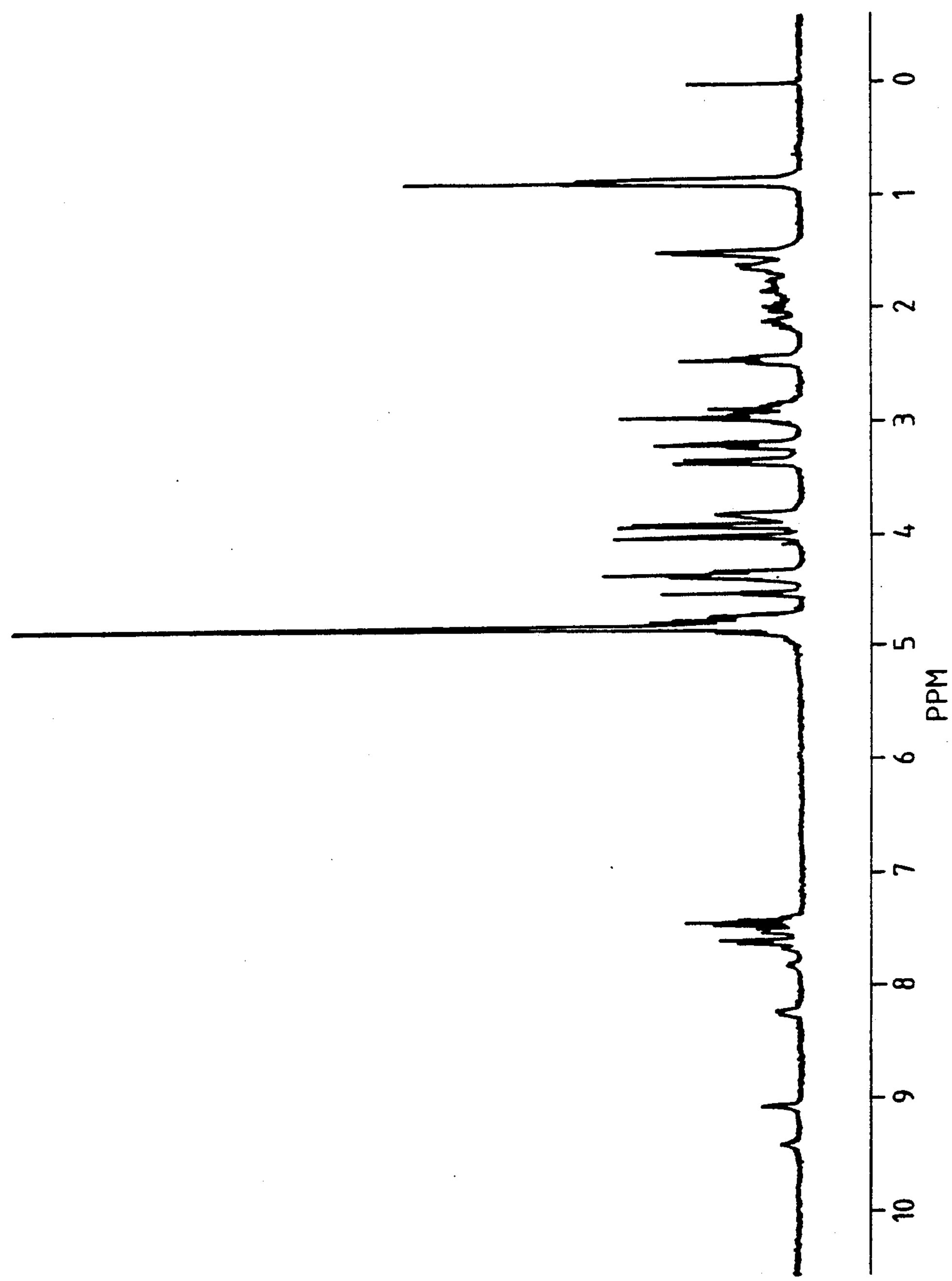
Figure 10:
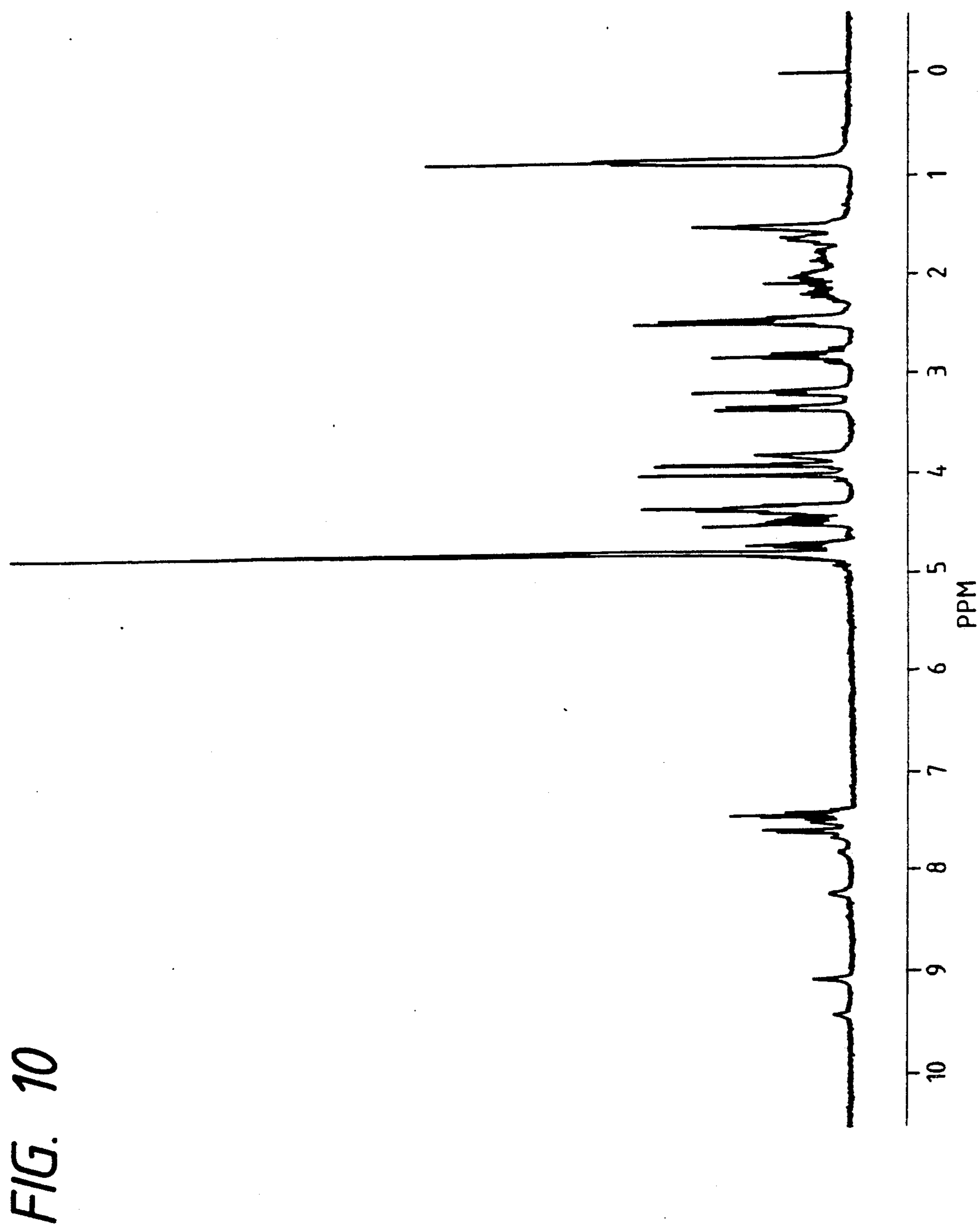
Figure 11:
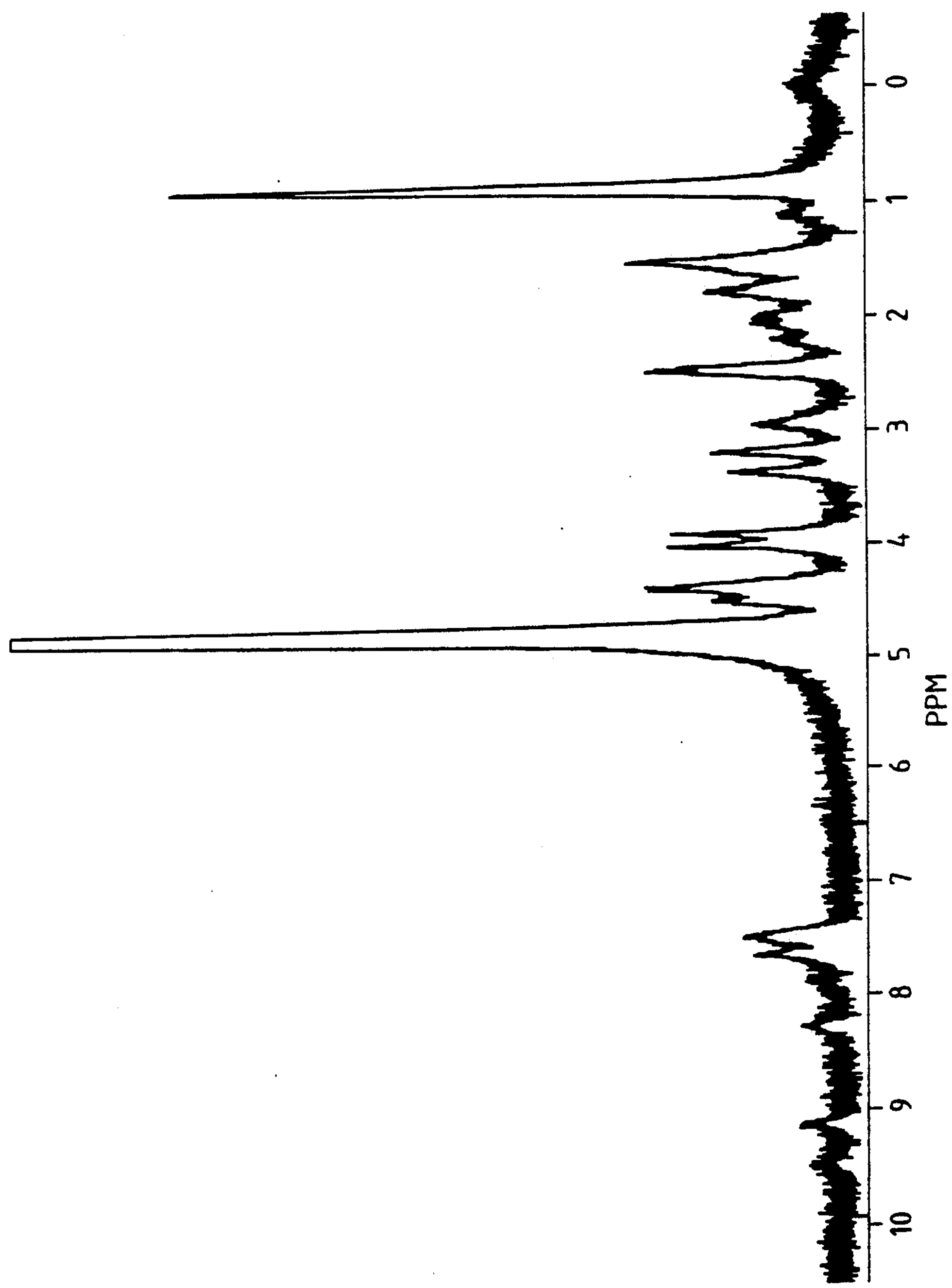
Figure 12:
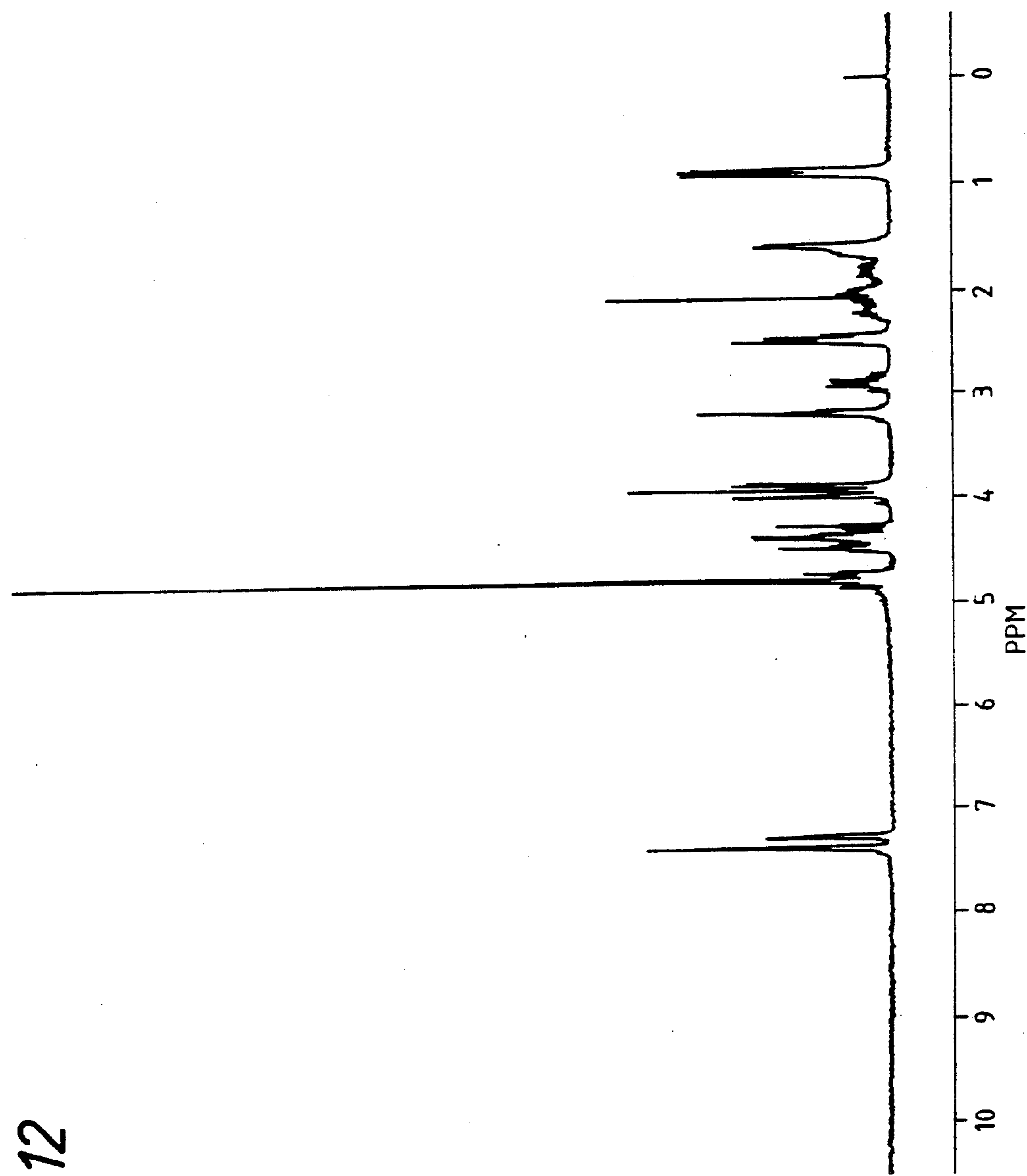
Figure 13:
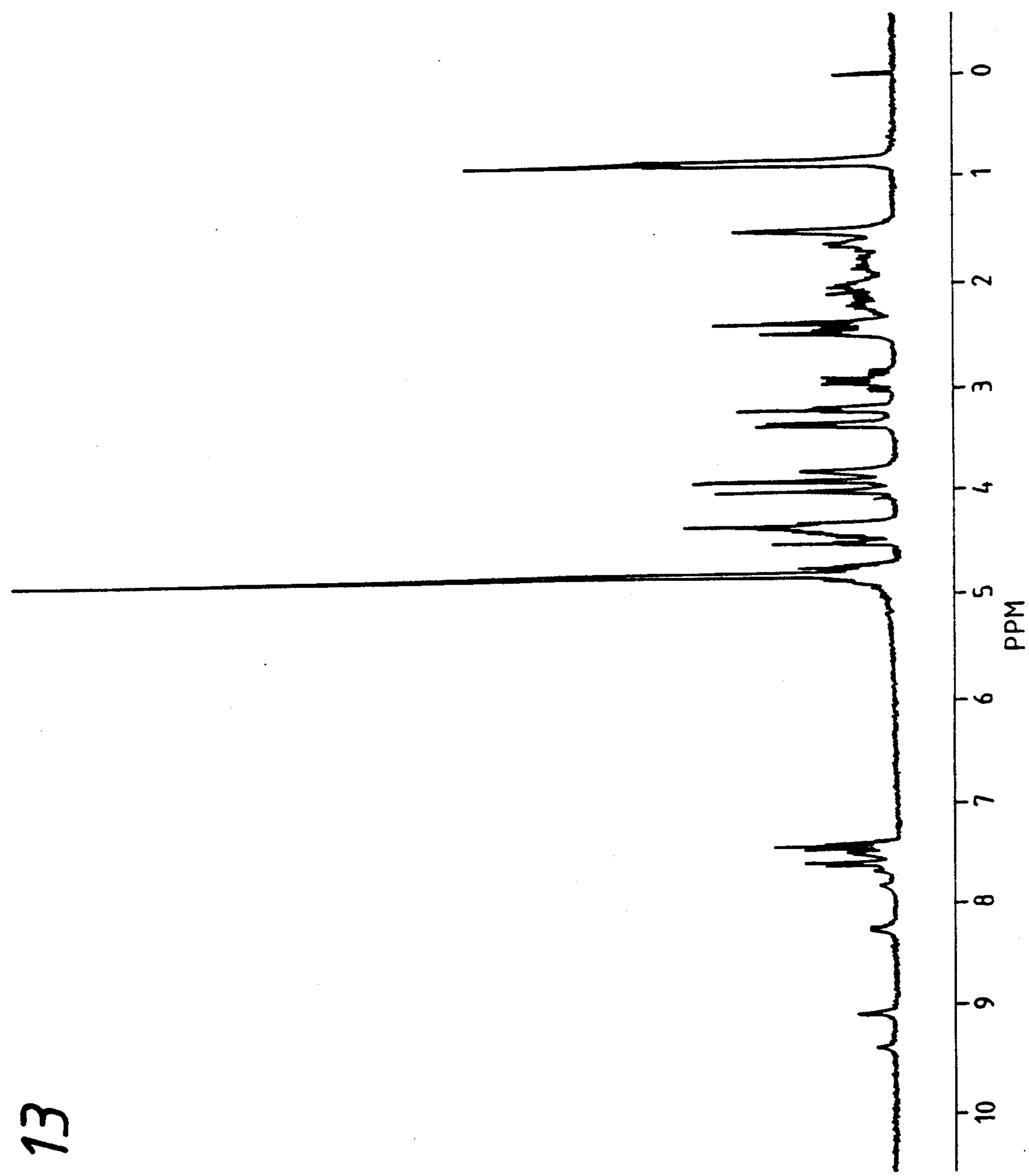
Figure 14:
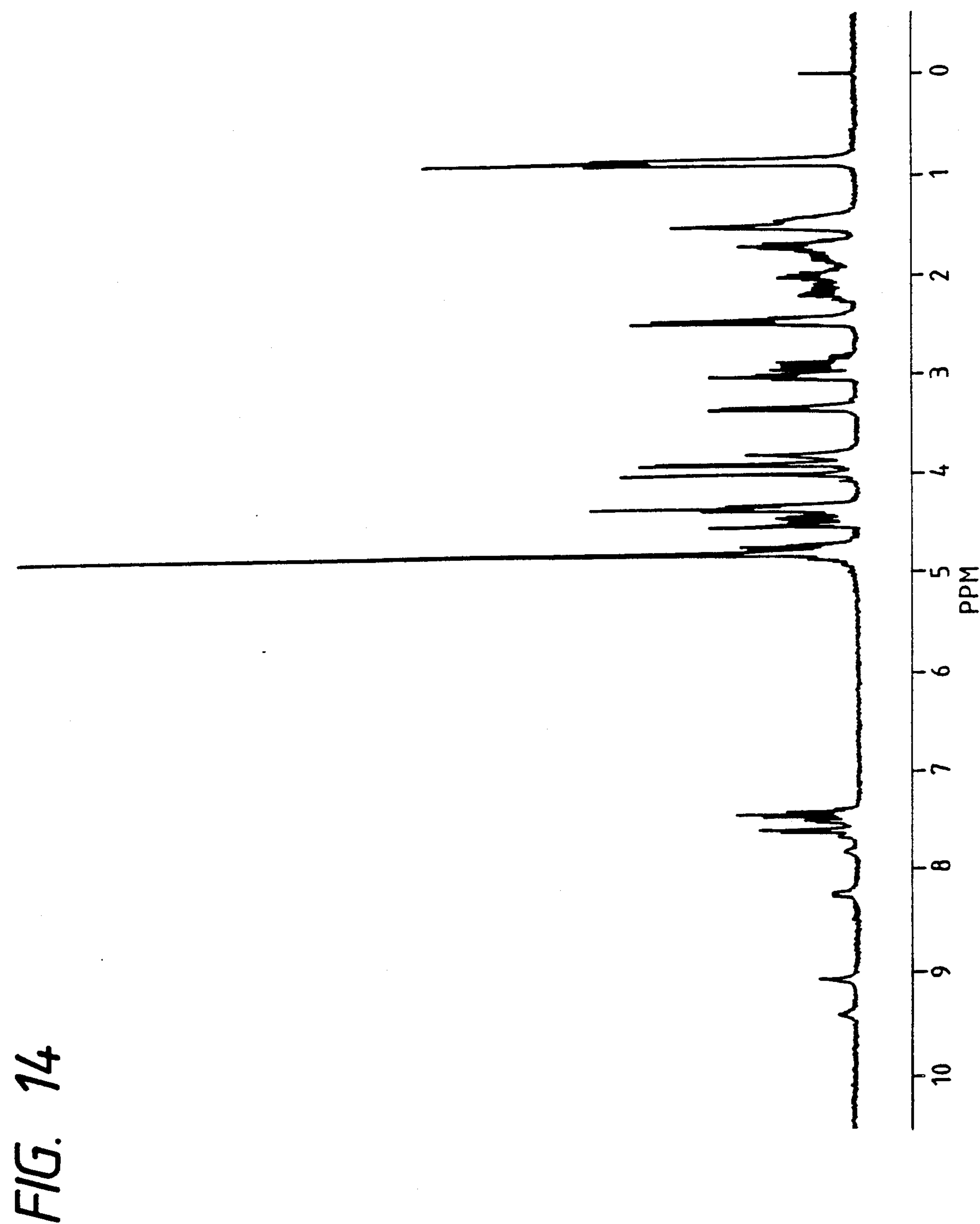
Figure 15:
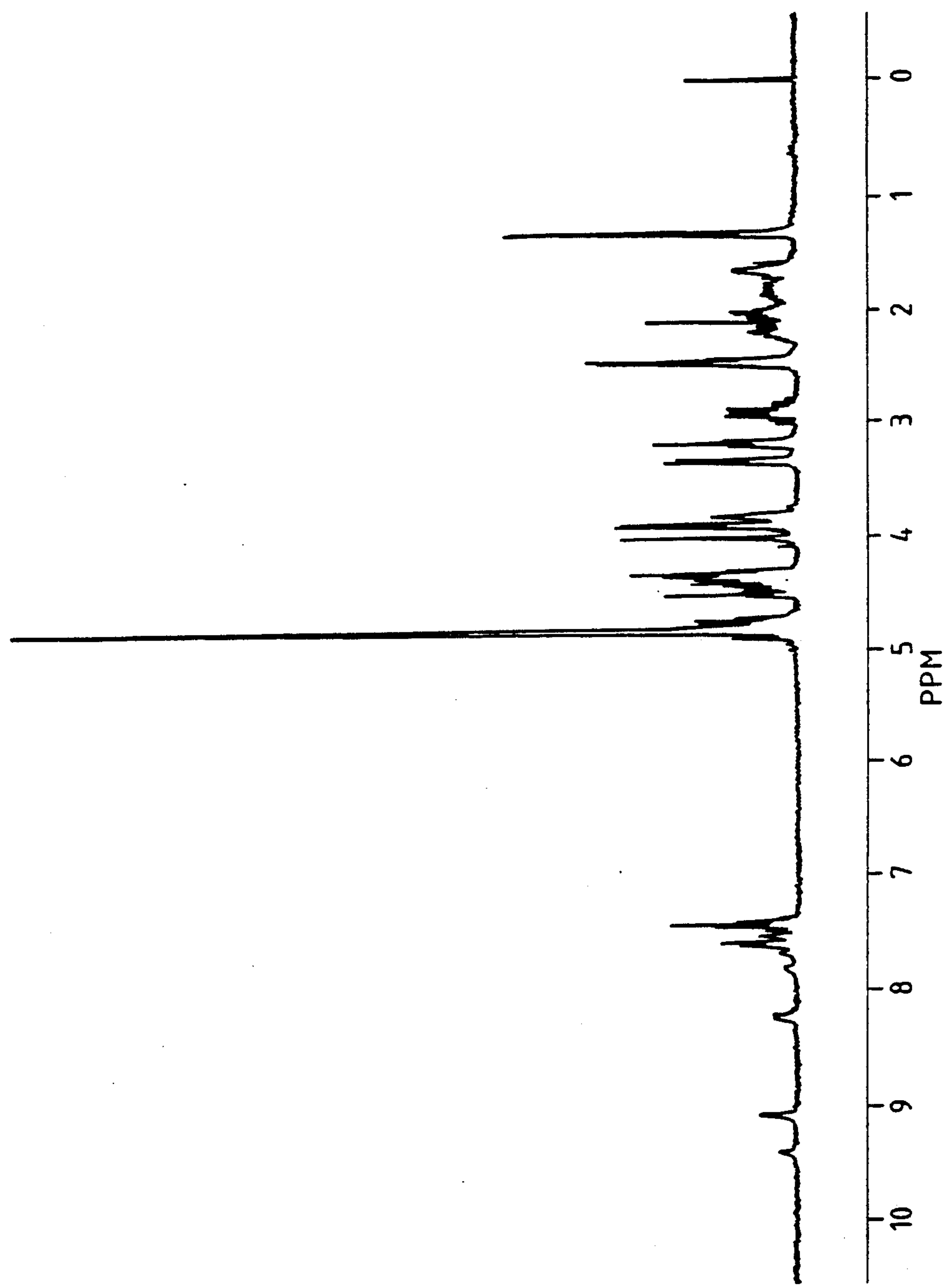
Figure 16:
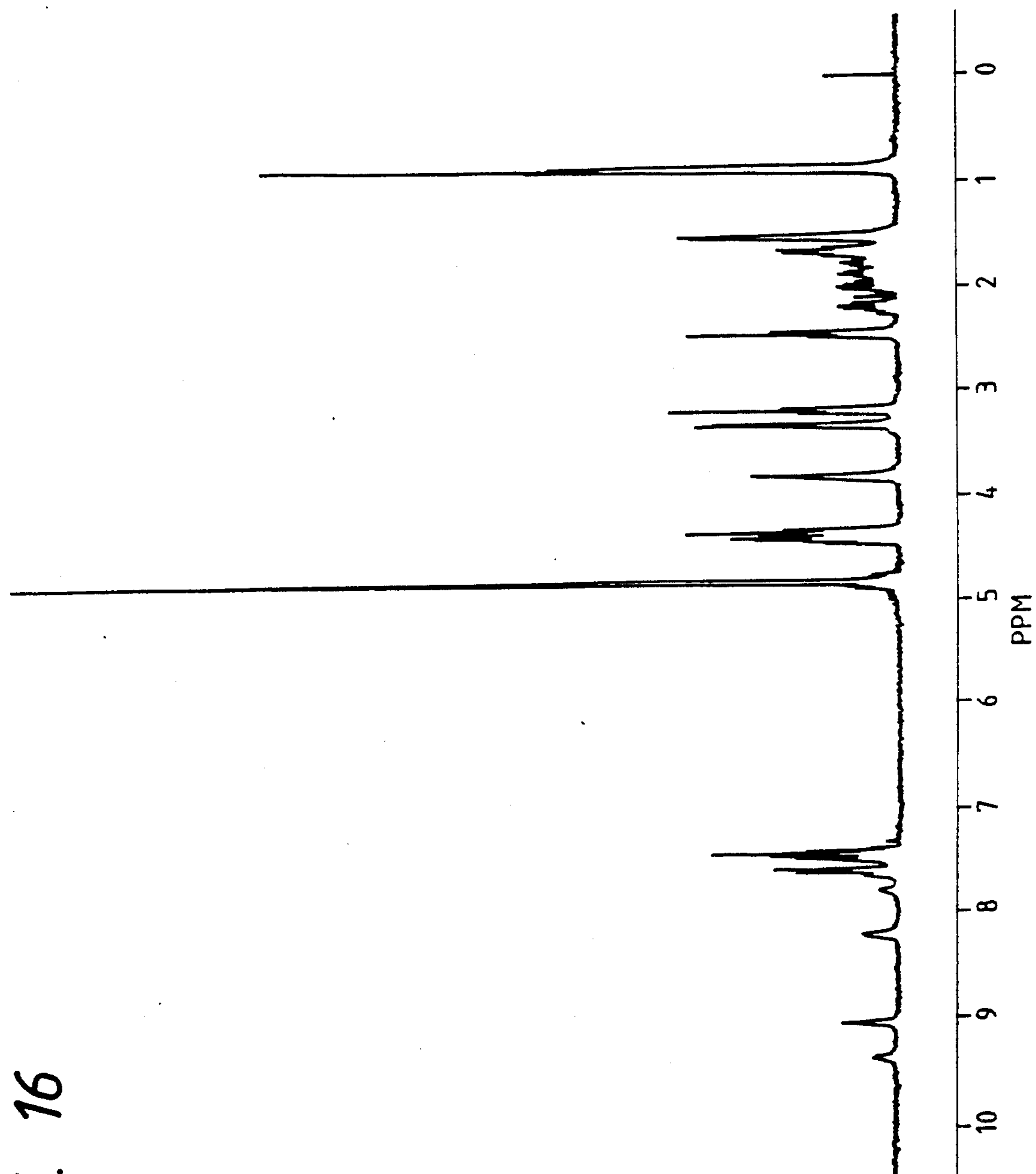
Figure 17:
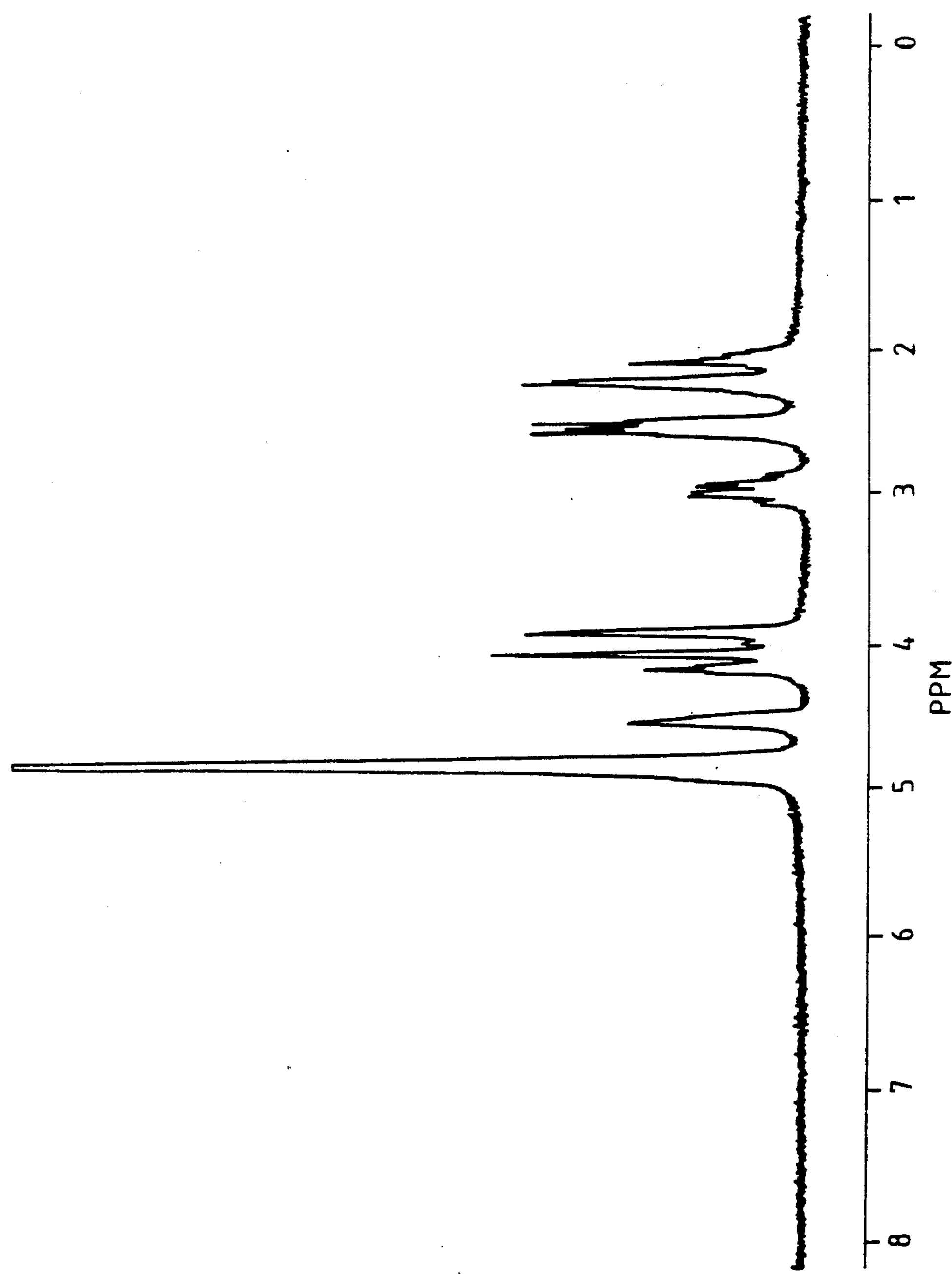
Figure 18:
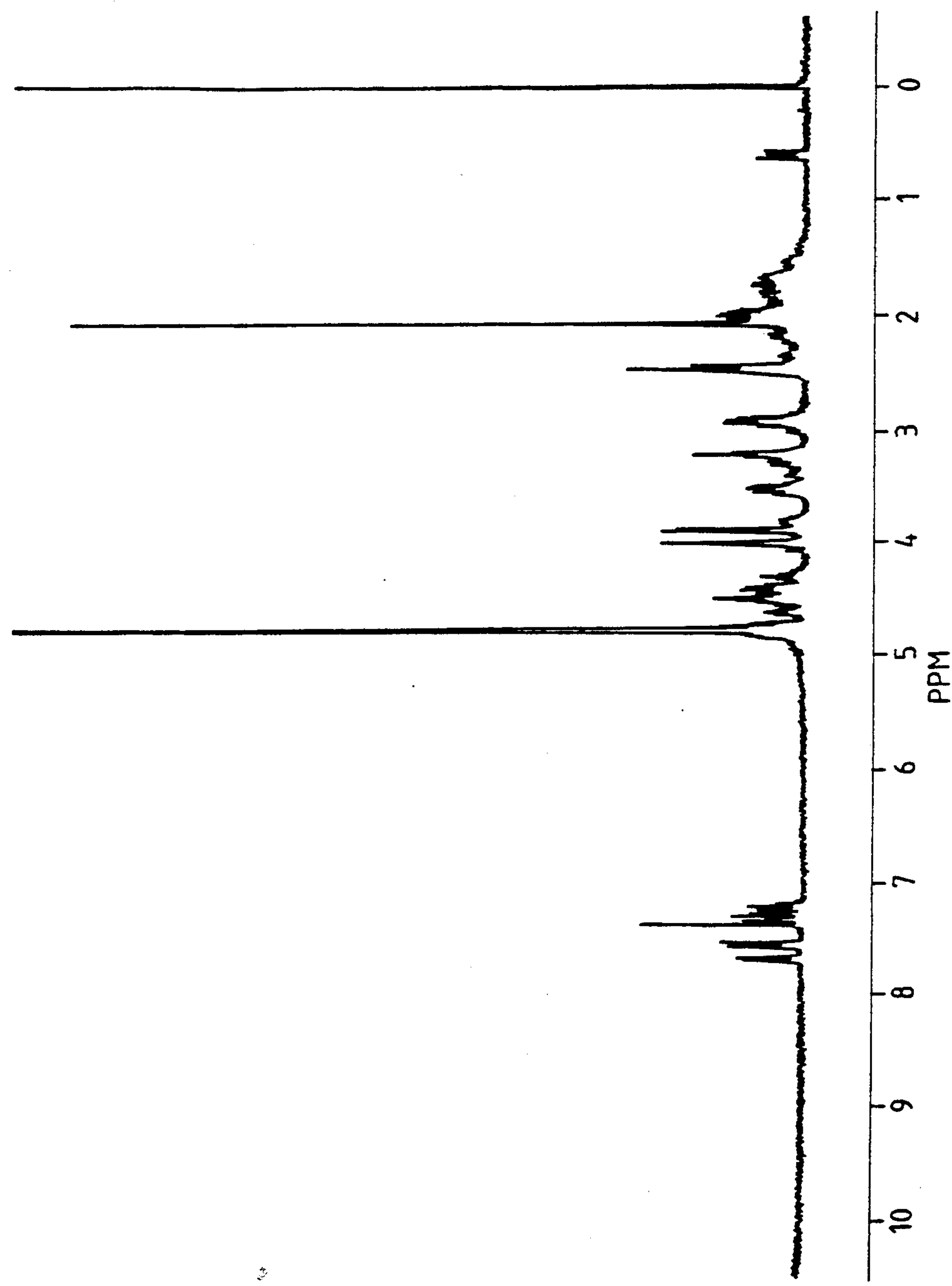
Figure 19:
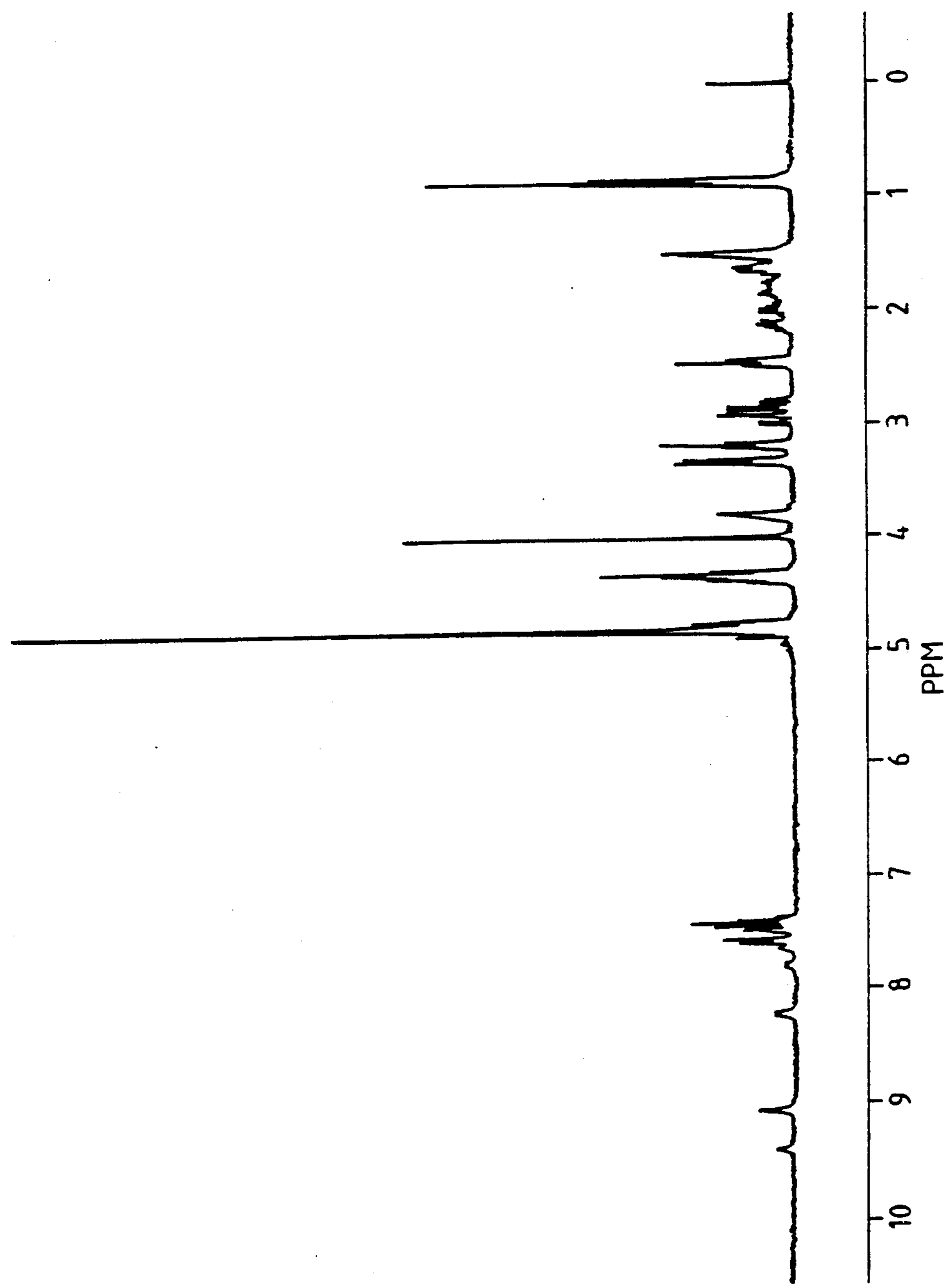
Figure 20:
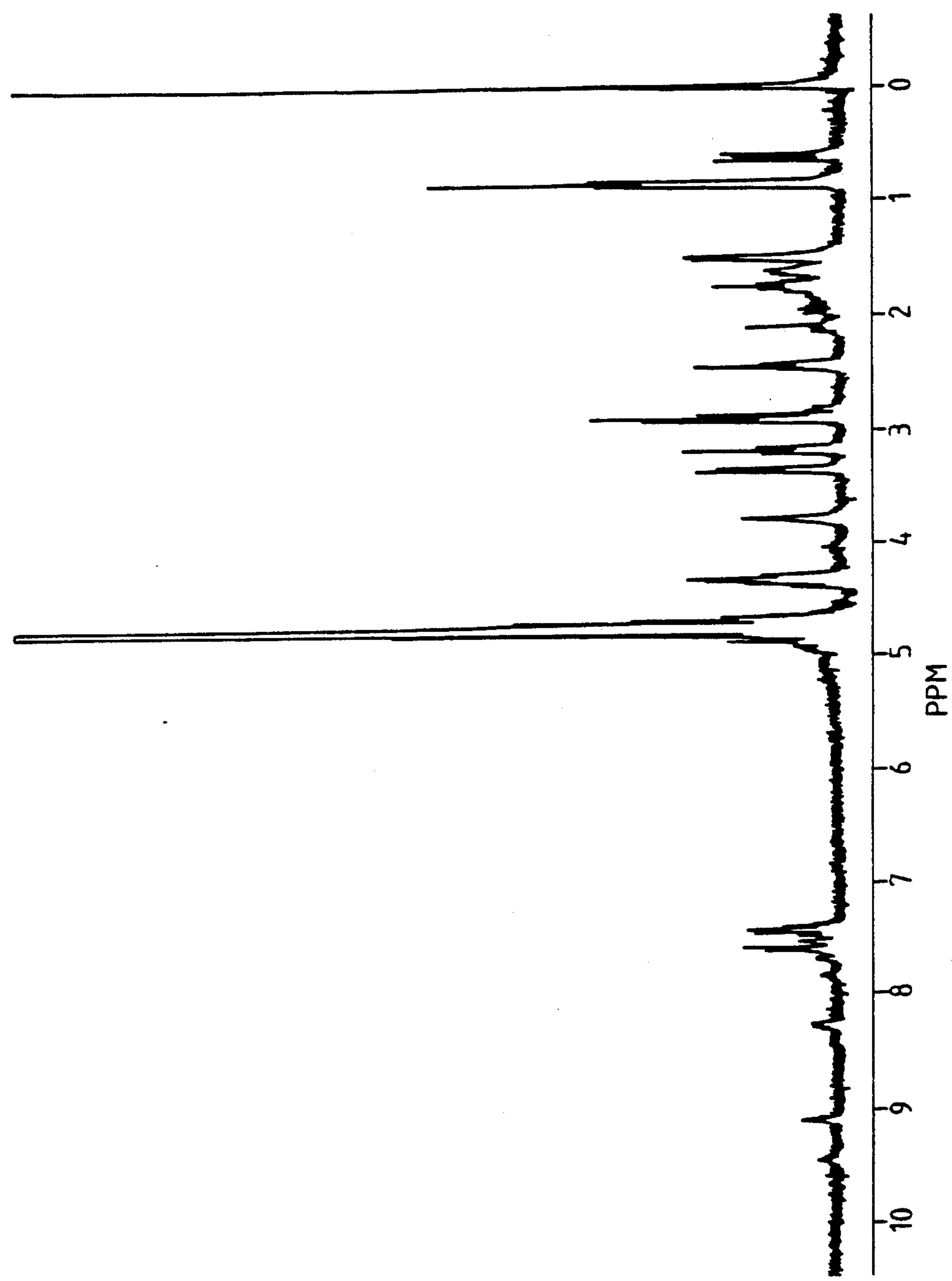
Figure 21:
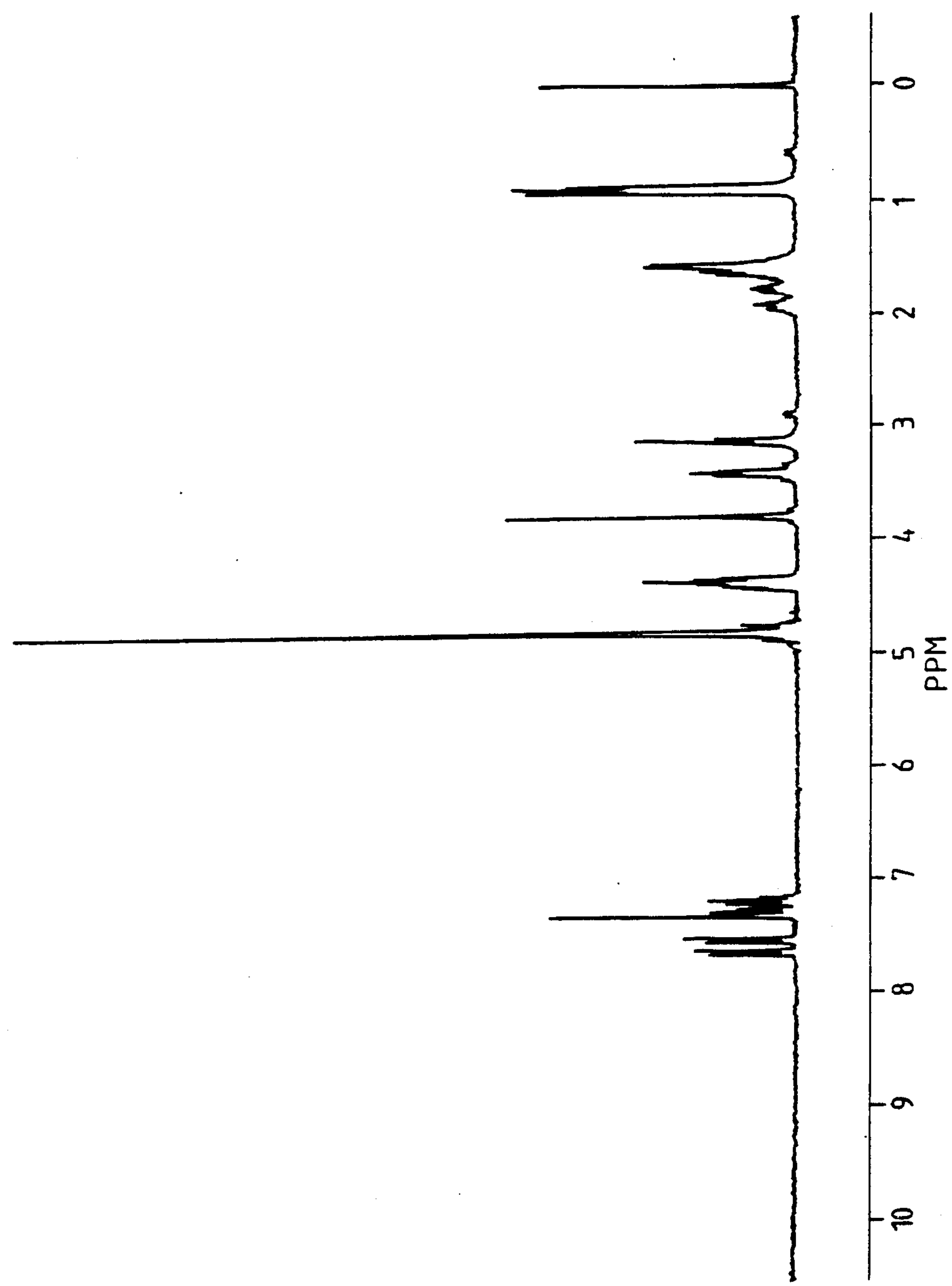
Figure 22:
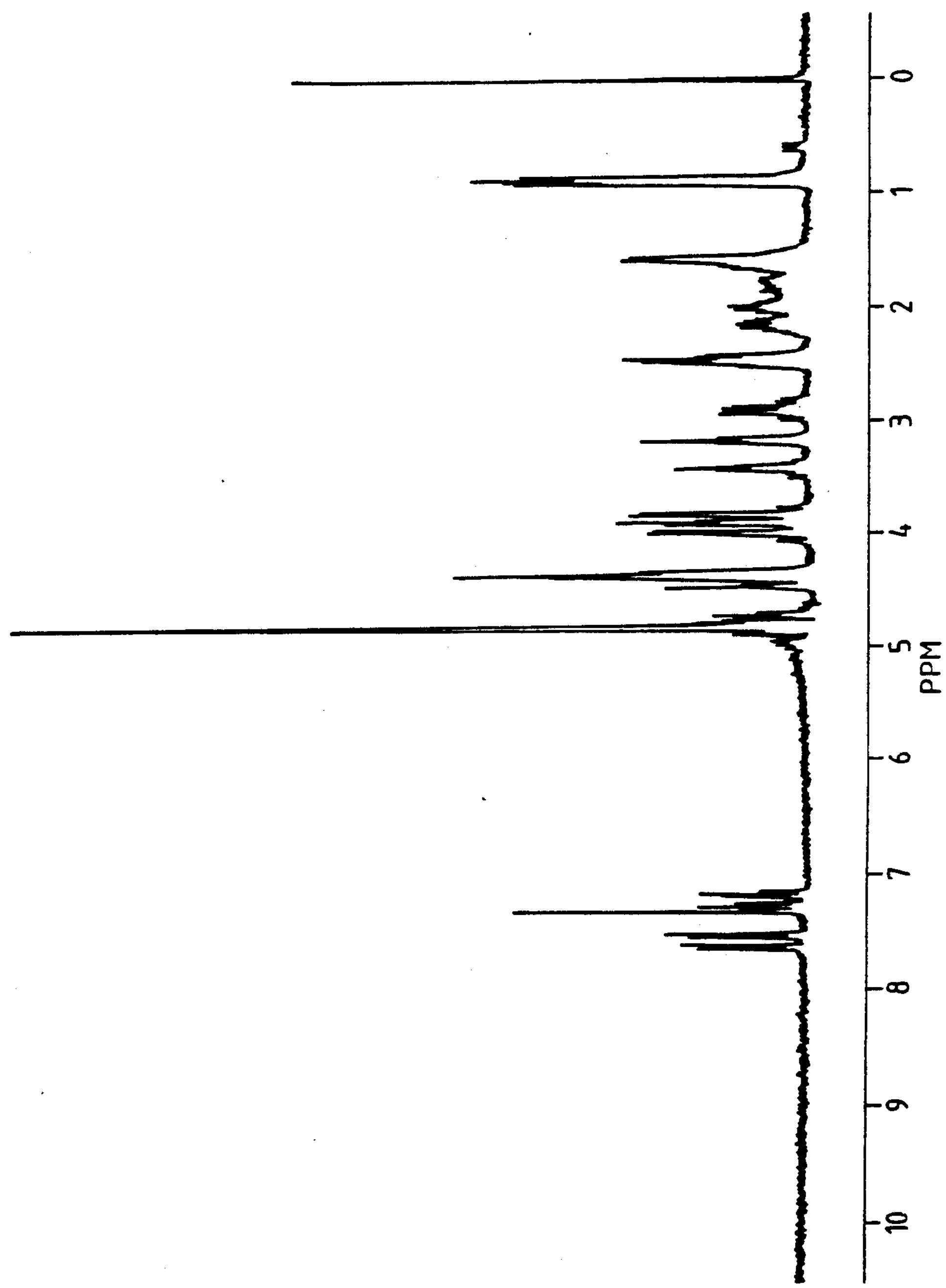
Figure 23:
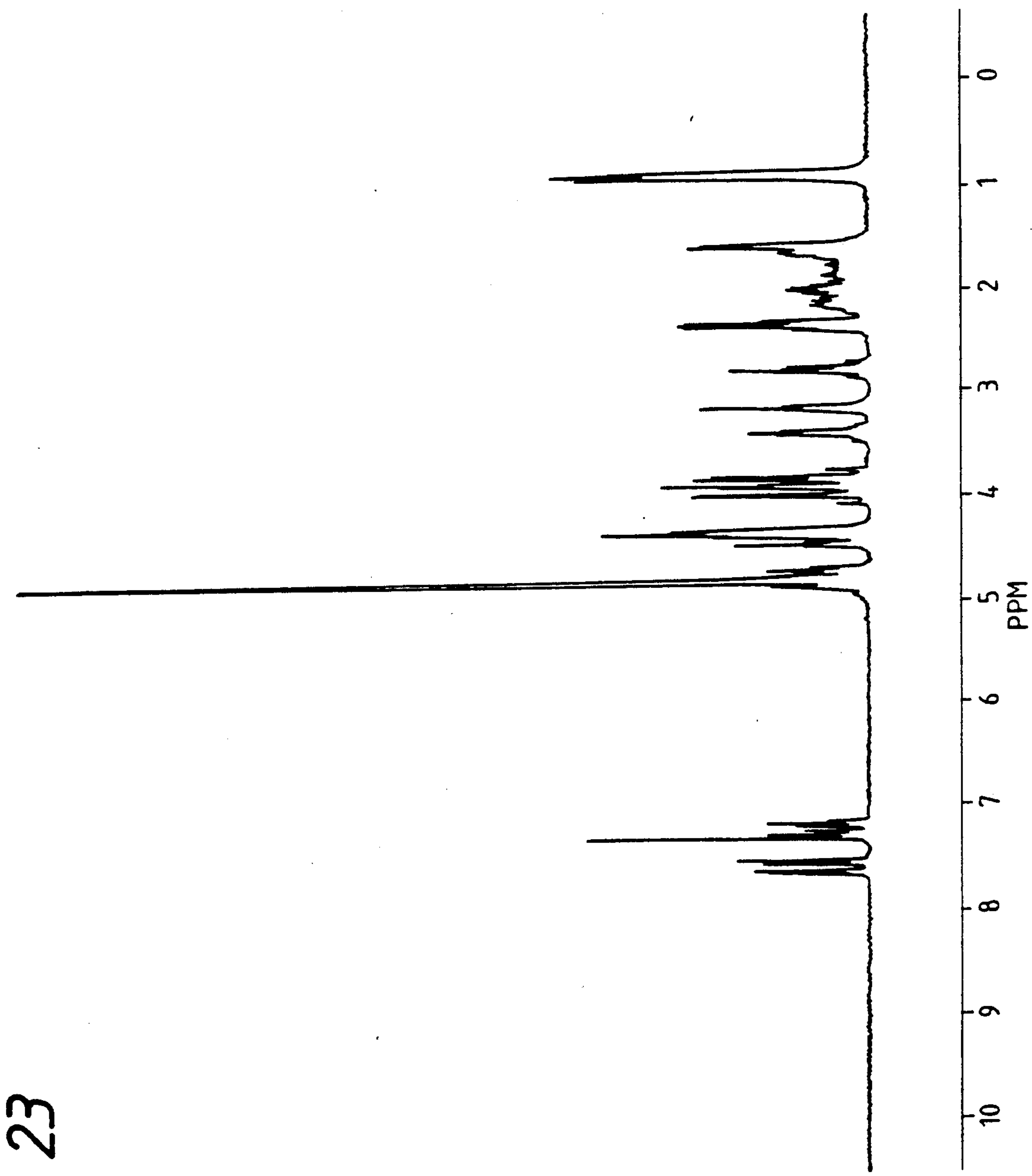
Figure 24:
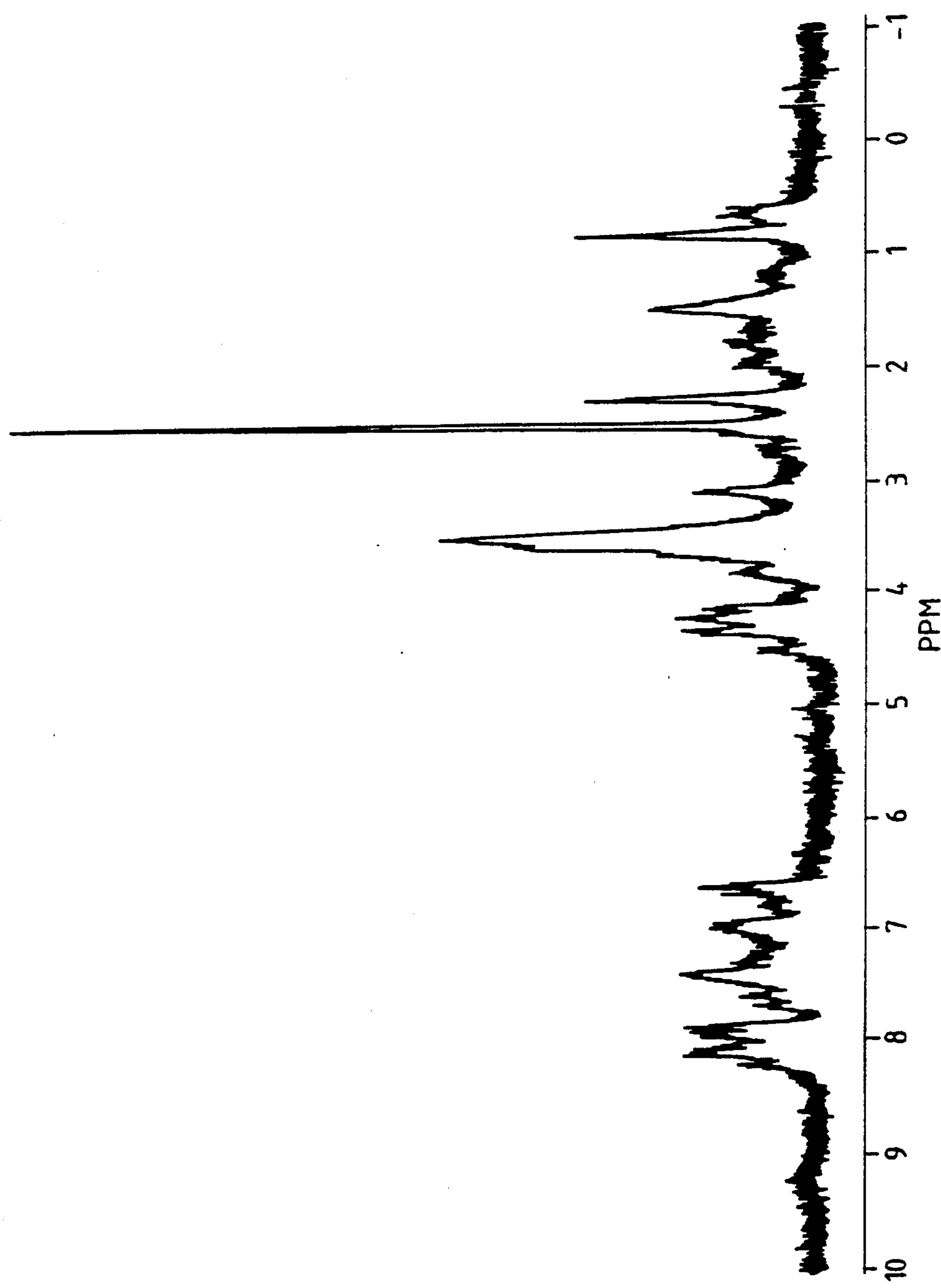
Figure 25:
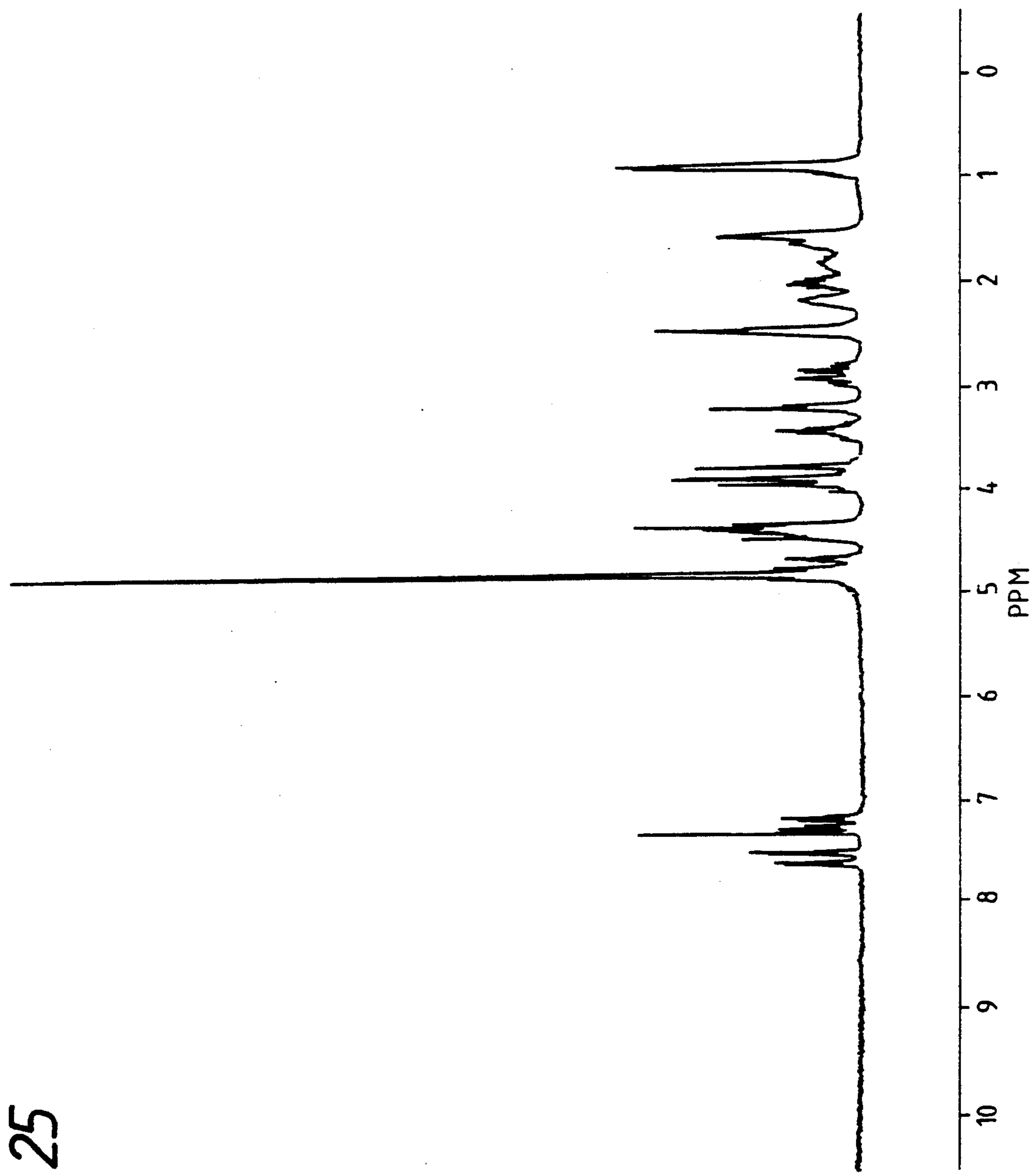
Figure 26:
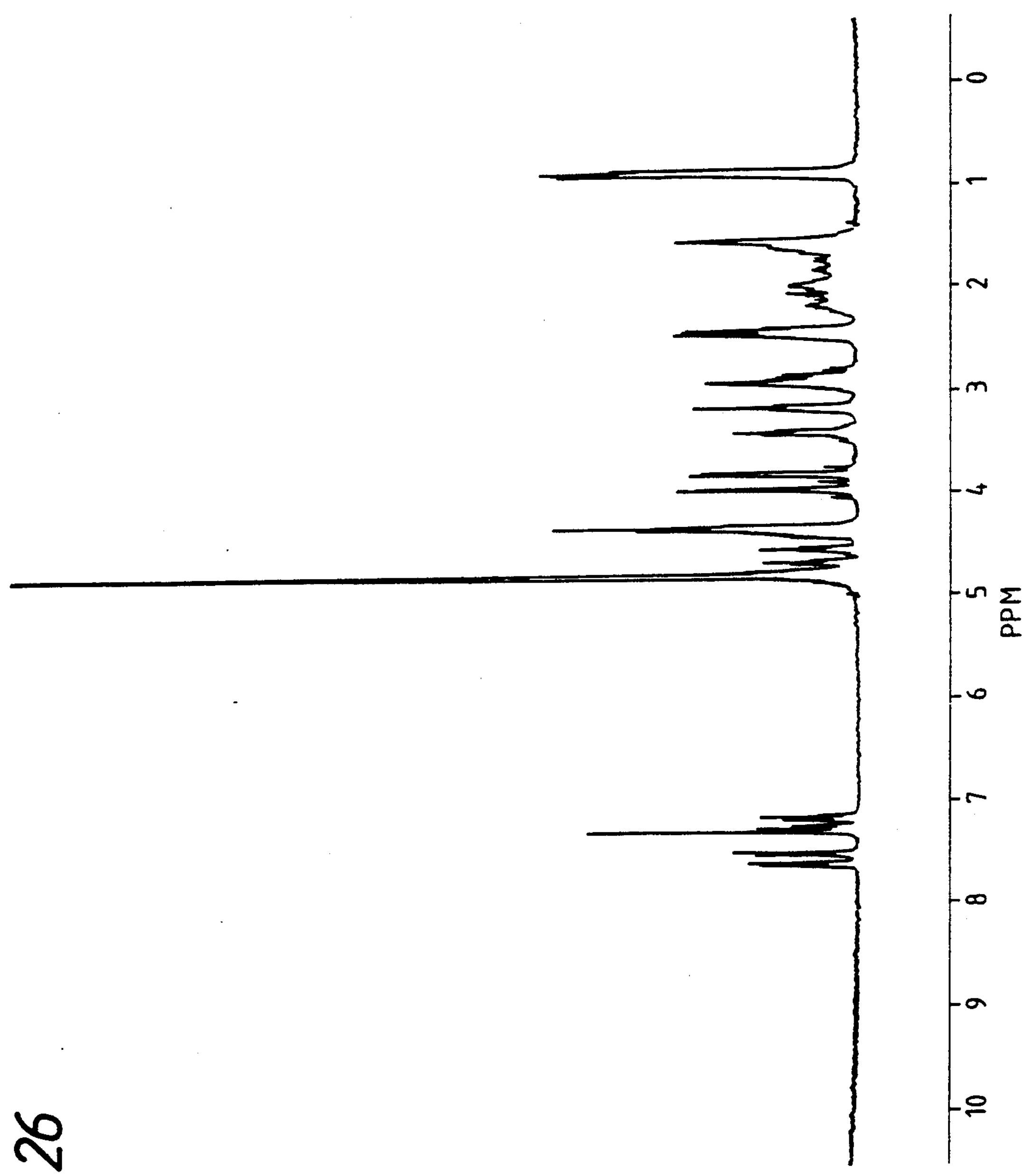
Figure 27:
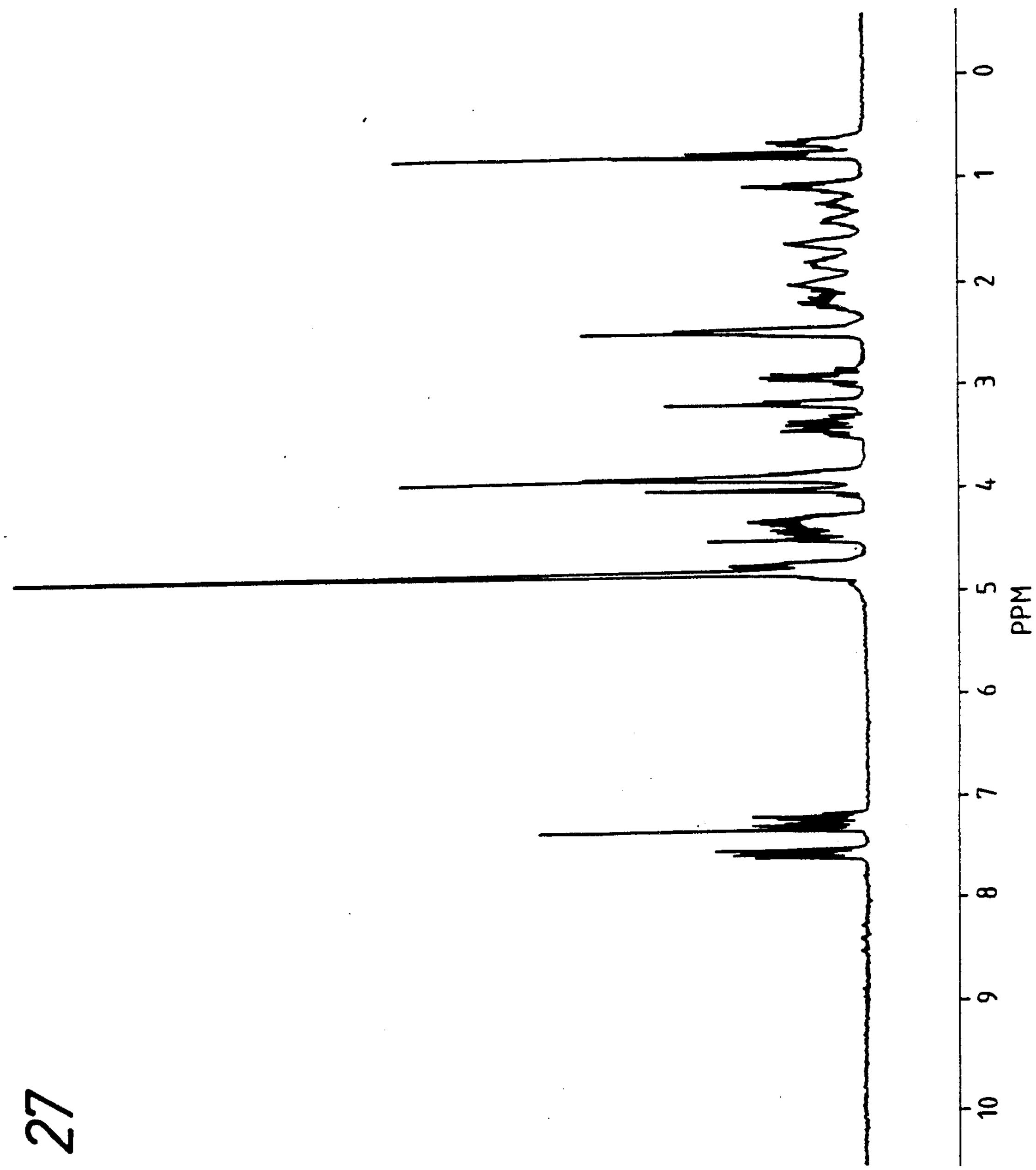
Figure 28:
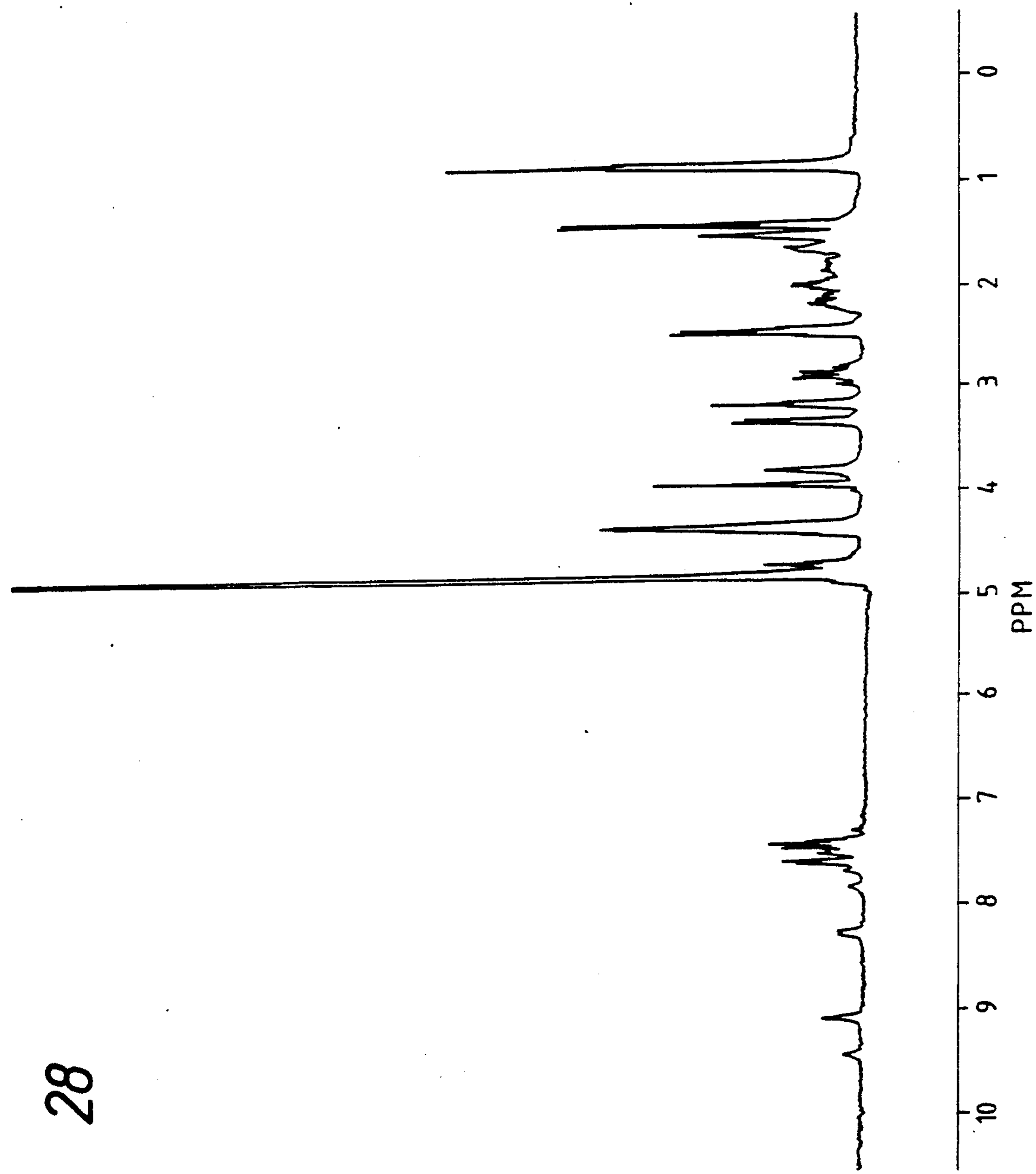
Figure 29:
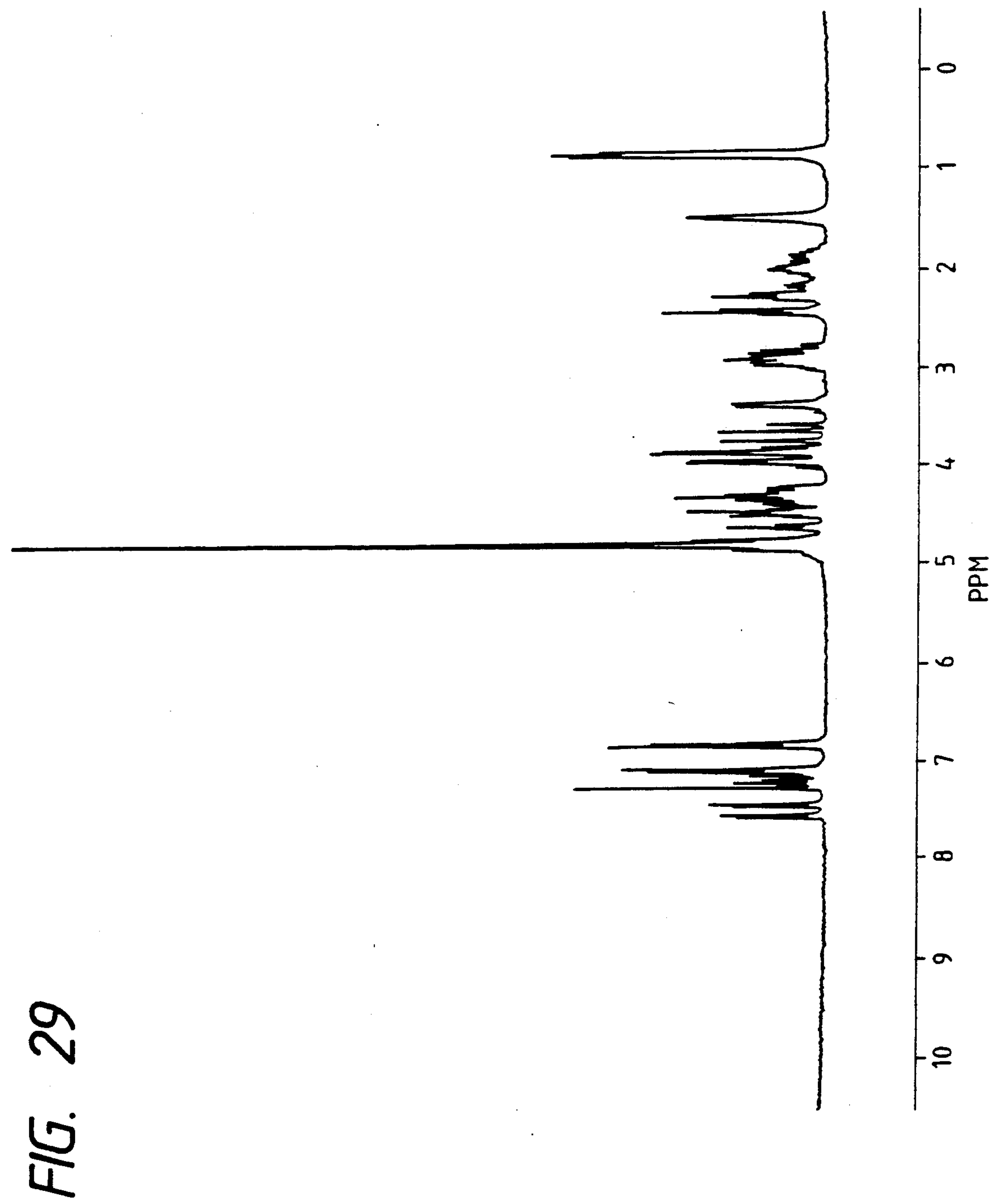
Figure 30:
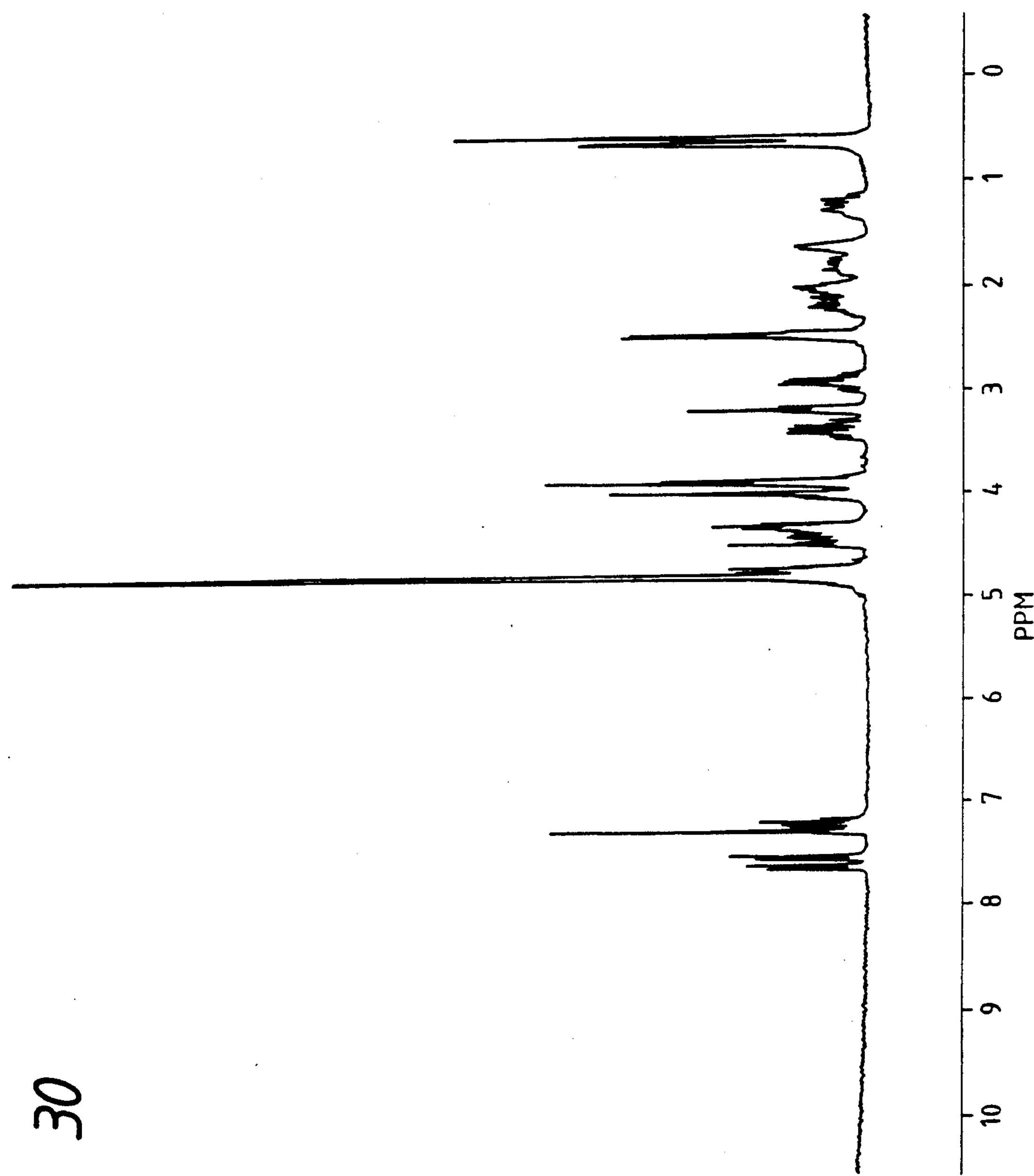
Figure 31:
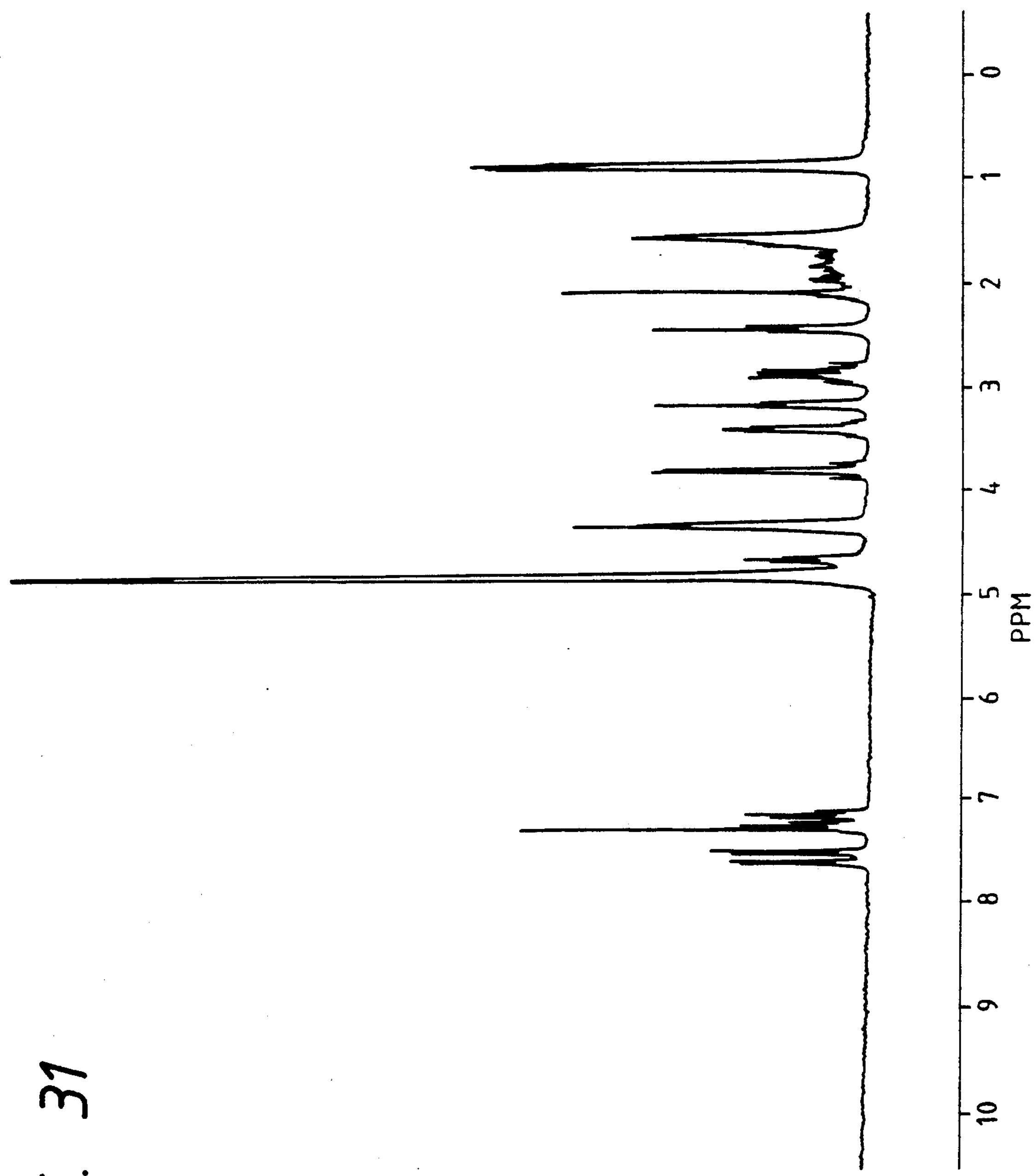
Figure 32:
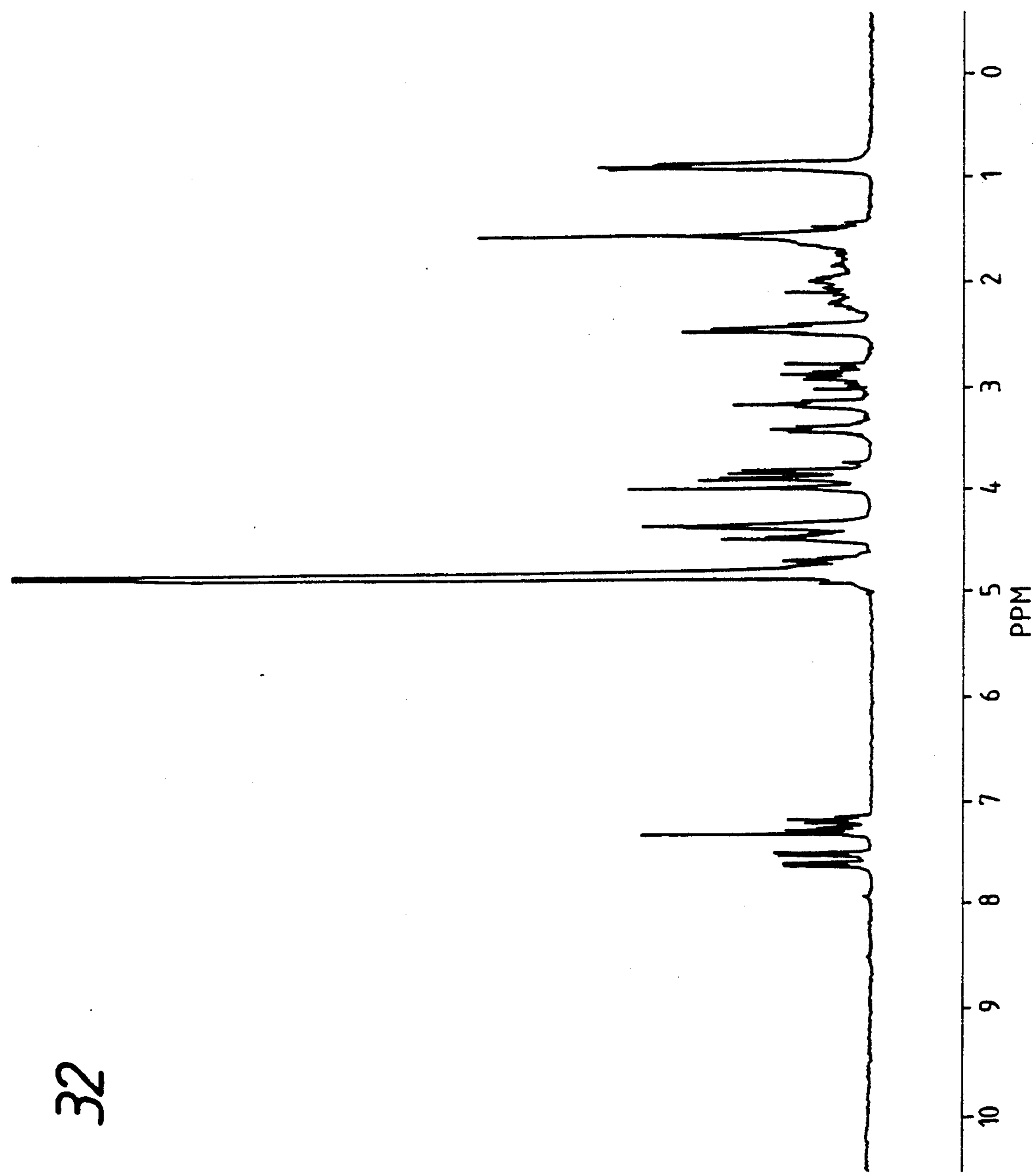
Figure 33:
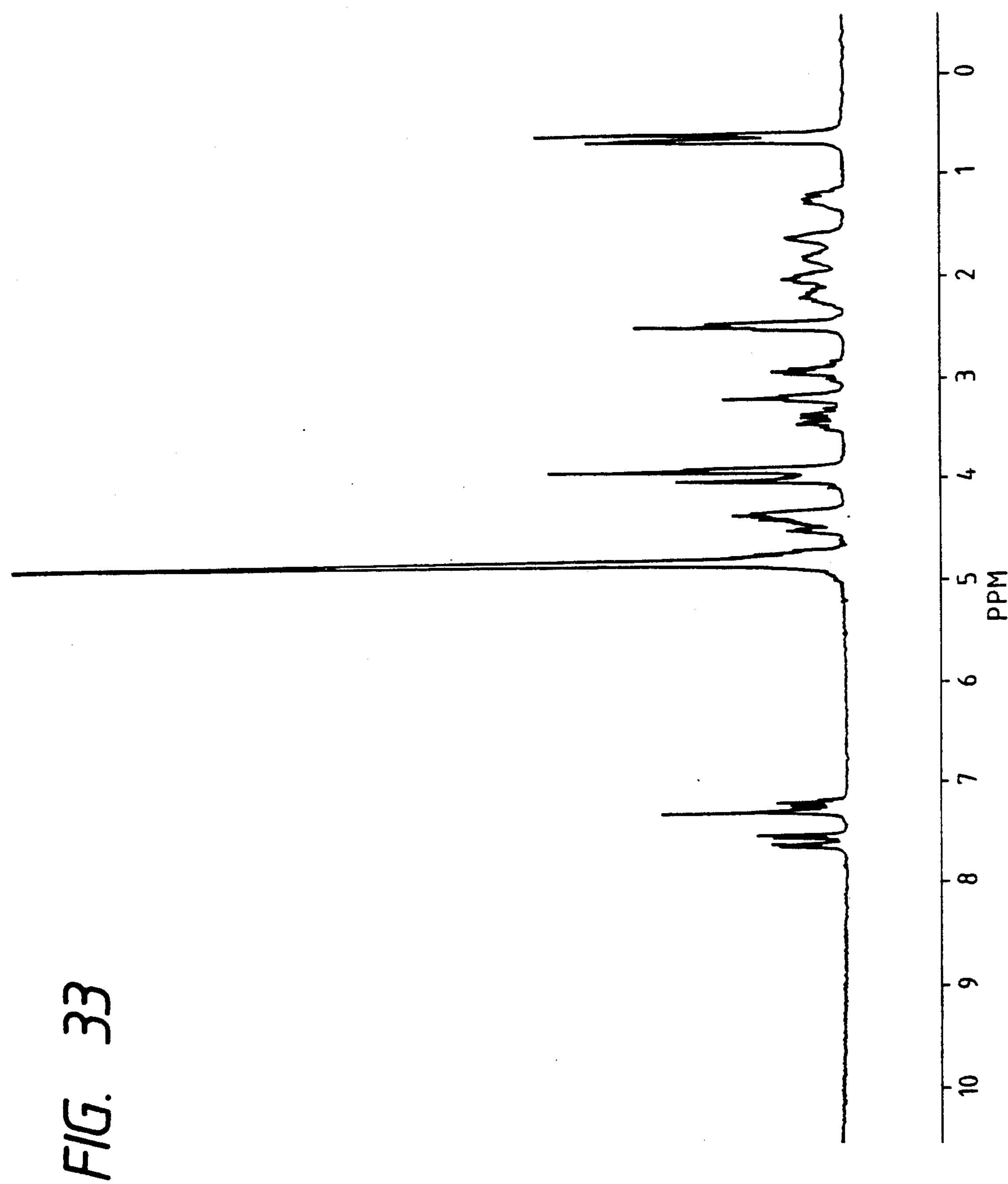
Figure 34:
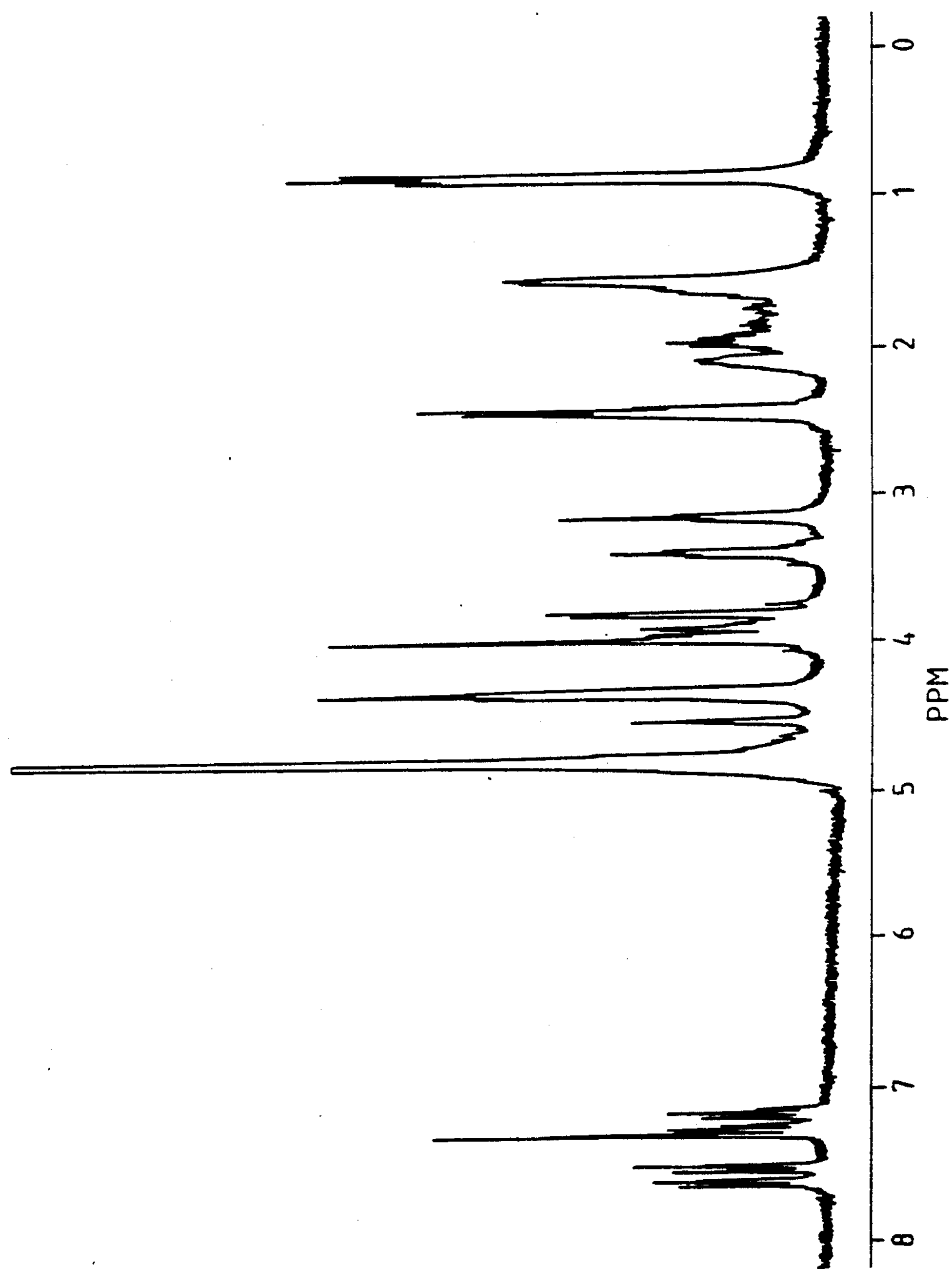
Figure 35:
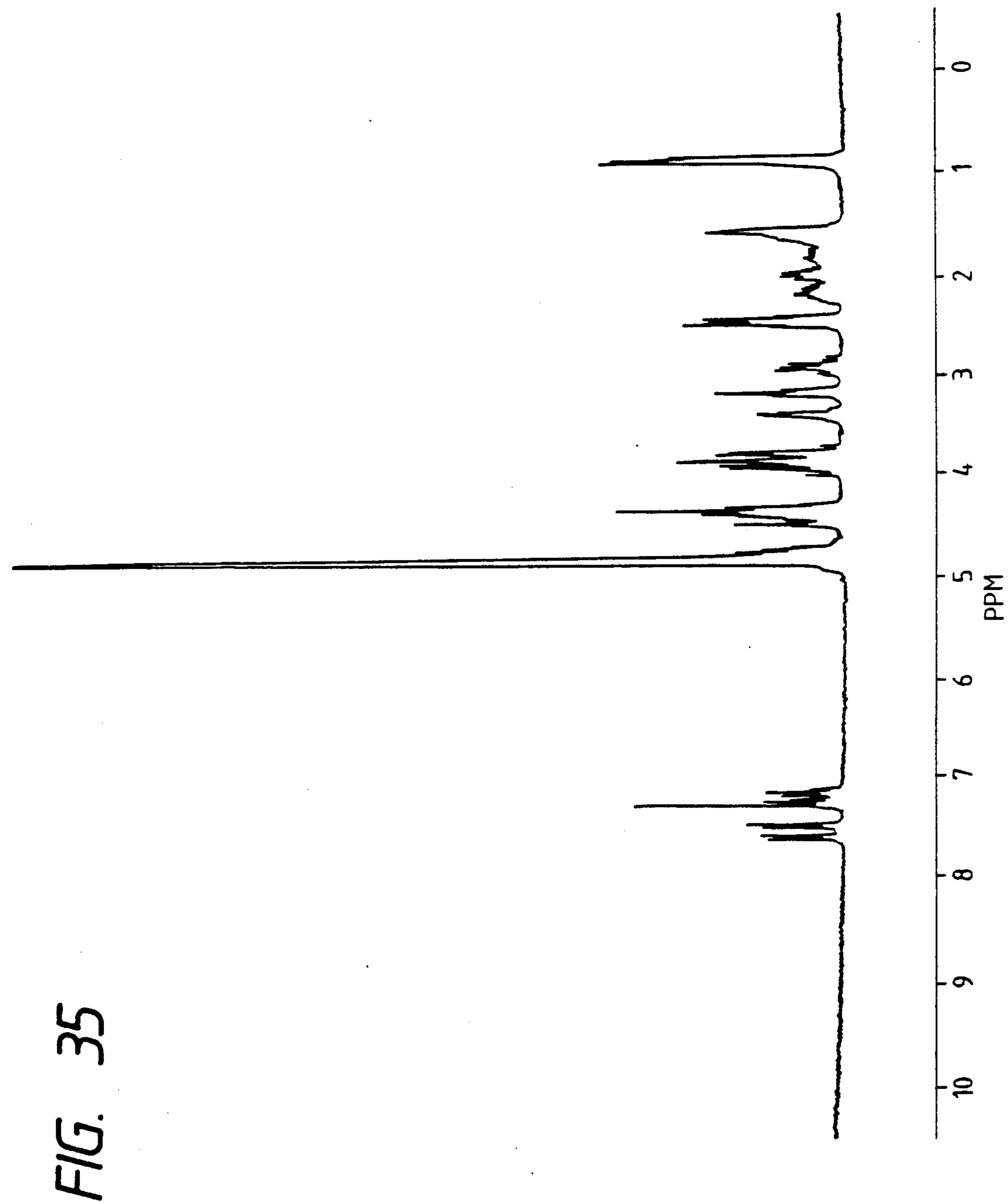
Figure 36:
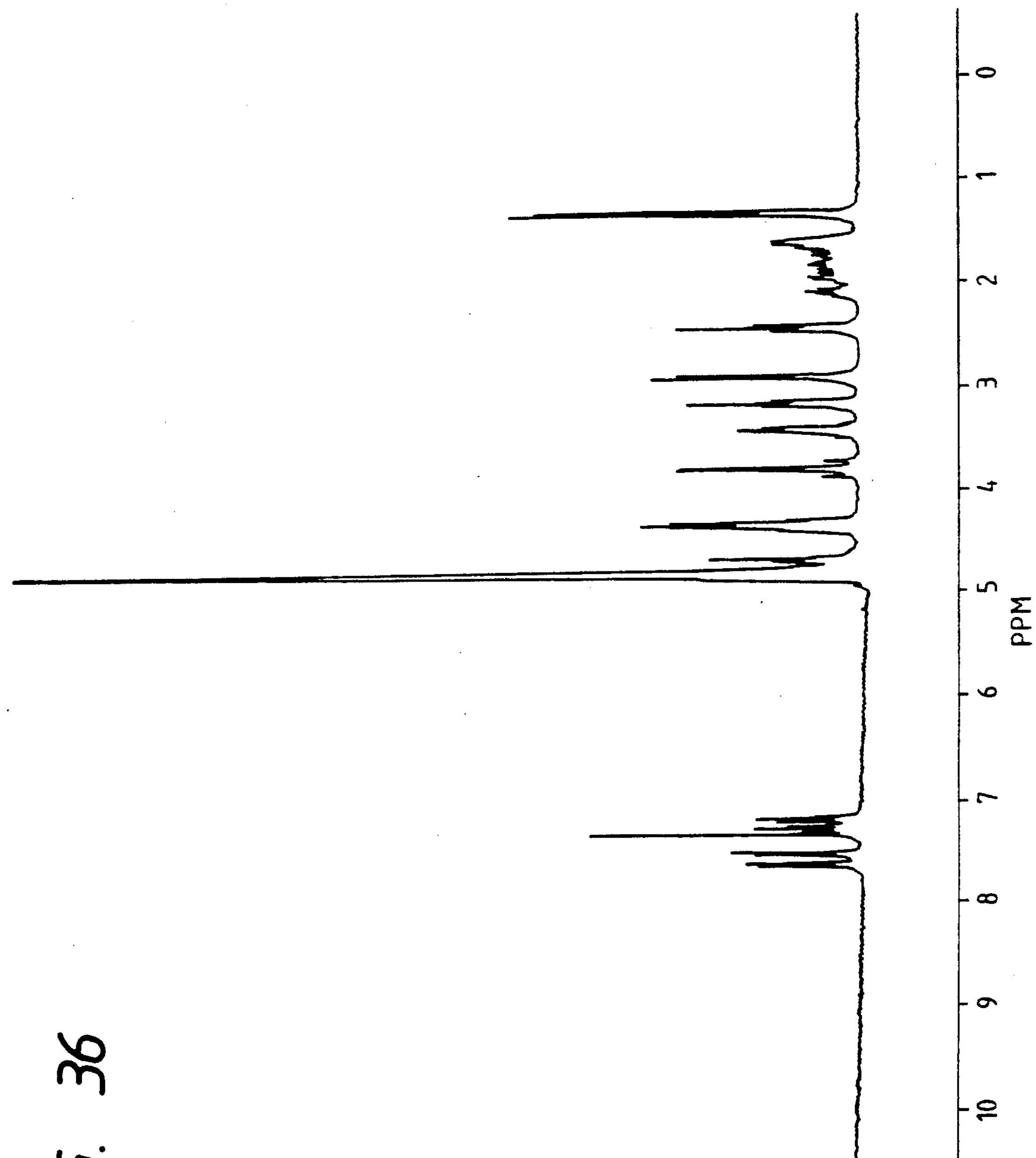
Figure 37:
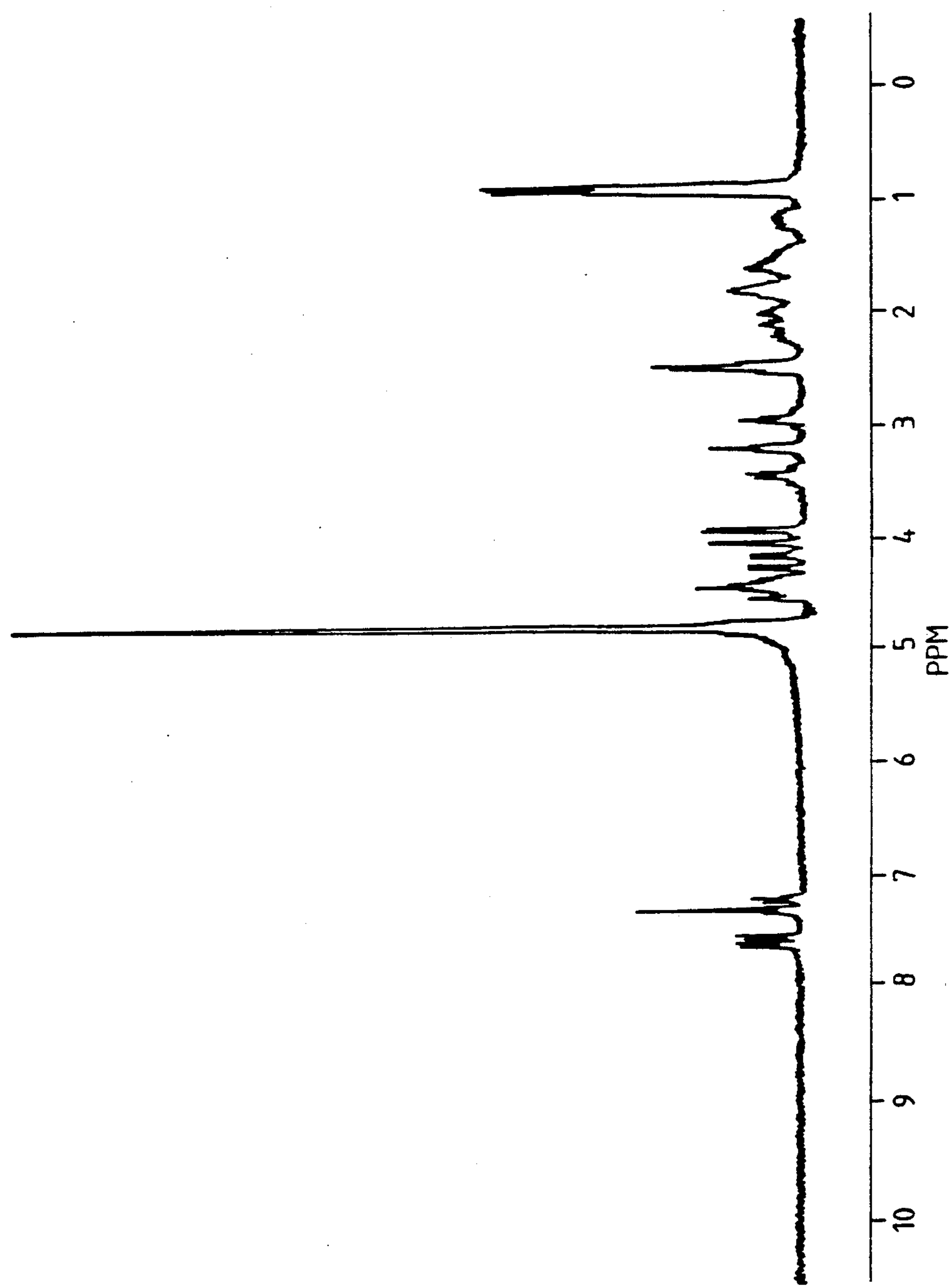
Figure 38:
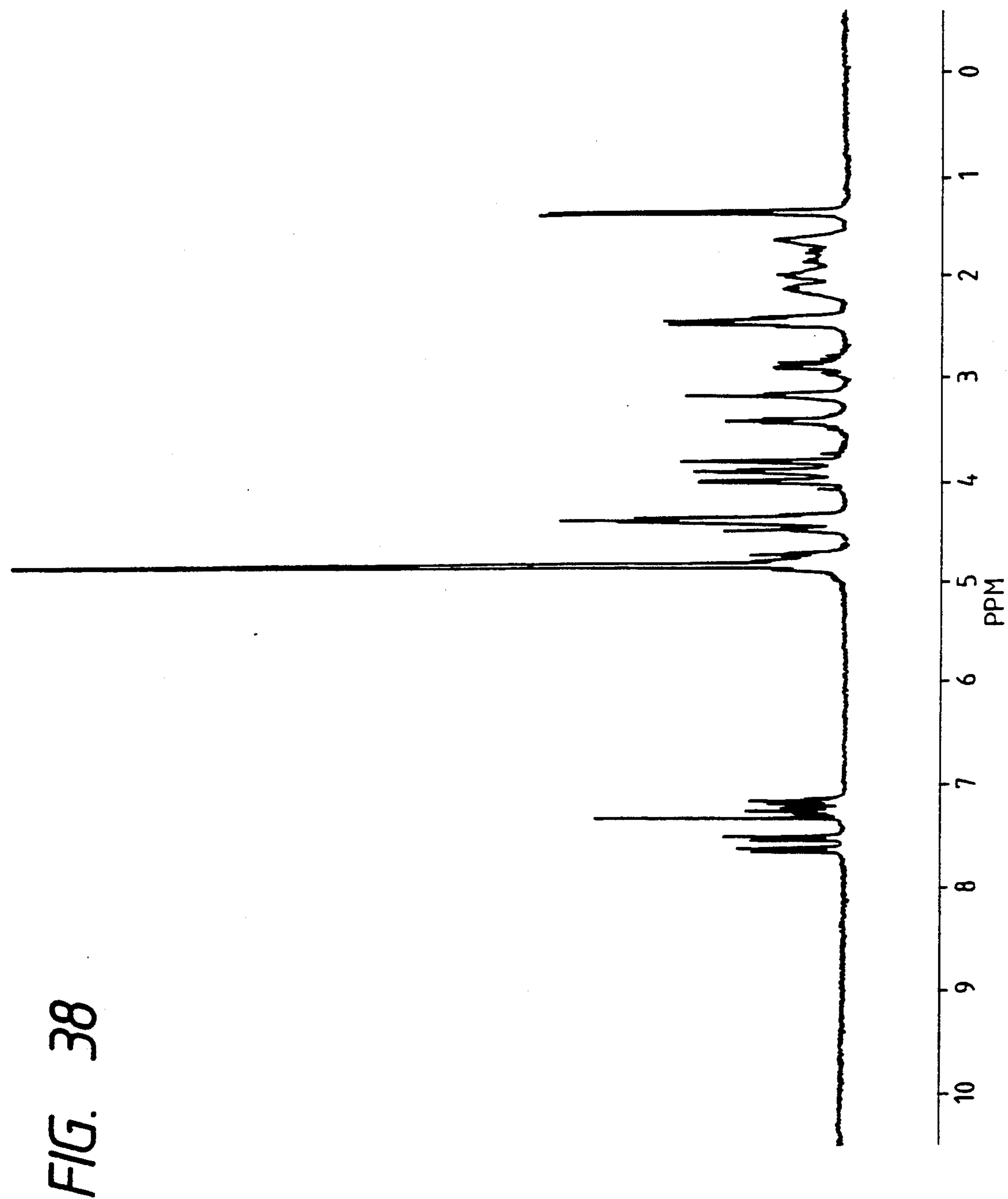
Figure 39:
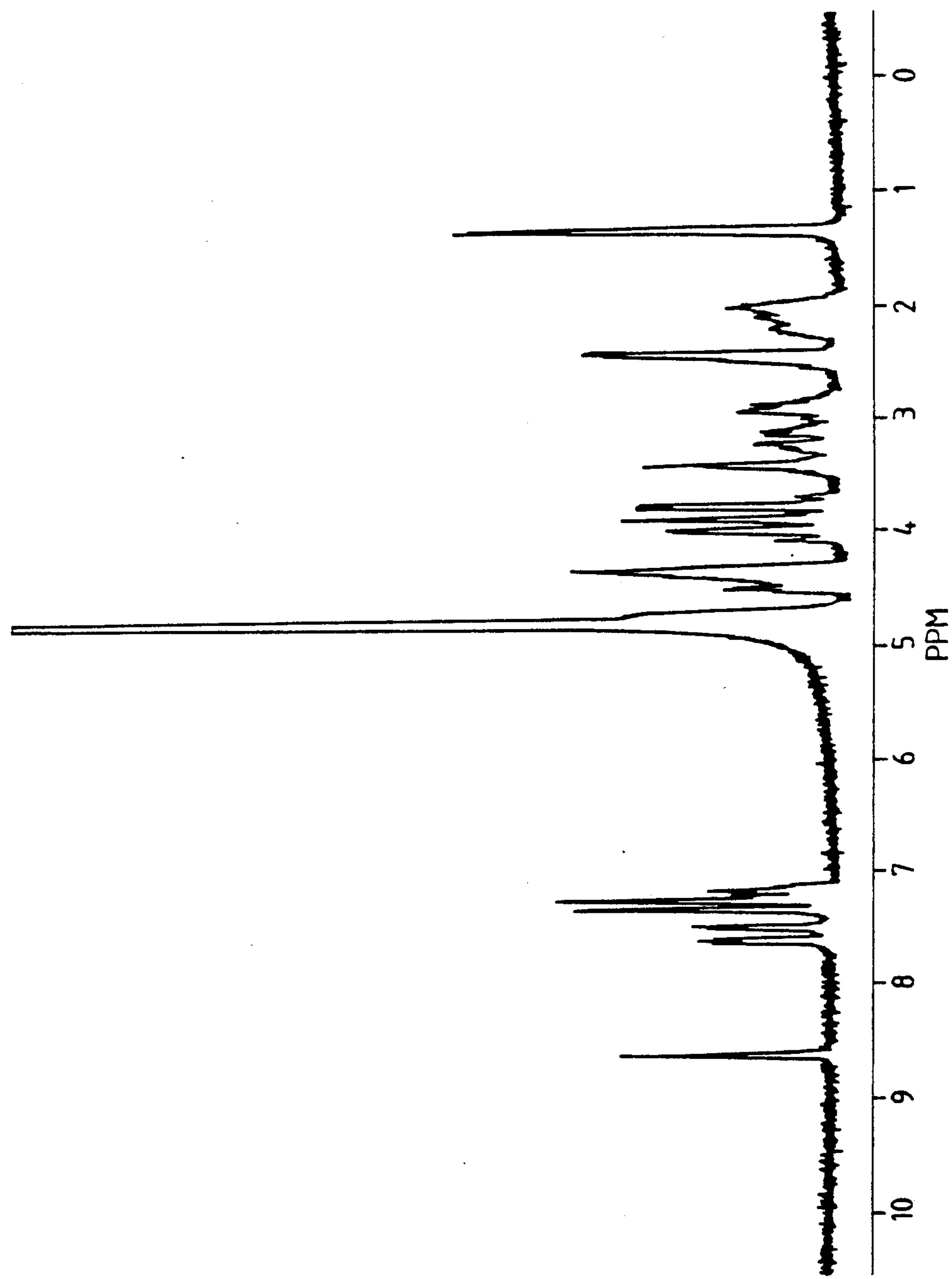
Figure 40:
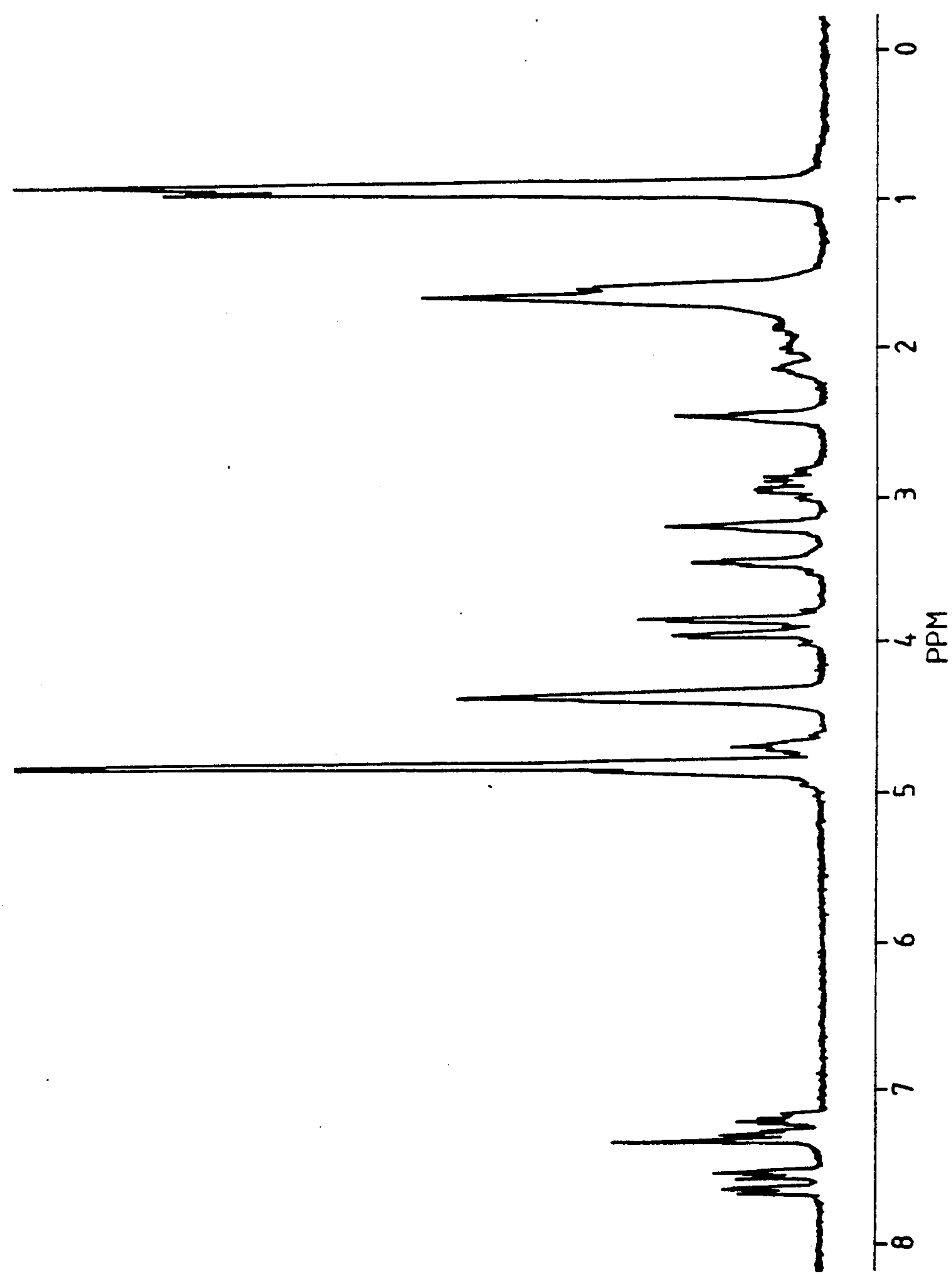
Figure 41:
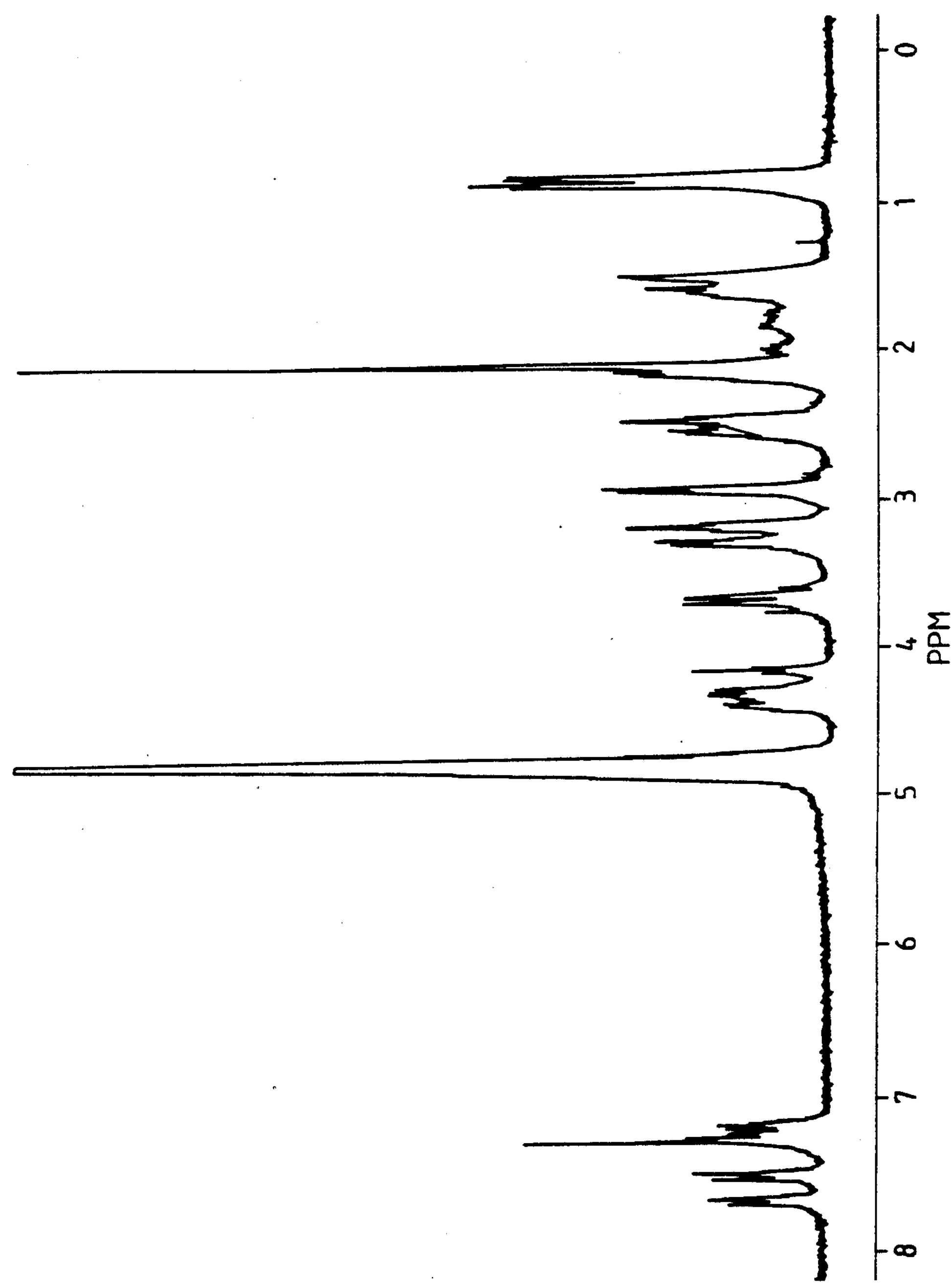
Figure 42:
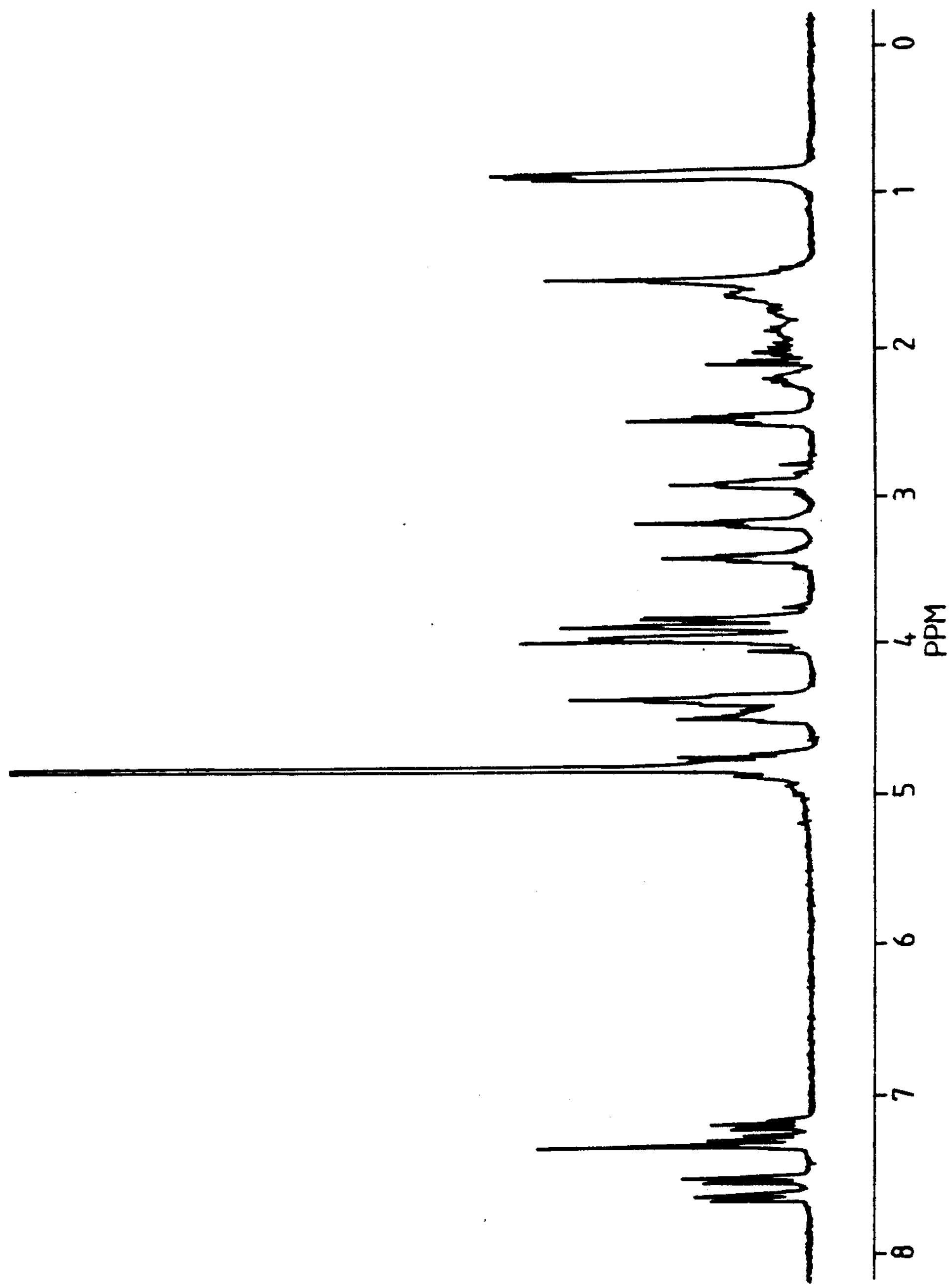
Figure 43:
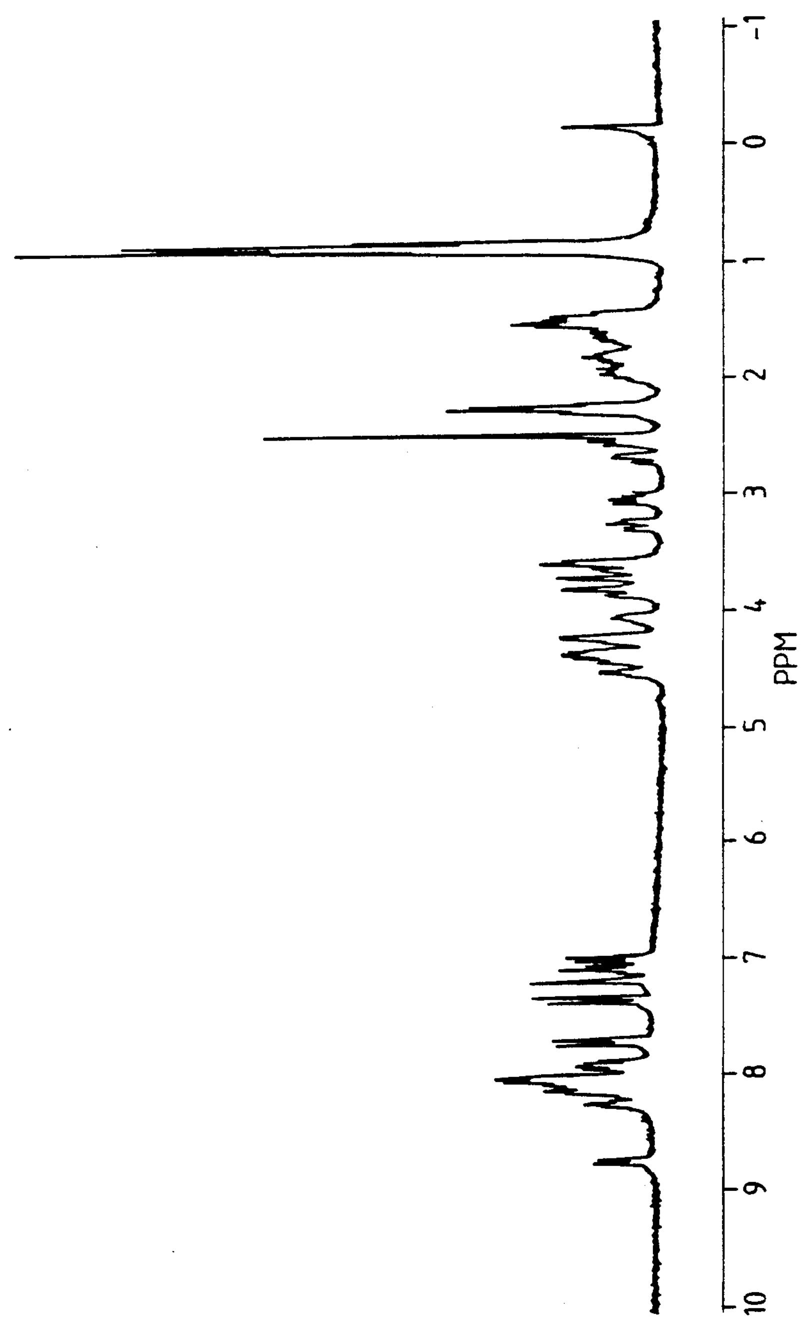
Figure 44:
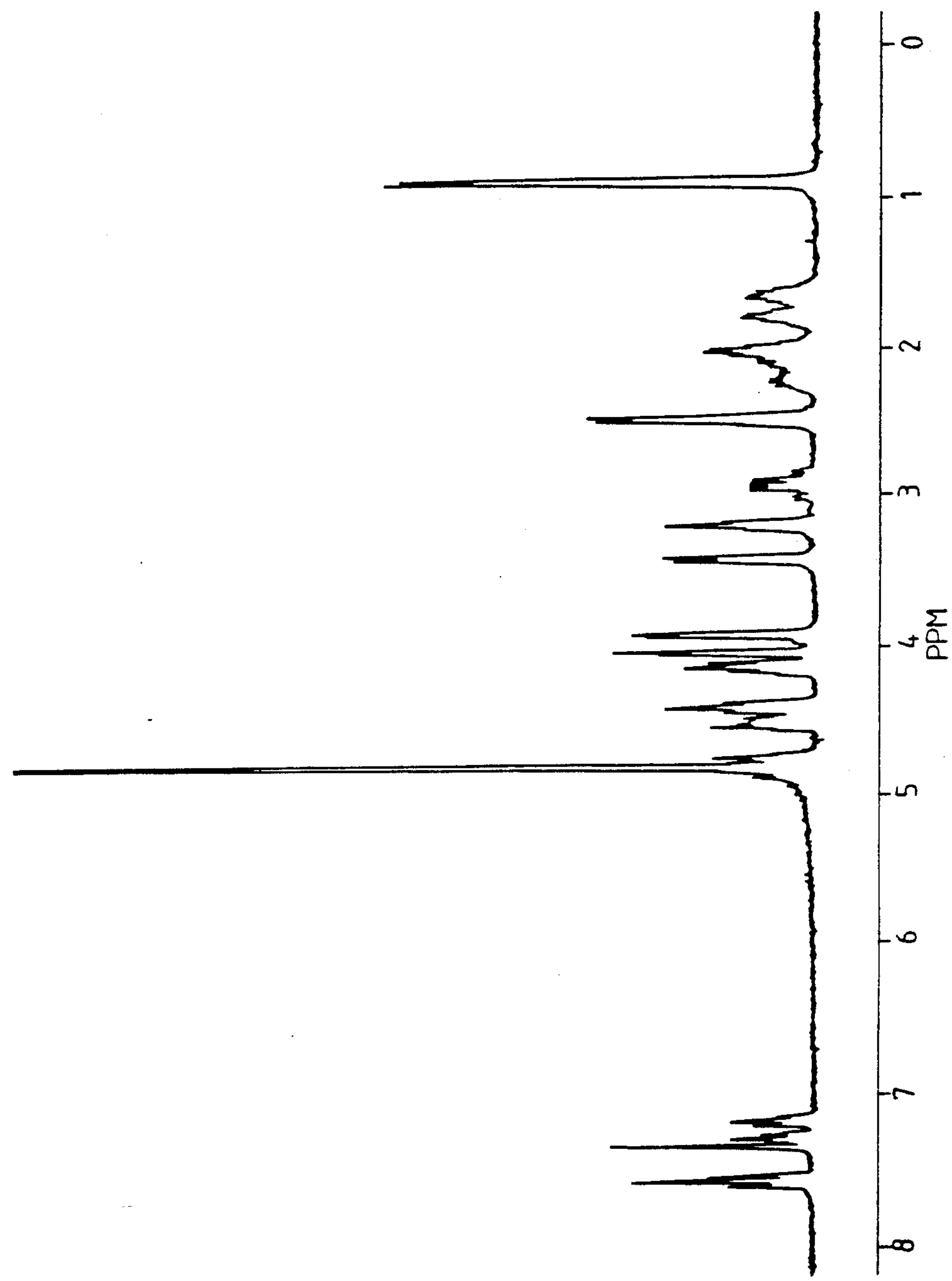
Figure 45:
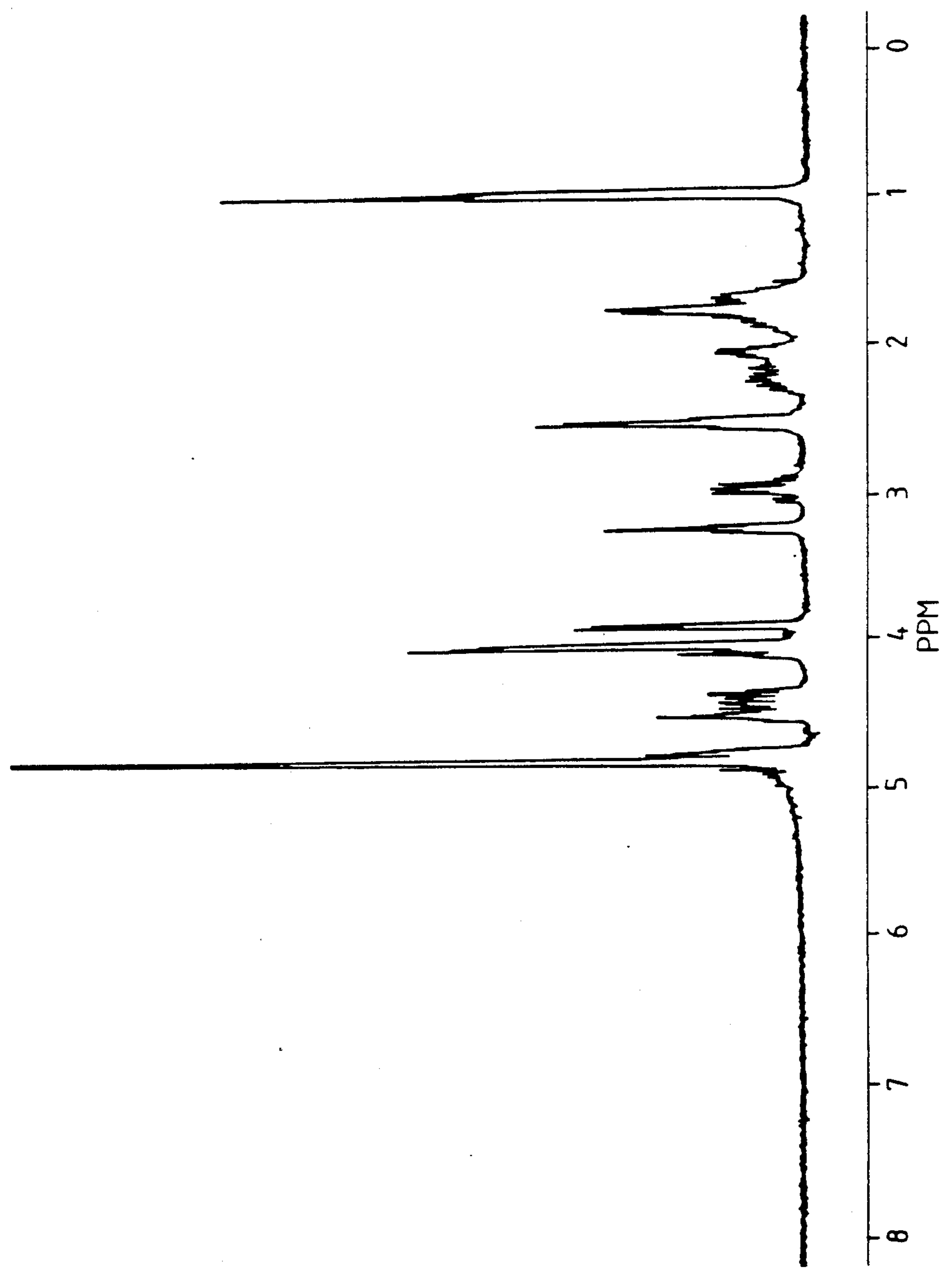
Figure 46:
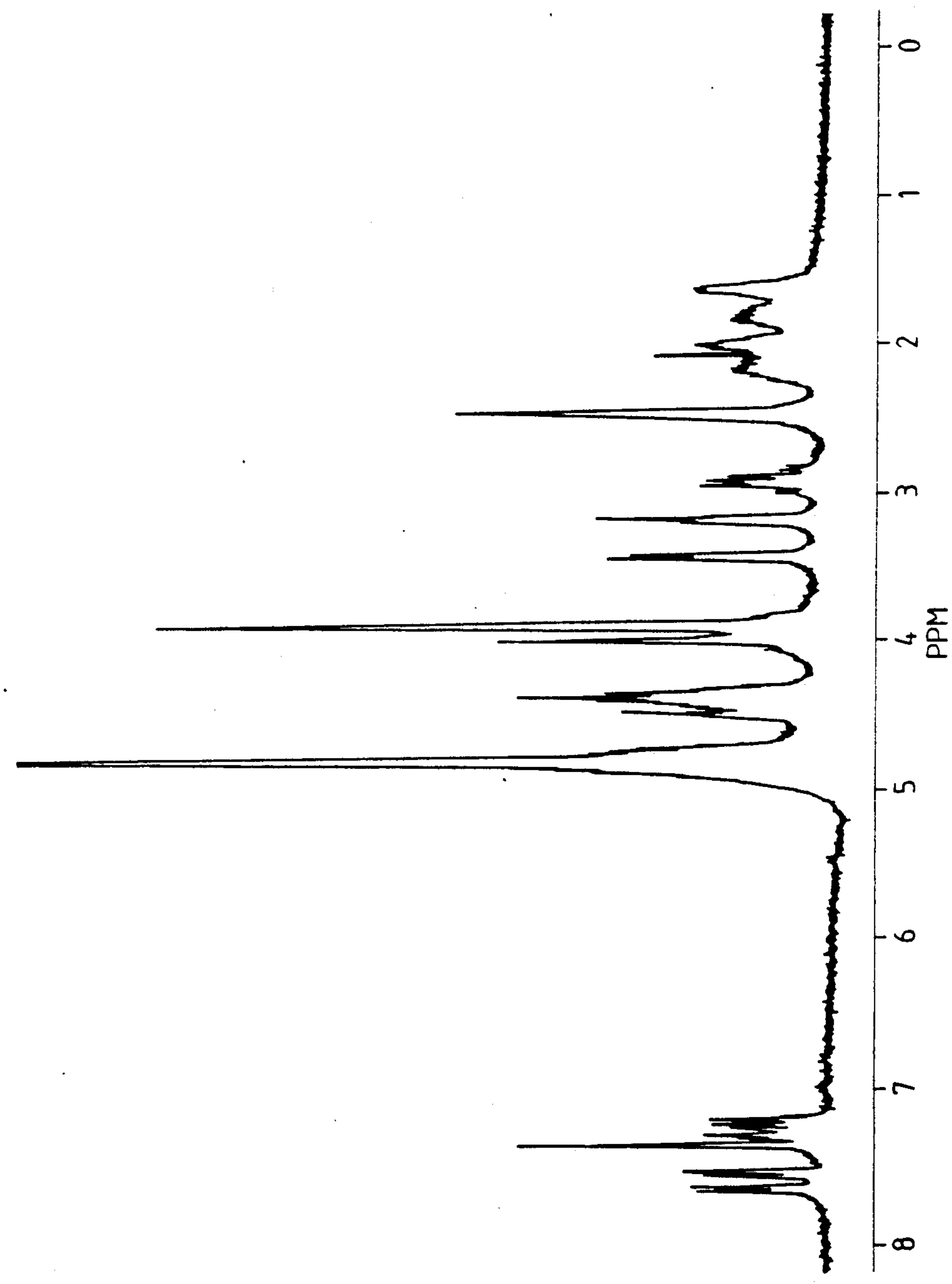
Figure 47:
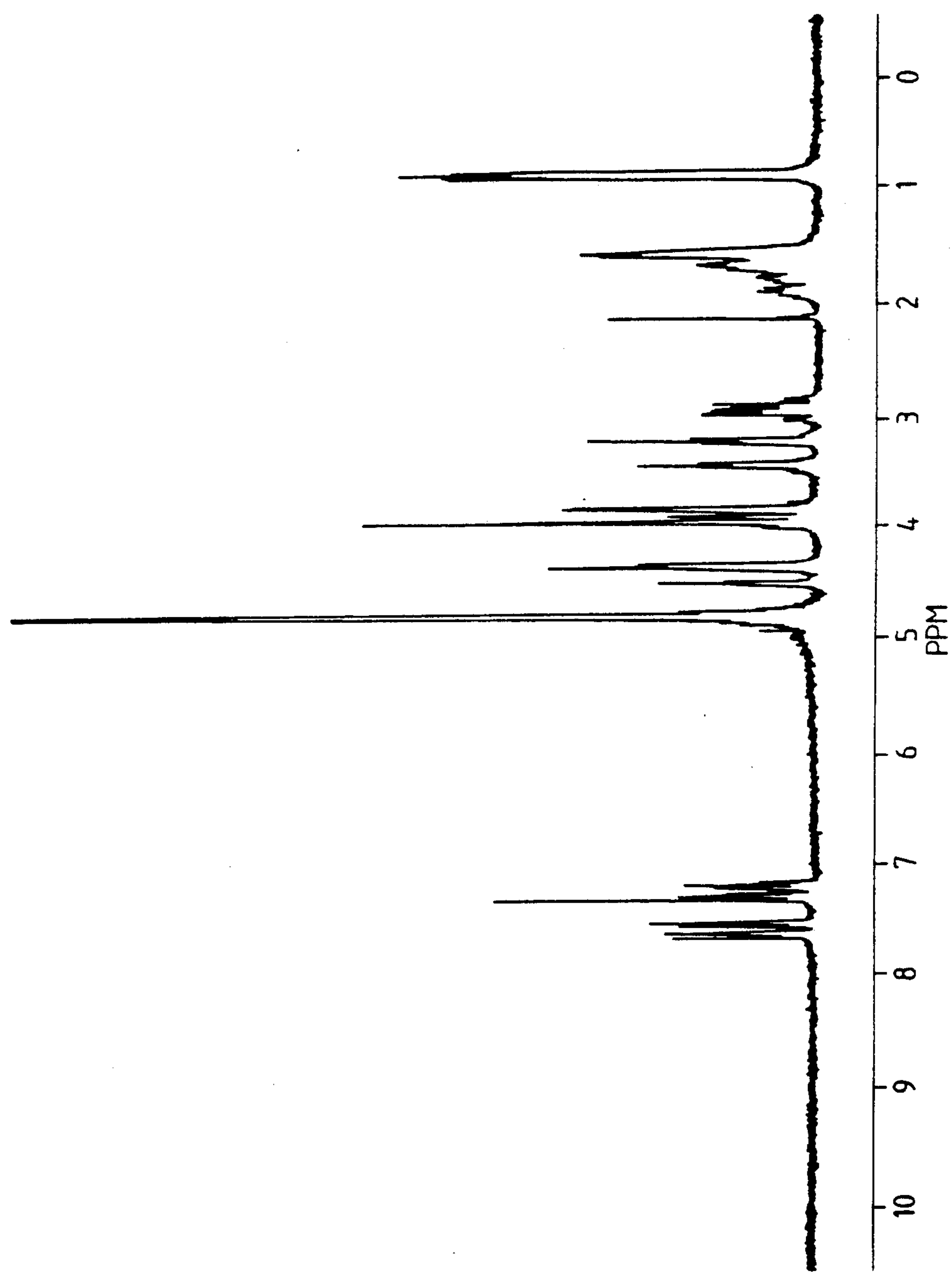
Figure 48:
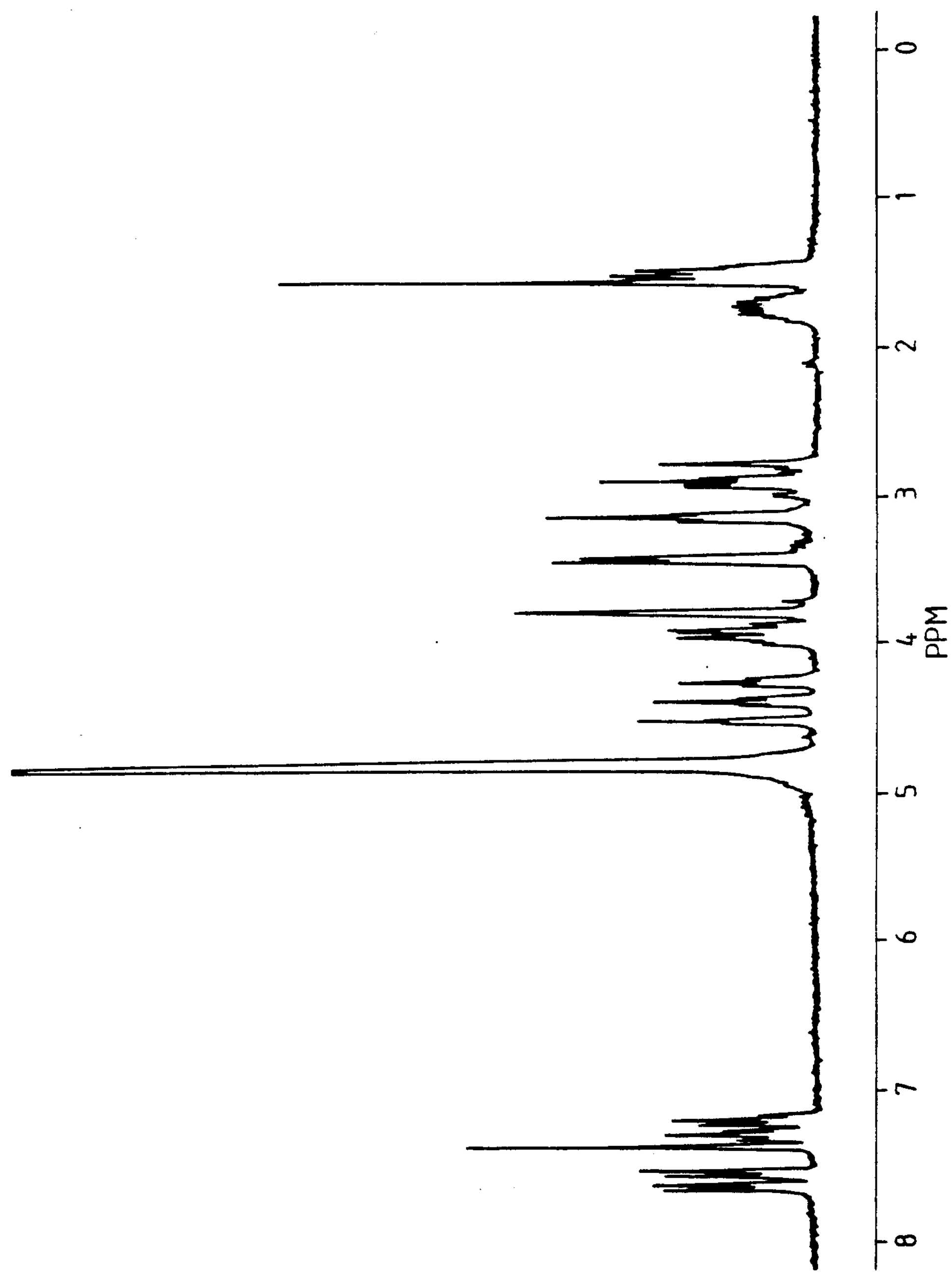
Figure 49:
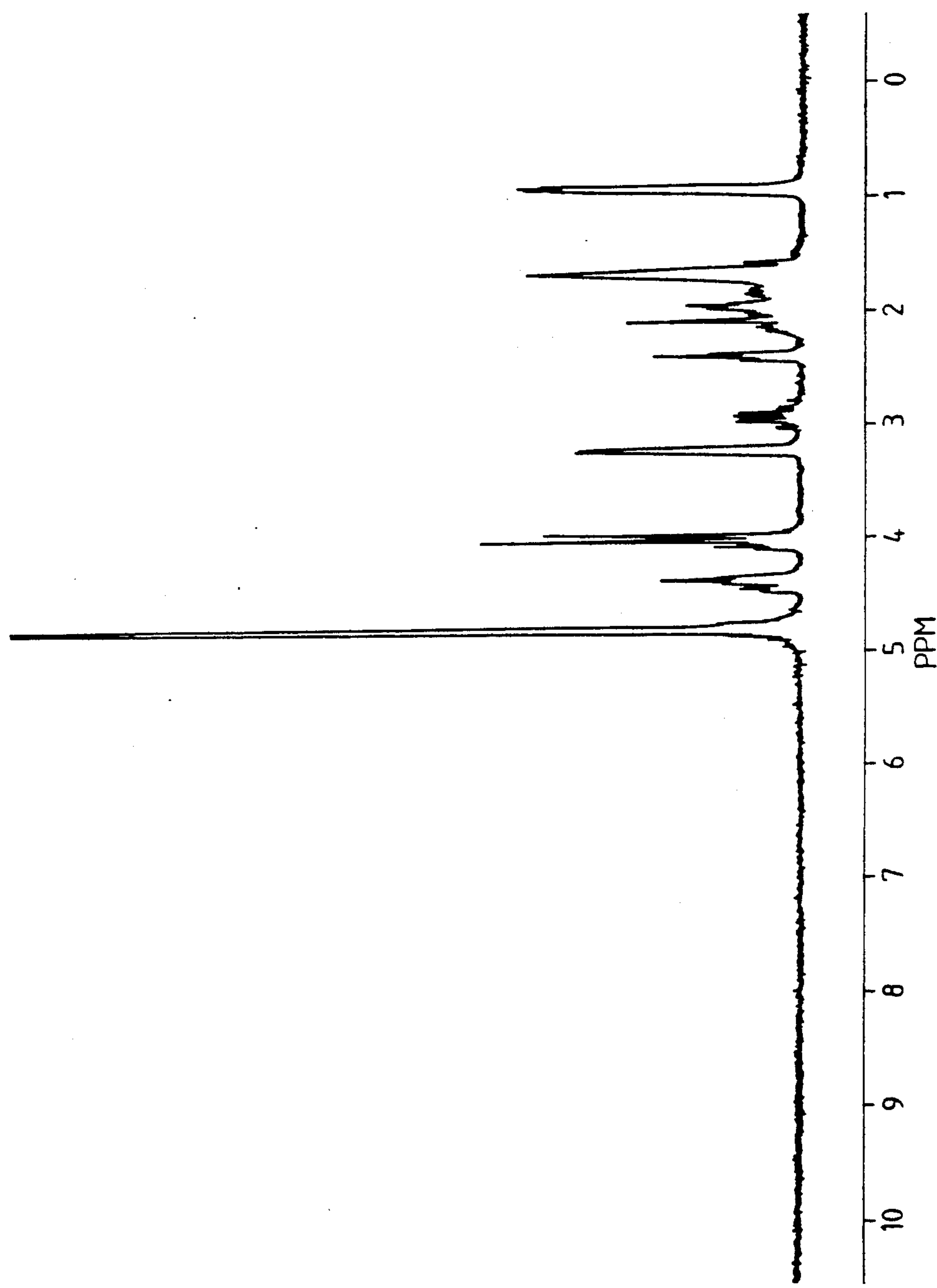
Figure 50:
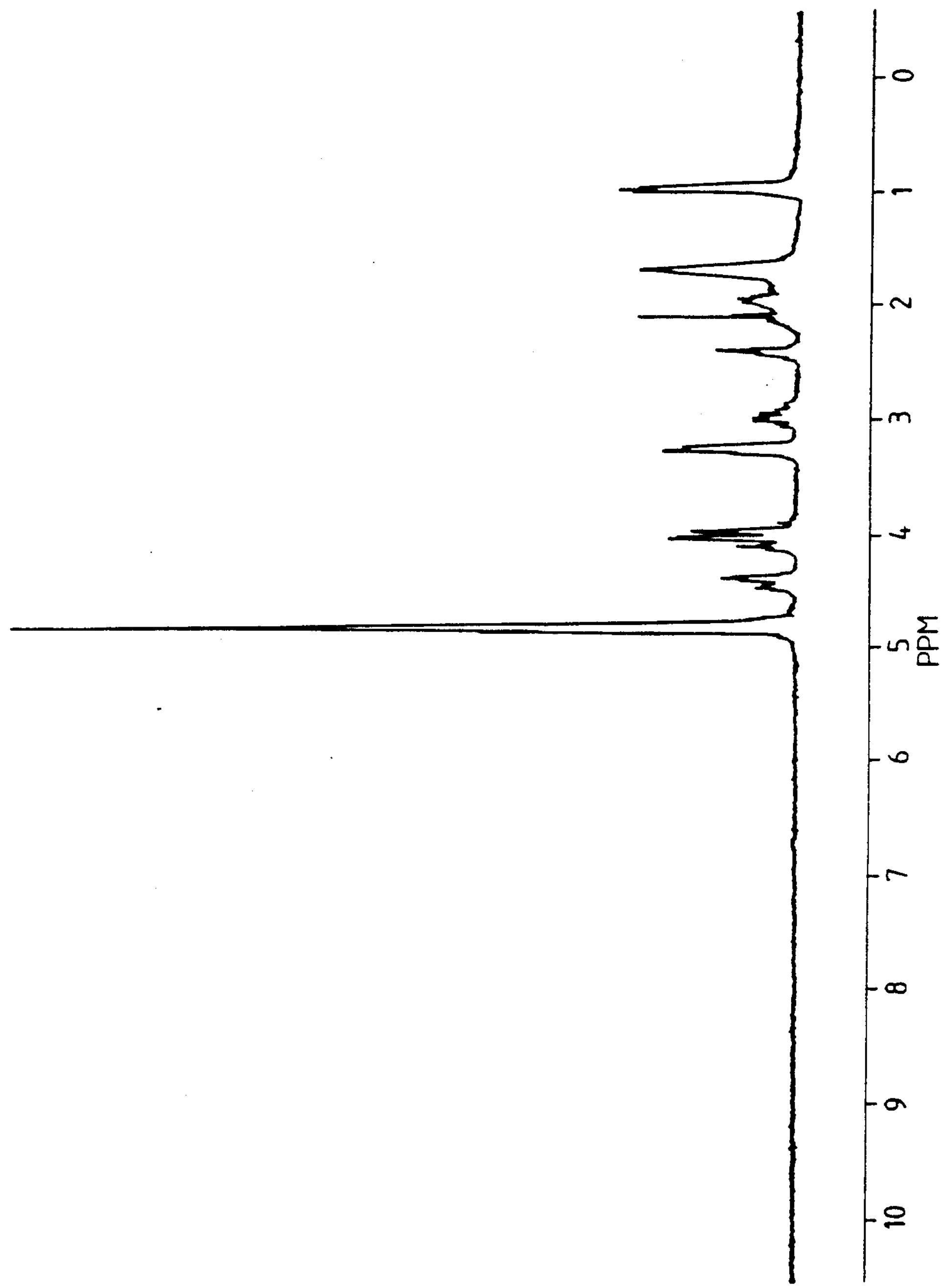
Figure 51:
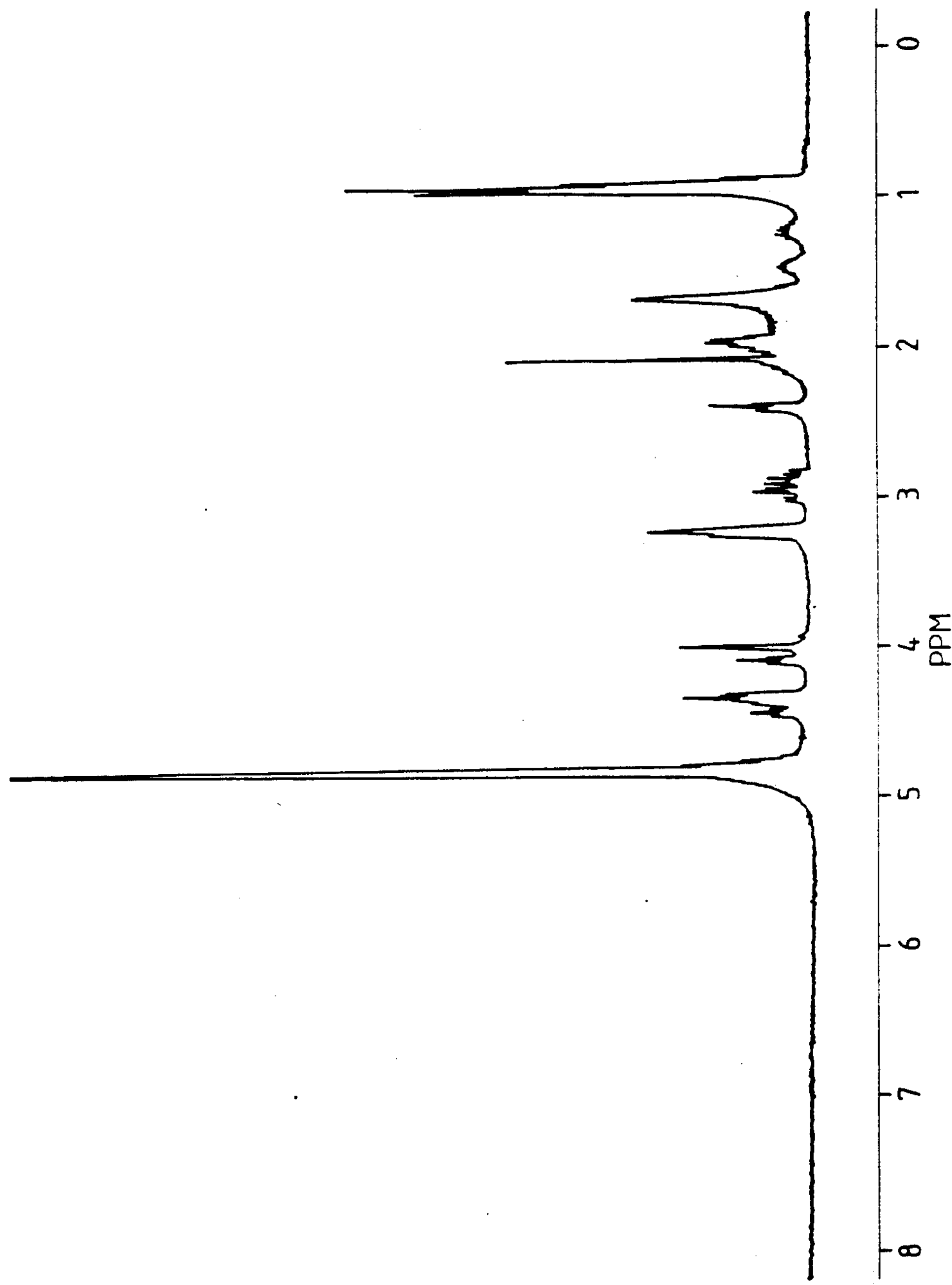
Figure 52:
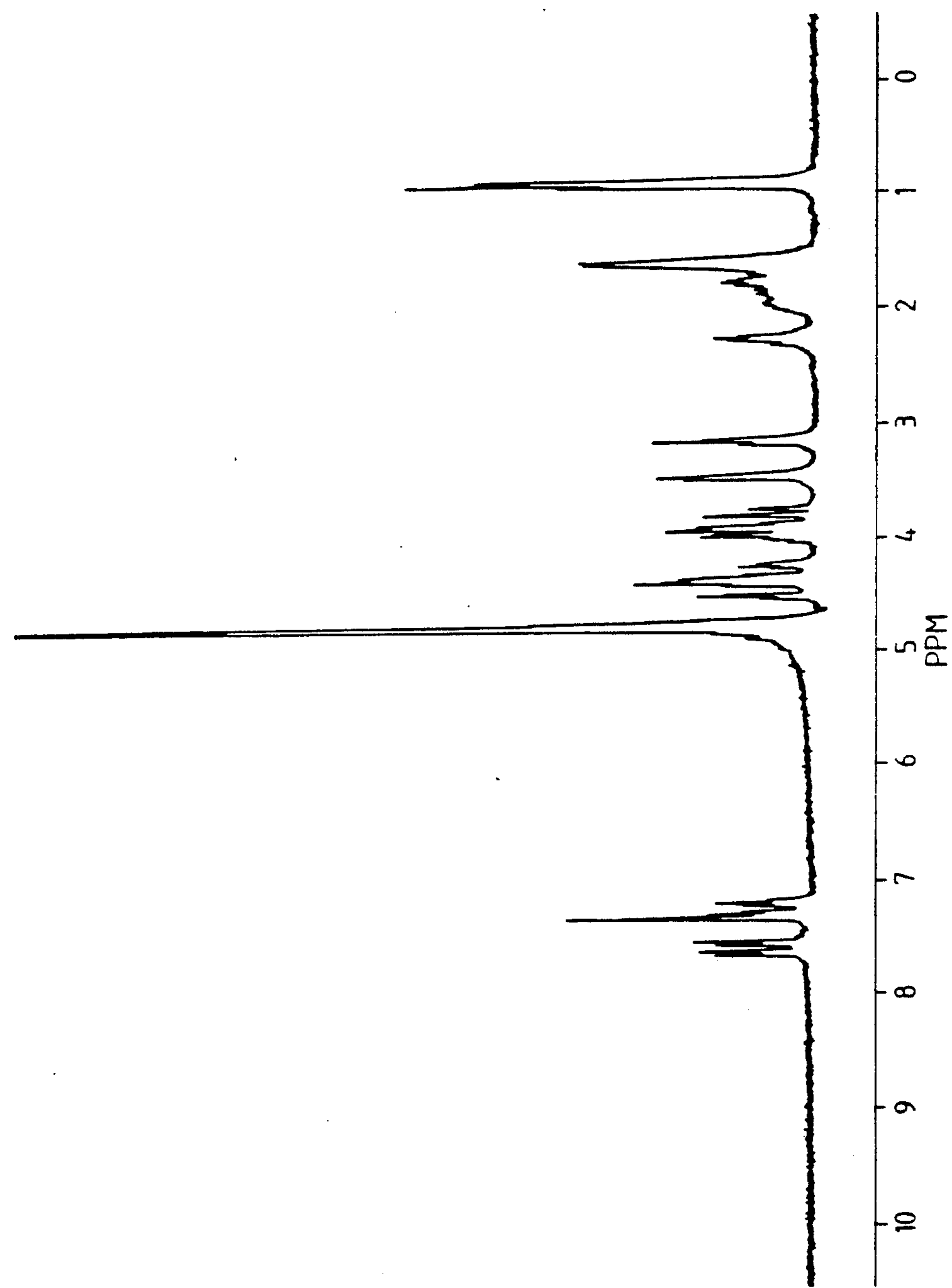
Figure 53:
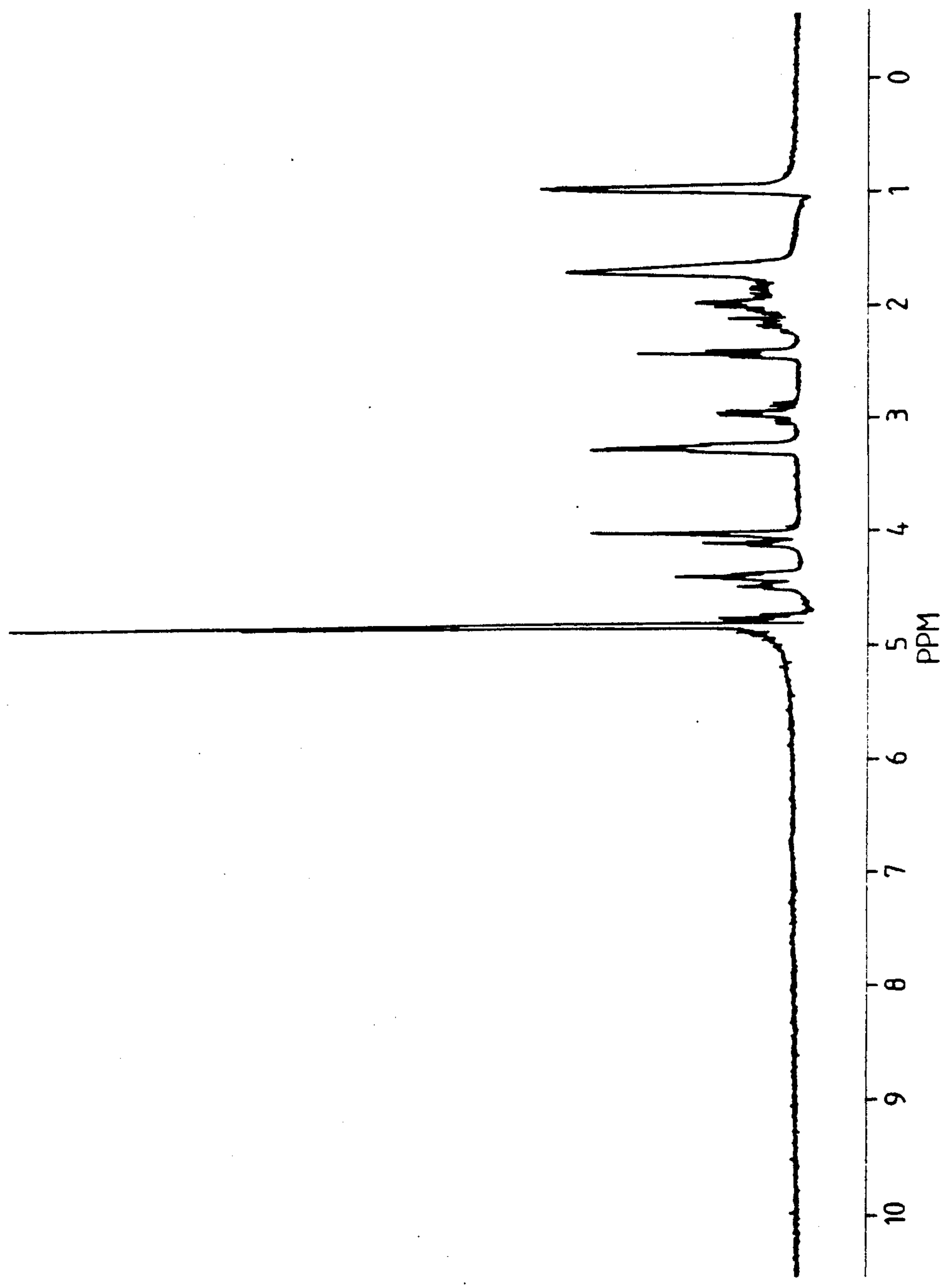
Figure 54:
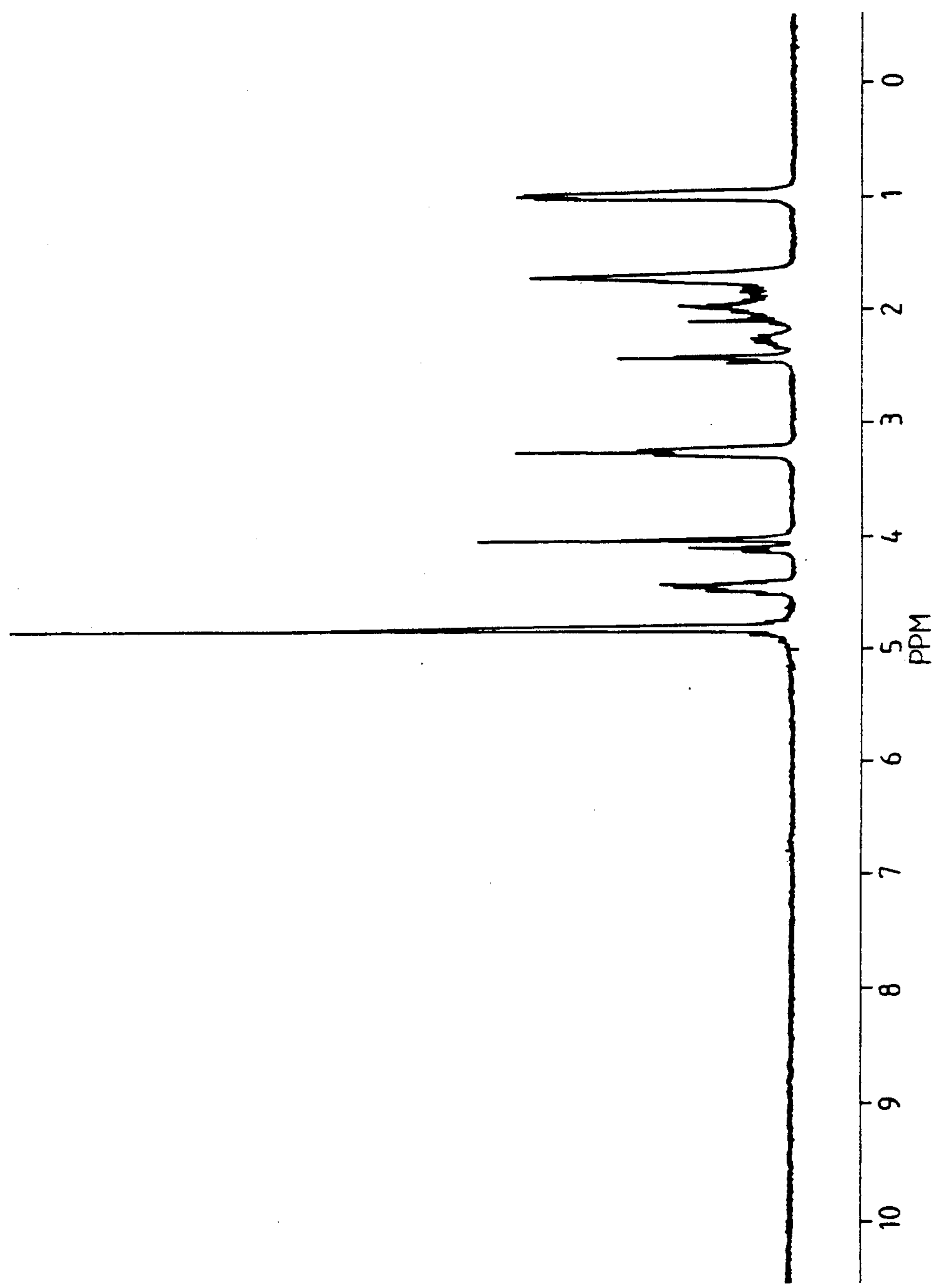
Figure 55:
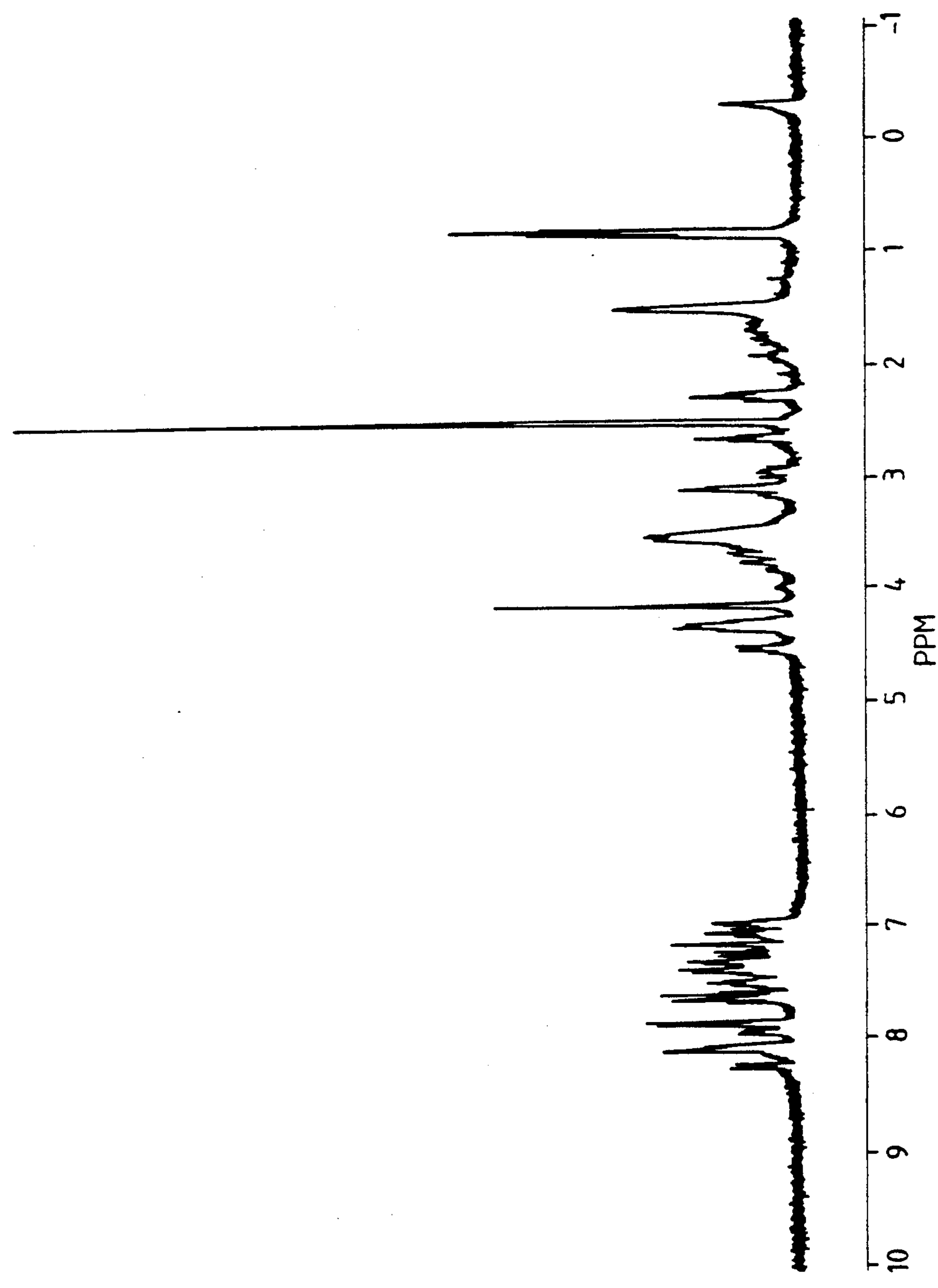
Figure 56:
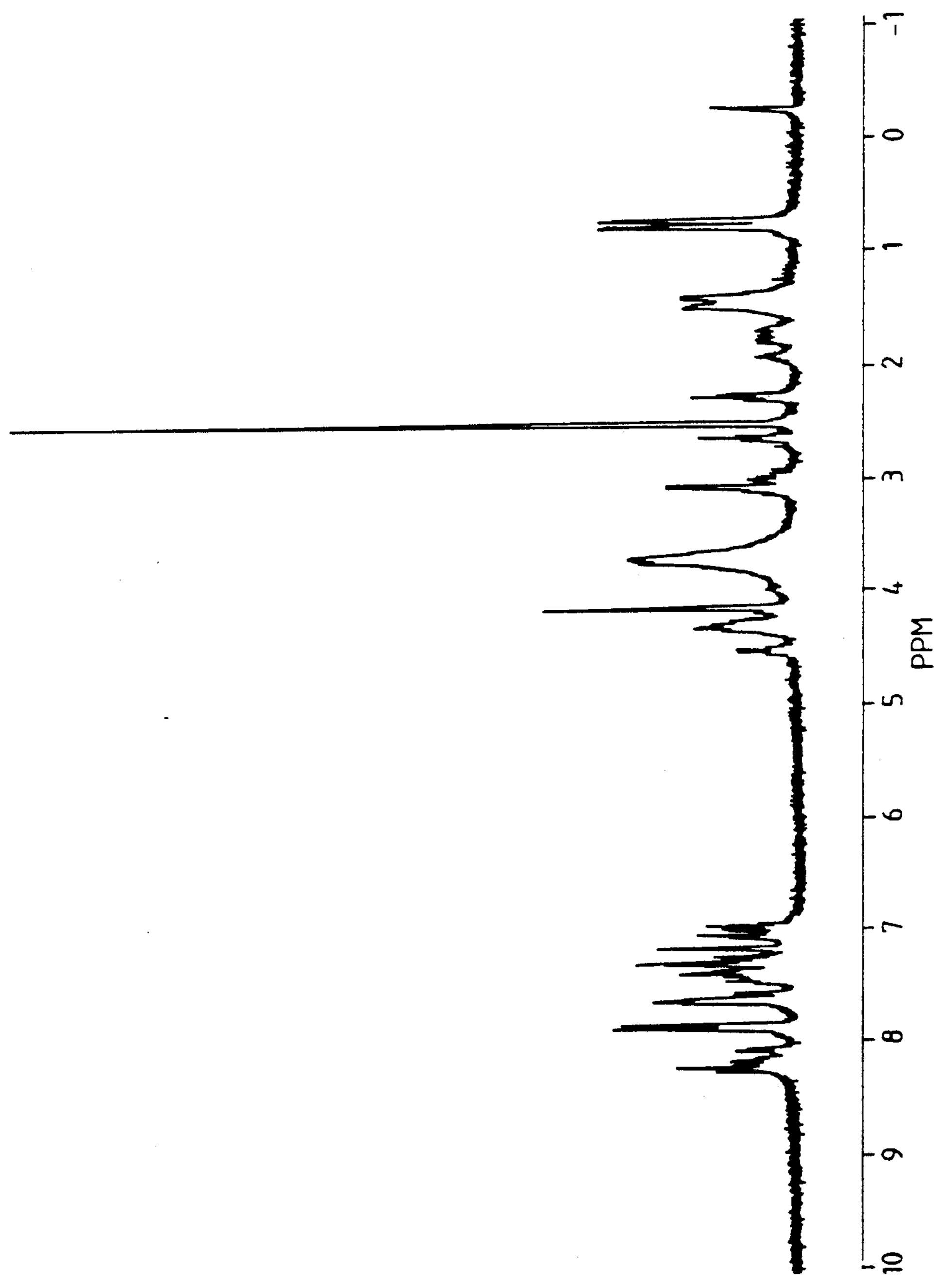
Figure 57:
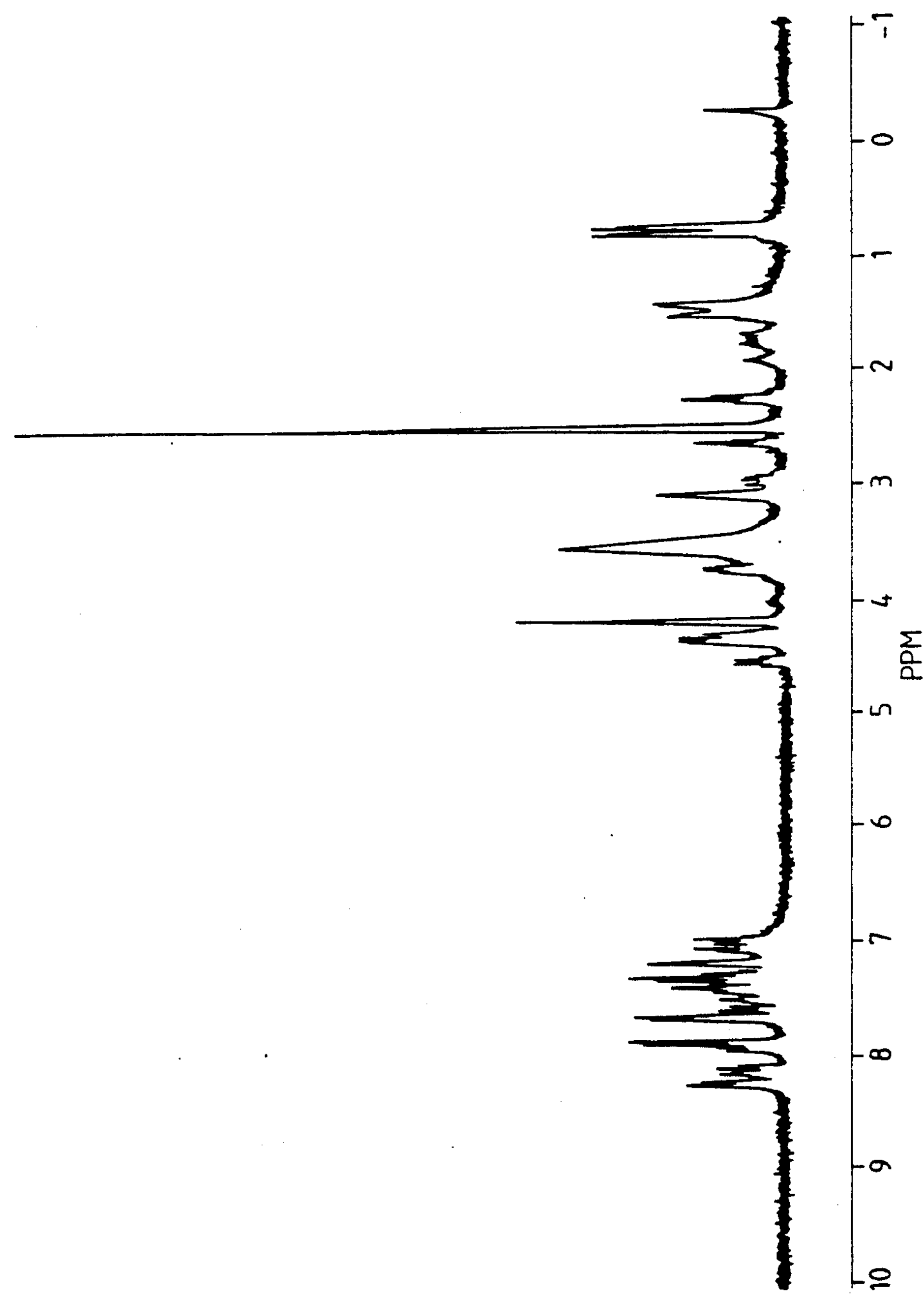
Figure 58:
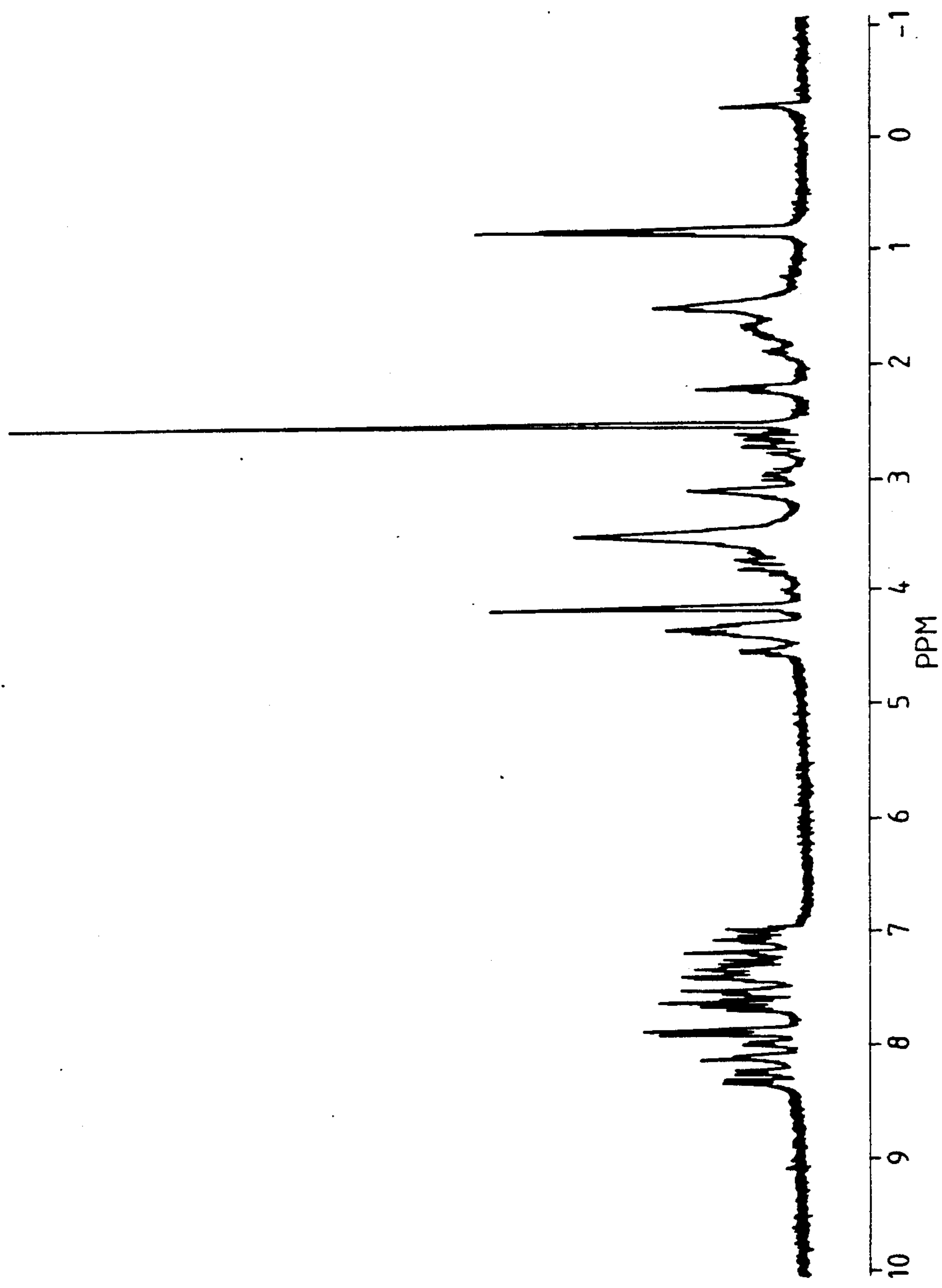
Figure 59:
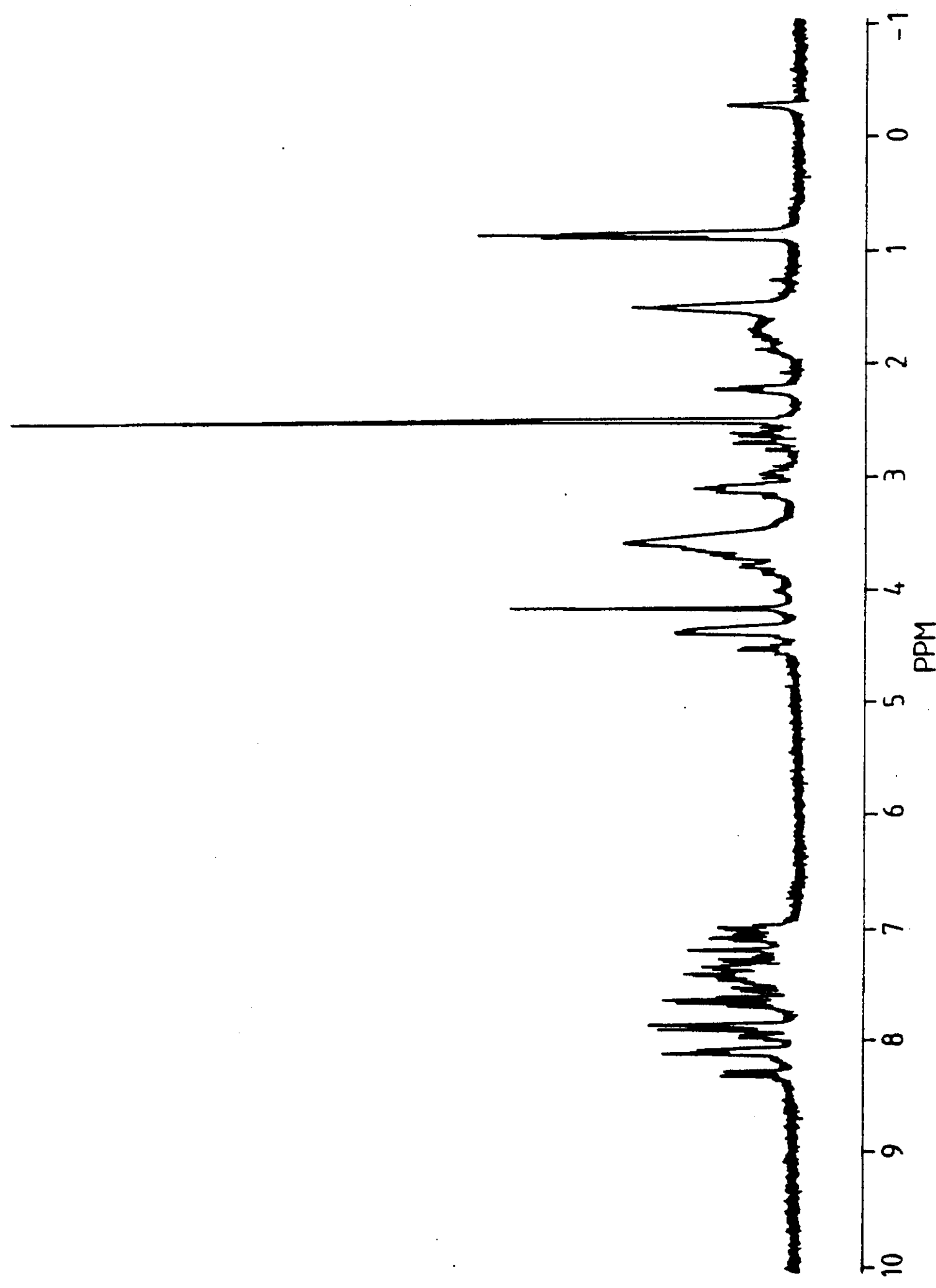
Figure 60:
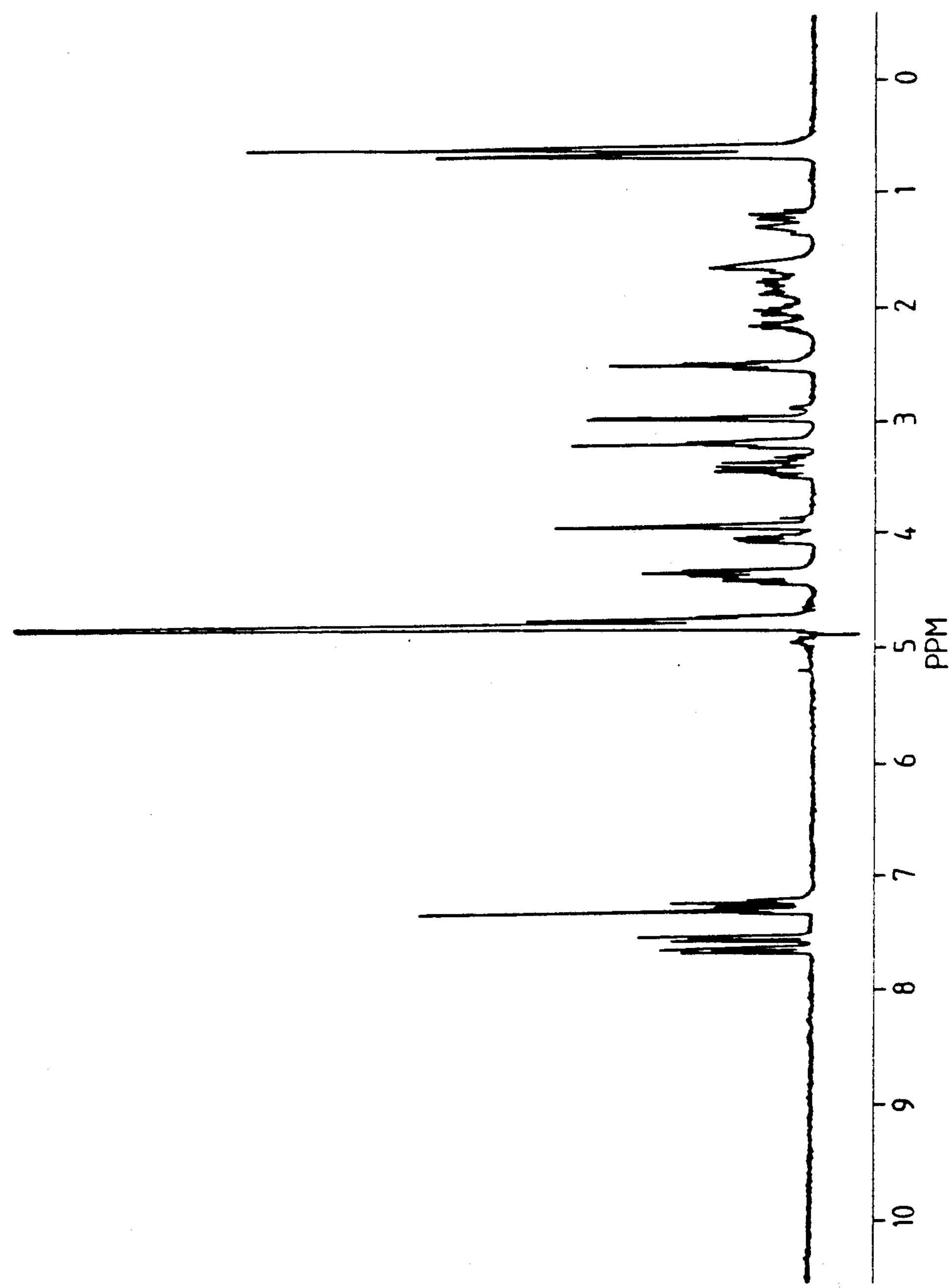
Figure 61:
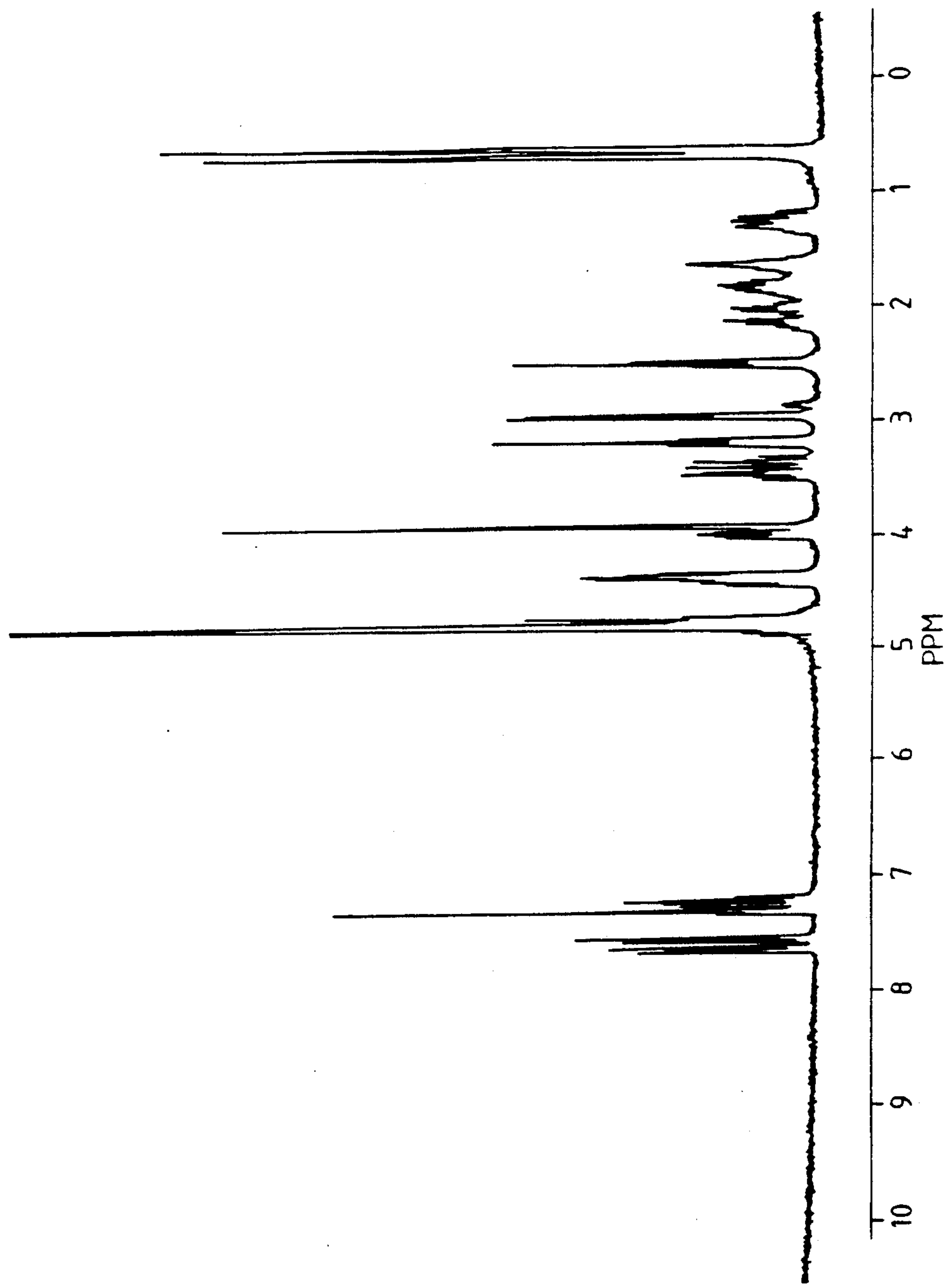
Figure 62:
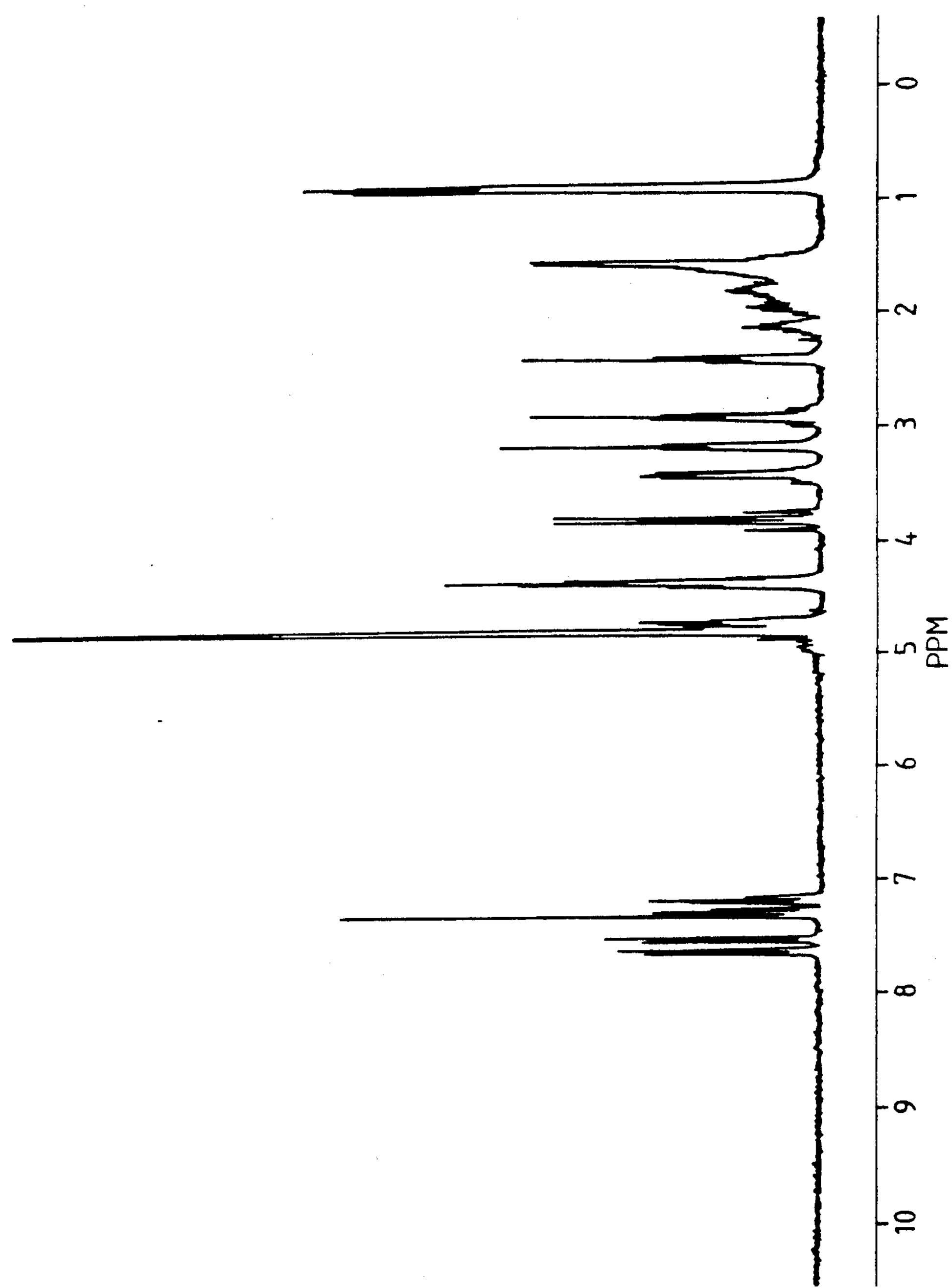
Figure 63:
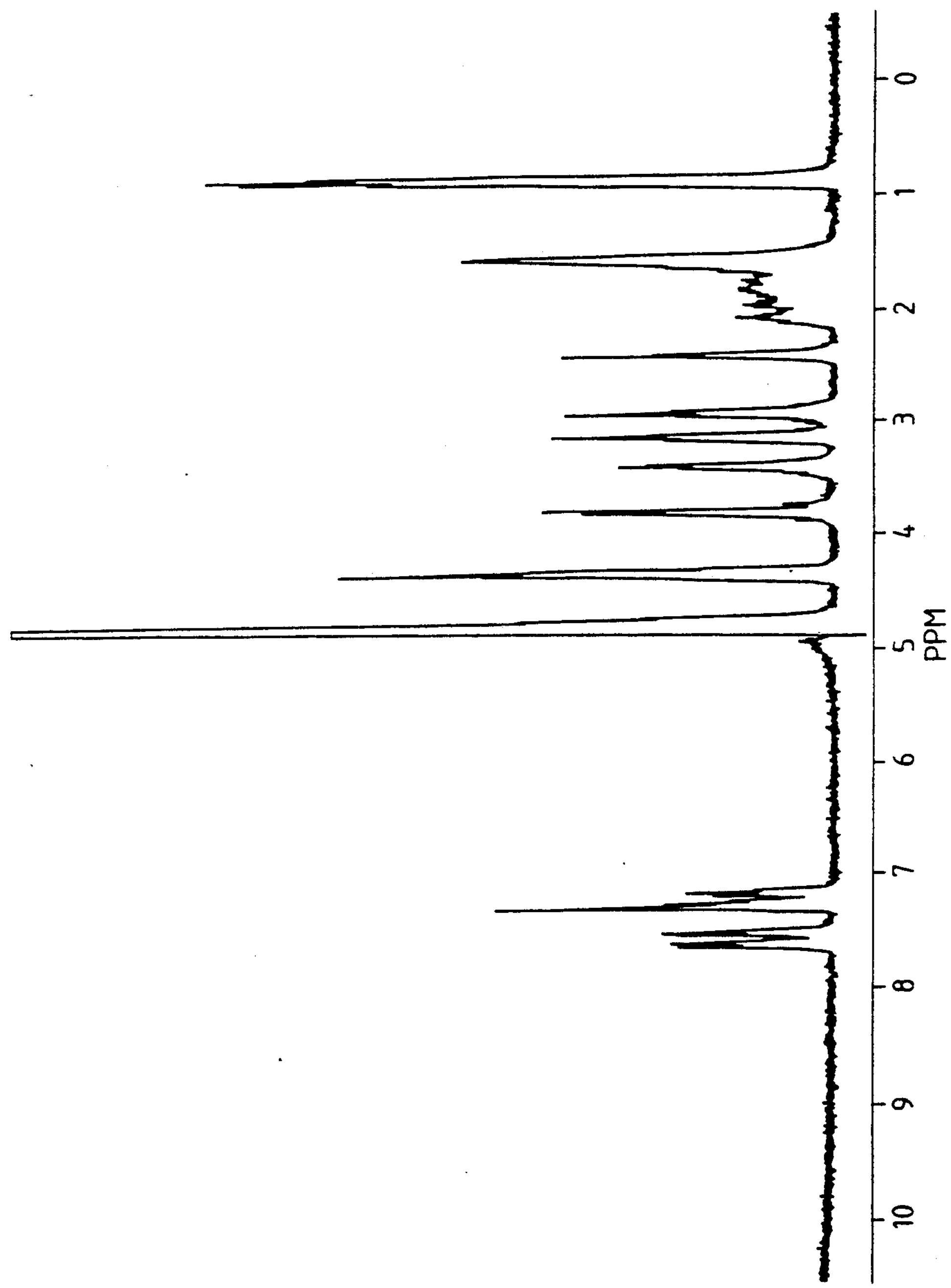

Further, the fraction was applied to reversed phase column ODS-80T (manufactured by Toso Co., Ltd.) which had been equilibrated with 1 mM acetate buffer, pH 5.7. After thoroughly washing, elution was carried out by linearly increasing the concentration of acetonitrile. The state of eluting the peptide was monitored by absorbancy of 215 nm and the activity of the obtained peak was determined, whereby the activity was found in the peak at the elution site of about 25% acetonitrile (which results are shown in FIG. 3). The peptide in this fraction was analyzed with a gaseous phase sequence (Model 477A, manufactured by ABI Company) to be Trp-Leu-Gly-Arg-Glu (or Gln)-Arg-Gly-Ser-Glu or Arg-Leu-Gly-Arg-Glu (or Gln)-Asp-Gly-Ser-Glu.

The results of the amino acid analysis reveal that X is all Glu or Gln.

Symbols for amino acids are as follows.

| Amino Acid | Abbreviation |
|---|---|
| L-alanine | Ala |
| L-arginine | Arg |
| L-asparagine | Asn |
| L-aspartic acid | Asp |
| L-cystein | Cys |
| L-glutamic acid | Glu |
| L-glutamine | Gln |
| Glycine | Gly |
| L-histidine | His |
| L-isoleucine | Ile |
| L-leucine | Leu |
| L-lysine | Lys |
| L-methionine | Met |
| L-phenylalanine | Phe |
| L-proline | Pro |
| L-serine | Ser |
| L-threonine | Thr |
| L-tryptophan | Trp |
| L-tyrosine | Tyr |
| L-valine | Val |

Example 3 shows synthesis of an intermediate. Examples 4 through 63 syntheses of the peptides of the present invention according to the solid phase synthesis method using an automated peptide synthesizer (Model 430A, manufactured by ABI Company), together with physical properties (retention time in HPLC) and spectra of proton-NMR.

After purification of the peptides of the present invention or after removal of protective groups followed by purification, their sequences were confirmed with a protein sequencer (Model 477A, manufactured by ABI Company).

EXAMPLE 3

Fmoc-D-Nle-OH

D-Nle-OH (1.01 g) was dissolved in 30 ml of 10% $NaCO_3$ and 10 ml of dioxan. While stirring, a solution of Fmoc-Cl (2.0 g) in 10 ml of dioxan was added to the solution. After stirring at room temperature for 2 hours, 400 ml of water was added to the mixture. The reaction mixture was extracted twice with 200 ml of ether to remove by-products. Ice was added to the aqueous phase and the mixture was neutralized with conc. hydrochloric acid. After extracting with ethyl acetate, the extract was washed with water. Crystallization from ether gave 933 mg of Fmoc-D-Nle-OH.

EXAMPLE 4

H-L-Trp-L-Leu-Gly-L-Arg-L-Glu-L-Asp-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (20×250), manufactured by Yamamura Chemical Co., Ltd.

Moving phase: A: water (0.1% TFA)
B: acetonitrile (0.1% TFA)
Linear gradient of A:B=100:0 to 10:90 (60 minutes)
Flow rate: 7 ml/min The retention time of the peptide was 21.3 minutes. Yielded amount, 212 mg; yield, 40.5%.

EXAMPLE 5

H-L-Trp-L-Leu-Gly-L-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 25.3 minutes. Yielded amount, 187 mg; yield, 35.7%.

EXAMPLE 6

H-L-Trp-L-Leu-Gly-L-Arg-L-Gln-L-Asp-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 22.0 minutes. Yielded amount, 194 mg; yield, 37.1%.

EXAMPLE 7

H-L-Lys-L-Trp-L-Leu-Gly-L-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Lys(Boc)-OH
Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 21.7 minutes. Yielded amount, 168 mg; yield, 28.6%.

EXAMPLE 8

H-L-Trp-L-Leu-Gly-L-Arg-L-Glu-L-Asp-Gly-L-Ser-OH

Boc-L-Ser(Bzl)-PAM resin, 0.5 mmol, was used based on L-Ser-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH
Boc-L-Asp(OBzl)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B =95 : 5 to 5 : 95 (60 minutes)

Flow rate: 6 ml/min

The retention time of the peptide was 23.9 minutes. Yielded amount, 184 mg; yield, 40.0%.

EXAMPLE 9

H-L-Trp-L-Leu-Gly-L-Arg-L-Glu-L-Asp-Gly-L-Ser-L-Asp-OH

Boc-L-Asp(OBzl)-PAM resin, 0.5 mmol, was used based on L-Asp-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (20×250), manufactured by Yamamura Chemical Co., Ltd.

Moving phase: A: water (0.1% TFA)

B: acetonitrile (0.1% TFA)

Linear gradient of A:B =100 : 0 to 10 : 90 (60 minutes)

Flow rate: 7 ml /min

The retention time of the peptide was 21.9 minutes. Yielded amount, 335 mg; yield, 64.0%.

EXAMPLE 10

H-L-Trp-L-Leu-Gly-L-Arg-L-Glu-L-Asn-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH
Boc-L-Asn-OH
Boc-L-Ser(Bzl)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B =95 : 5 to 5 : 95 (60 minutes)

Flow rate: 6 ml/min

The retention time of the peptide was 23.8 minutes. Yielded amount, 355 mg; yield, 67.8%.

EXAMPLE 11

H-L-Trp-L-Leu-L-Ile-L-Arg-L-Glu-L-Asp-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Leu-OH
Boc-L-Ile-OH
Boc-Gly-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 29.4 minutes. Yielded amount, 108 mg; yield, 19.6%.

EXAMPLE 12

H-L-Phe-L-Leu-Gly-L-Arg-L-Glu-L-Asp-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Phe-OH
Boc-L-Leu-OH
Boc-Gly-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 21.9 minutes. Yielded amount, 232 mg; yield, 46.0%.

EXAMPLE 13

H-L-Trp-L-Leu-Gly-L-Arg-L-Glu-L-Asp-Gly-L-Ser-L-Gln-OH

Boc-L-Gln-PAM resin, 0.5 mmol, was used based on L-Gln-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 23.7 minutes. Yielded amount, 261 mg; yield, 50.0%.

EXAMPLE 14

H-L-Trp-L-Leu-Gly-L-Lys-L-Glu-L-Asp-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Lys(Cl-Z)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 23.0 minutes. Yielded amount, 203 mg; yield, 39.8%.

EXAMPLE 15

H-L-Trp-L-Ala-Gly-L-Arg-L-Glu-L-Asp-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Ala-OH
Boc-Gly-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (20×250), manufactured by Yamamura Chemical Co., Ltd.

Moving phase: A: water (0.1% TFA)
B: acetonitrile (0.1% TFA)
Linear gradient of A:B=100 : 0 to 10 : 90 (60 minutes)
Flow rate: 7 ml/min The retention time of the peptide was 19.7 minutes. Yielded amount, 285 mg; yield, 56.7%.

EXAMPLE 16

H-L-Trp-L-Leu-Gly-L-Arg-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH

The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 24.8 minutes. Yielded amount, 148 mg; yield, 44.9%.

EXAMPLE 17

H-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-Gly-OH
Fmoc-L-Glu(OtBu)-OH
Fmoc-L-Asp(OtBu)-OH
Fmoc-L-Ser(tBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 13.8 minutes. Yielded amount, 163 mg; yield, 60.7%.

EXAMPLE 18

H-L-Trp-L-Pro-L-Arg-L-Glu-L-Asp-Gly-L-Ser-L-Glu-OH

Boc-L-Glu(OBzl)-PAM resin, 0.5 mmol, was used based on L-Glu-OH and Boc-L-amino acid was sequentially condensed according to the steps for peptide synthesis by the Boc method. Boc reagents used are as follows.

Boc-L-Trp-OH
Boc-L-Pro-OH
Boc-L-Arg(Tos)-OH
Boc-L-Glu(OBzl)-OH
Boc-L-Asp(OBzl)-OH
Boc-L-Ser(Bzl)-OH

The peptide was purified by HPLC. The conditions are as follows.

ODS Column (20×250), manufactured by Yamamura Chemical Co., Ltd.

Moving phase: A: water (0.1% TFA)

B: acetonitrile (0.1% TFA)

Linear gradient of A:B=100 : 0 to 10 : 90 (60 minutes)

Flow rate: 7 ml/min

The retention time of the peptide was 28.1 minutes. Yielded amount, 122 mg; yield, 25.0%.

EXAMPLE 19

H-L-Trp-L-Leu-Gly-L-Arg-L-Glu-L-Asp-Gly-OH

Boc-L-Gly-PAM resin, 0.5 mmol, was used based on L-Gly-OH and Boo-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH
Boc-L-Asp(OBzl)-OH

The peptide was purified by HPLC. The conditions are as follows.

ODS Column (20×250), manufactured by Yamamura Chemical Co., Ltd.

Moving phase: A: water (0.1% TFA)

B: acetonitrile (0.1% TFA)

Linear gradient of A:B =100 : 0 to 10 : 90 (60 minutes)

Flow rate: 7 ml/min

The retention time of the peptide was 27.5 minutes. Yielded amount, 107 mg; yield, 25.7%.

EXAMPLE 20

H-L-Trp-L-Leu-Gly-L-Arg-L-Glu-L-Asp-OH

Boc-L-Asp(OBzl)-PAM resin, 0.5 mmol, was used based on L-Asp-OH and Boc-L-amino acid was sequentially condensed according to the steps for peptide synthesis by the Boc method. Boc reagents used are as follows.

Boc-L-Trp-OH
Boc-L-Leu-OH
Boc-Gly-OH
Boc-L-Arg(Tos)-OH
Boc-L-Glu(OBzl)-OH

The peptide was purified by HPLC. The conditions are as follows.

ODS Column (20×250), manufactured by Yamamura Chemical Co., Ltd.

Moving phase: A: water (0.1% TFA)

B: acetonitrile (0.1% TFA)

Linear gradient of A:B=100 : 0 to 10 : 90 (60 minutes)

Flow rate: 7 ml/min

The retention time of the peptide was 24.6 minutes. Yielded amount, 241 mg; yield, 62.2%.

EXAMPLE 21

H-L-Trp-L-Leu-Gly-L-Arg-OH

Boc-L-Arg(Tos)-PAM resin, 0.5 mmol, was used based on L-Arg-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 22.8 minutes. Yielded amount, 52 mg; yield, 19.4%.

EXAMPLE 22

H-L-Trp-L-Leu-Gly-L-Arg-L-Glu-L-Asp-Gly-L-Ser-L-Glu-$NH_2$

BHA resin was used and 0.5 mmol of Fmoc-L-amino acid was used. Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B acetonitrile (0.1% TFA)

Linear gradient of A:B=95 : 5 to 5 : 95 (60 minutes)

Flow rate: 6 ml/min

The retention time of the peptide was 22.3 minutes. Yielded amount, 270 mg; yield, 51.6%.

EXAMPLE 23

H-L-Trp-L-Leu-Gly-L-Arg-L-Gln-L-Asn-Gly-L-Ser-L-Gln-$NH_2$

BHA resin was used and 0.5 mmol of Fmoc-L-amino acid was used. Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Gln-OH
Fmoc-L-Asn-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B =95 : 5 to 5 : 95 (60 minutes)

Flow rate: 6 ml/min

The retention time of the peptide was 20.4 minutes. Yielded amount, 386 mg; yield, 73.9%.

EXAMPLE 24

Fmoc-L-Trp-L-Leu-Gly-L-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows. After condensing with Fmoc-L-Trp-OH, Fmoc group was introduced into the peptide, omitting removal of Fmoc with piperidine.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 38.8 minutes. Yielded amount, 180 mg; yield, 28.4%.

EXAMPLE 25

H-L-Trp-L-Leu-Gly-D-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-D-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B =95 : 5 to 5 : 95 (60 minutes)

Flow rate: 6 ml/min

The retention time of the peptide was 25.0 minutes. Yielded amount, 274 mg; yield, 52.3%.

EXAMPLE 26

H-L-Trp-L-Leu-Gly-L-Arg-L-Glu-L-Asp-Gly-L-Cys-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Cys(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B =95 : 5 to 5 : 95 (60 minutes)

Flow rate: 6 ml/min

The retention time of the peptide was 26.5 minutes. Yielded amount, 199 mg; yield, 37.4%.

EXAMPLE 27

H-L-Trp-D-Nle-Gly-L-Arg-L-Glu-L-Asp-Gly-L-Ser-L-Glu-OH

Boc-L-Glu(OBzl)-PAM resin, 0.5 mmol was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-D-Nle-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 23.7 minutes. Yielded amount, 333 mg; yield, 63.5%.

EXAMPLE 28

H-L-Trp-L-Leu-Gly-L-Arg-L-Glu-L-Asp-Gly-L-Ala-L-Glu-OH

Boc-L-Glu(OBzl)-PAM resin, 0.5 mmol was used based on L-Glu-OH and Boc-L-amino acid was sequentially condensed according to the steps for peptide synthesis by the Boc method. Boc reagents used are as follows.

Boc-L-Trp-OH
Boc-L-Leu-OH .
Boc-Gly-OH
Boc-L-Arg(MIS)-OH
Boc-L-Glu(OBzl)-OH
Boc-L-Asp(OBzl)-OH
Boc-L-Ala-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B =95 : 5 to 5 : 95 (60 minutes)

Flow rate: 6 ml/min

The retention time of the peptide was 15.7 minutes. Yielded amount, 266 mg: Yield, 51.5%.

EXAMPLE 29

H-L-Trp-L-Leu-Gly-L-Tyr-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Tyr(Br-Z)-OH
Fmoc-L-Glu(OtBu)-OH
Fmoc-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 24.6 minutes. Yielded amount, 307 mg; yield, 58.2%.

EXAMPLE 30

H-D-Trp-L-Leu-Gly-L-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-D-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 23.6 minutes. Yielded amount, 268 mg; yield, 51.1%.

EXAMPLE 31

H-L-Trp-L-Leu-Gly-L-Arg-L-Glu-L-Asp-$NH_2$

BHA resin was used and 0.5 mmol of Fmoc-Lamino acid was used. Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH The peptide was purified by HPLC. The conditions are as follows.

ODS Column (19×300), manufactured by Waters Company

Moving phase: A: water (0.1% TFA)

B: acetonitrile (0.1%.TFA)

Linear gradient of A:B=95 : 5 to 5 : 95 (60 minutes)

Flow rate: 6 ml/min

The retention time of the peptide was 25.2 minutes. Yielded amount, 152 mg; yield, 39.3%.

EXAMPLE 32

H-L-Trp-L-Leu-Gly-L-Arg-L-Glu-L-Asp-Gly-D-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-D-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 24.9 minutes. Yielded amount, 405 mg; yield, 77.3%.

EXAMPLE 33

H-L-Trp-D-Leu-Gly-L-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-D-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)
B acetonitrile (0.1% TFA)
Linear gradient of A:B=95 : 5 to 5 : 95 (60 minutes)
Flow rate: 6 ml/min The retention time of the peptide was 28.6 minutes. Yielded amount, 288 mg; yield, 55.0%.

EXAMPLE 34

H-L-Trp-L-Leu-Gly-L-Arg-L-Glu-L-Glu-Gly-L-Ser-OH

Boc-L-Ser(tBu)-PAM resin, 0.5 mmol, was used based on L-Ser-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH

The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 25.0 minutes. Yielded amount, 152 mg; yield, 32.6%.

EXAMPLE 35

H-L-Trp-L-Leu-Gly-L-Arg-D-Glu-L-Asp-Gly-L-Ser-L-Glu-OH

Boc-L-Glu(OBzl)-PAM resin, 0.5 mmol was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-D-Arg(Mtr)-OH
Fmoc-D-Glu(OtBu)-OH
Fmoc-L-Asp(OtBu)-OH
Fmoc-L-Ser(tBu)-OH The peptide was purified by HPLC. The conditions are ODS Column (19×300), manufactured by Waters Company Moving phase: A: water (0.1% TFA)
B acetonitrile (0.1% TFA)
Linear gradient of A:B=95 : 5 to 5 : 95 (60 minutes)
Flow rate: 6 ml/min The retention time of the peptide was 24.3 minutes. Yielded amount, 180 mg; yield, 36.0%.

EXAMPLE 36

H-L-Trp-L-Ala-Gly-L-Arg-L-Glu-L-Asp-OH

Boc-L-Asp(OBzl)-PAM resin, 0.5 mmol, was used based on L-Asp-OH and Fmoc-L-amino acid was sequentially condensed according to the steps for peptide synthesis by the Fmoc method. Fmoc reagents used are as follows.

Fmoc-L-Trp-OH
Fmoc-L-Ala-OH
Fmoc-Gly-OH
Fmoc-L-Arg(Mtr)-OH
Fmoc-L-Glu(OtBu)-OH

The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 21.0 minutes. Yielded amount, 77 mg; yield, 21.0%.

EXAMPLE 37

H-L-Trp-L-Ile-L-Ile-L-Arg-L-Glu-L-Asp-Gly-L-Ser-L-Glu-OH

Boc-L-Glu(OBzl)-PAM resin, 0.5 mmol was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Ile-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B =95 : 5 to 5 : 95 (60 minutes)
Flow rate: 6 ml/min The retention time of the peptide was 26.8 minutes. Yielded amount, 326 mg; yield, 59.1%.

EXAMPLE 38

H-L-Trp-L-Ala-Gly-L-Arg-L-Glu-L-Asp-Gly-L-Ser-L-Glu-$NH_2$

BHA resin was used and 0.5 mmol of Fmoc-L-amino acid was used. Fmoc-L-amino acid was sequentially condensed according to the steps for peptide synthesis by the Fmoc method. Fmoc reagents used are as follows.

Fmoc-L-Trp-OH
Fmoc-L-Ala-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B =95 : 5 to 5 : 95 (60 minutes)
Flow rate: 6 ml/min The retention time of the peptide was 20.4 minutes. Yielded amount, 159 mg; yield, 31.6%.

EXAMPLE 39

H-L-Trp-L-Ala-Gly-L-His-L-Glu-L-Asp-Gly-L-Ser-L-Glu-OH

Boc-L-Glu(OBzl)-PAM resin, 0.5 mmol was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-A-Ala-OH
Fmoc-Gly-OH
Fmoc-L-His(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 20.7 minutes. Yielded amount, 100 mg; yield, 20.3%.

EXAMPLE 40

H-L-Trp-L-Leu-Gly-L-Arg-L-Glu-L-Asp-Gly-L-Leu-L-Leu-$NH_2$

BHA resin was used and 0.5 mmol of Fmoc-L-amino acid was used. Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Leu-OH The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 30.8 minutes. Yielded amount, 102 mg; yield, 19.3%.

EXAMPLE 41

H-L-Met-L-Trp-L-Leu-Gly-L-Arg-L-Glu-L-Asp-OH

Boc-L-Asp(OBzl)-PAM resin, 0.5 mmol, was used based on L-Asp-OH and Fmoc-L-amino acid was sequentially condensed according to the steps for peptide synthesis by the Fmoc method. Fmoc reagents used are as follows.

Fmoc-L-Met-OH
Fmoc-L-Trp-OH
Fmoc-L-Leu-OH
Fmoc-Gly-OH
Fmoc-L-Arg(Mtr)-OH
Fmoc-L-Glu(OtBu)-OH The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 27.6 minutes. Yielded amount, 210 mg; yield, 46.4%.

EXAMPLE 42

H-L-Trp-L-Leu-Gly-L-Arg-Gly-L-Asp-Gly-L-Ser-L-Glu-OH

Boc-L-Glu(OBzl)-PAM resin, 0.5 mmol was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)
B: acetonitrile (0.1% TFA)
Linear gradient of A:B=95 : 5 to 5 : 95 (60 minutes)
Flow rate: 6 ml/min The retention time of the peptide was 24.8 minutes. Yielded amount, 182 mg; yield, 37.3%.

EXAMPLE 43

H-L-Trp-L-Leu-Gly-L-Leu-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Glu(OtBu)-OH

Fmoc-L-Asp(OtBu)-OH
Fmoc-L-Ser(tBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 30.0 minutes. Yielded amount, 317 mg; yield, 63.1%.

EXAMPLE 44

H-L-Trp-L-Val-L-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows.

Fmoc-L-Trp-OH
Fmoc-L-Val-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 21.7 minutes. Yielded amount, 323 mg; yield, 66.1%.

EXAMPLE 45

H-L-Leu-Gly-L-Arg-L-Glu-L-Asp-Gly-L-Ser-L-Glu-OH

Boc-L-Glu(OBzl)-PAM resin, 0.5 mmol was used based on L-Glu-OH and Fmoc-L-amino acid was sequentially condensed according to the steps for peptide synthesis by the Fmoc method. Fmoc reagents used are as follows.

Fmoc-L-Leu-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 18.4 minutes. Yielded amount, 220 mg; yield, 51.1%.

EXAMPLE 46

H-L-Trp-Gly-Gly-L-Arg-L-Glu-L-Asp-Gly-L-Ser-L-Glu-OH

Boc-L-Glu(OBzl)-PAM resin, 0.5 mmol, was used based on L-Glu-OH and Fmoc-L-amino acid was sequentially condensed according to the steps for peptide synthesis by the Fmoc method. Fmoc reagents used are as follows. '

Fmoc-L-Trp-OH
Fmoc-Gly-OH
Fmoc-L-Arg(Mtr)-OH
Fmoc-L-Glu(OtBu)-OH
Fmoc-L-Asp(OtBu)-OH
Fmoc-L-Ser(tBu)-OH The peptide was purified by HPLC. The conditions are as follows.

ODS Column (19×300), manufactured by Waters Company

Moving phase: A: water (0.1% TFA)

B acetonitrile (0.1% TFA)

Linear gradient of A:B=95 : 5 to 5 : 95 (60 minutes)

Flow rate: 6 ml/min

The retention time of the peptide was 21.6 minutes. Yielded amount, 147 mg; yield, 29.6%.

EXAMPLE 47

H-L-Trp-L-Leu-Gly-L-Arg-Gly-L-Asp-L-Ser-OH

Boc-L-Ser(tBu)-PAM resin, 0.5 mmol, was used based on L-Ser-OH and Fmoc-L-amino acid was sequentially condensed according to the steps for peptide synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Asp(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 23.7 minutes. Yielded amount, 265 mg; yield, 67.1%.

EXAMPLE 48

H-L-Trp-L-Arg-Gly-L-Asp-L-Ser-OH

Boc-L-Ser(tBu)-PAM resin, 0.5 mmol was used based on L-Ser-OH and Fmoc-L-amino acid was sequentially condensed according to the steps for peptide synthesis by the Fmoc method. Fmoc reagents used are as follows.

Fmoc-L-Trp-OH
Fmoc-Gly-OH
Fmoc-L-Arg(Mtr)-OH
Fmoc-L-Asp(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of 95 : 5 to 5 : 95 (60 minutes)

Flow rate: 6 ml/min

The retention time of the peptide was 20.0 minutes. Yielded amount, 50 mg; yield, 16.1%.

EXAMPLE 49

H-L-Arg-L-Leu-Gly-L-Arg-L-Gln-L-Asp-Gly-OH

Boc-L-Gly-PAM resin, 0.5 mmol, was used based on Gly-OH and Fmoc-L-amino acid was sequentially condensed according to the steps for peptide synthesis by the Fmoc method. Fmoc reagents used are as follows.

Fmoc-L-Arg(Mtr)-OH
Fmoc-L-Leu-OH
Fmoc-Gly-OH
Fmoc-L-Gln-OH
Fmoc-L-Asp(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 19.6 minutes. Yielded amount, 260 mg; yield, 65.0%.

EXAMPLE 50

H-L-Arg-L-Leu-Gly-L-Arg-L-Gln-L-Asp-Gly-$NH_2$

BHA resin was used and 0.5 mmol of Fmoc-L-amino acid was used. Fmoc-L-amino acid was sequentially condensed according to the steps for peptide synthesis by the Fmoc method. Fmoc reagents used are as follows.

Fmoc-L-Arg(Mtr)-OH
Fmoc-L-Leu-OH
Fmoc-Gly-OH
Fmoc-L-Gln-OH
Fmoc-L-Asp(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 18.8 minutes. Yielded amount, 240 mg; yield, 60.0%.

EXAMPLE 51

H-L-Arg-L-Leu-Gly-L-Arg-L-Gln-L-Asp-L-Lys-OH

Boc-L-Lys(Cl-Z)-PAM resin, 0.5 mmol, was used based on L-Lys-OH and Fmoc-L-amino acid was sequentially condensed according to the steps for peptide synthesis by the Fmoc method. Fmoc reagents used are as follows.

Fmoc-L-Arg(Mtr)-OH
Fmoc-L-Leu-OH
Fmoc-Gly-OH
Fmoc-L-Gln-OH
Fmoc-L-Asp(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 24.3 minutes. Yielded amount, 309 mg; yield, 70.9%.

EXAMPLE 52

H-L-Trp-L-Leu-Gly-L-Gln-L-Arg-L-Ser-OH

Boc-L-Ser(tBu)-PAM resin, 0.5 mmol, was used based on L-Ser-OH and Fmoc-L-amino acid was sequentially condensed according to the steps for peptide synthesis by the Fmoc method. Fmoc reagents used are as follows.

Fmoc-L-Trp-OH
Fmoc-L-Arg(Mtr)-OH
Fmoc-L-Leu-OH
Fmoc-Gly-OH
Fmoc-L-Gln-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 22.5 minutes. Yielded amount, 141 mg; yield, 37.8%.

EXAMPLE 53

H-L-Arg-L-Leu-Gly-L-Arg-L-Gln-L-Asp-$NH_2$

BHA resin was used and 0.5 mmol of Fmoc-L-amino acid was used. Fmoc-L-amino acid was sequentially condensed according to the steps for peptide synthesis by the Fmoc method. Fmoc reagents used are as follows.

Fmoc-L-Arg(Mtr)-OH
Fmoc-L-Leu-OH
Fmoc-Gly-OH
Fmoc-L-Gln-OH
Fmoc-L-Asp(OtBu)-OH

The peptide was purified by HPLC. The conditions are as follows.

ODS Column (19×300), manufactured by Waters Company

Moving phase A: water (0.1% TFA)

B: acetonitrile (0.1% TFA)

Linear gradient of A:B=95 : 5 to 5 : 95 (60 minutes)

Flow rate: 6 ml/min

The retention time of the peptide was 18.6 minutes. Yielded amount, 113 mg; yield, 30.4%.

EXAMPLE 54

H-L-Arg-L-Leu-Gly-L-Arg-L-Gln-OH

Boc-L-Gln-PAM resin, 0.5 mmol, was used based on L-Gln-OH and Fmoc-L-amino acid was sequentially condensed according to the steps for peptide synthesis by the Fmoc method. Fmoc reagents used are as follows.

Fmoc-L-Arg(Mtr)-OH
Fmoc-L-Leu-OH
Fmoc-Gly-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 19.0 minutes. Yielded amount, 204 mg; yield, 64.9%.

EXAMPLE 55

Fmoc-L-Trp-L-Leu-Gly-L-Arg-L-Glu-L-Asp-OH

Boc-L-Asp(OBzl)-PAM resin, 0.5 mmol, was used based on L-Asp-OH and Fmoc-L-amino acid was sequentially condensed according to the steps for peptide synthesis by the Fmoc method. Fmoc reagents used are as follows. After condensing with Fmoc-L-Trp-OH, Fmoc group was introduced into the peptide, omitting removal of Fmoc with piperidine.

Fmoc-L-Trp-OH
Fmoc-L-Leu-OH
Fmoc-Gly-OH
Fmoc-L-Arg(Mtr)-OH
Fmoc-L-Glu(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 40.7 minutes. Yielded amount, 162 mg; yield, 32.5%.

EXAMPLE 56

Fmoc-D-Trp-L-Leu-Gly-L-Arg-L-Glu-L-Asp-OH

Boc-L-Asp(OBzl)-PAM resin, 0.5 mmol, was used based on L-Asp-OH and Fmoc-L-amino acid was sequentially condensed according to the steps for peptide synthesis by the Fmoc method. Fmoc reagents used are as follows. After condensing with Fmoc-L-Trp-OH, Fmoc group was introduced into the peptide, omitting removal of Fmoc with piperidine.

Fmoc-D-Trp-OH
Fmoc-L-Leu-OH
Fmoc-Gly-OH
Fmoc-L-Arg(Mtr)-OH
Fmoc-L-Glu(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 46.7 minutes. Yielded amount, 138 mg; yield, 27.7%.

EXAMPLE 57

Fmoc-L-Trp-D-Leu-Gly-L-Arg-L-Glu-L-Asp-OH

Boc-L-Asp(OBzl)-PAM resin, 0.5 mmol, was used based on L-Asp-OH and Fmoc-L-amino acid was sequentially condensed according to the steps for peptide synthesis by the Fmoc method. Fmoc reagents used are as follows. After condensing with Fmoc-L-Trp-OH, Fmoc group was introduced into the peptide, omitting removal of Fmoc with piperidine.

Fmoc-L-Trp-OH
Fmoc-D-Leu-OH
Fmoc-Gly-OH
Fmoc-L-Arg(Mtr)-OH
Fmoc-L-Glu(OtBu)-OH

The peptide was purified by HPLC. The conditions are as follows.

ODS Column (19×300), manufactured Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 43.7 minutes. Yielded amount, 119 mg; yield, 23.9%.

EXAMPLE 58

Fmoc-L-Trp-L-Leu-Gly-L-Arg-D-Glu-L-Asp-OH

Boc-L-Asp(OBzl)-PAM resin, 0.5 mmol, was used based on L-Asp-OH and Fmoc-L-amino acid was sequentially condensed according to the steps for peptide synthesis by the Fmoc method. Fmoc reagents used are as follows. After condensing with Fmoc-L-Trp-OH, Fmoc group was introduced into the peptide, omitting removal of Fmoc with piperidine.

Fmoc-L-Trp-OH
Fmoc-L-Leu-OH
Fmoc-Gly-OH
Fmoc-L-Arg(Mtr)-OH
Fmoc-D-Glu(OtBu)-OH

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 44.3 minutes. Yielded amount, 178 mg; yield, 35.7%.

EXAMPLE 59

Fmoc-L-Trp-L-Leu-Gly-L-Arg-L-Glu-D-Asp-OH

HMP resin was used and 0.5 mmol of Fmoc-amino acid was used. Fmoc-amino acid was sequentially condensed according to the steps for peptide, synthesis by the Fmoc method. Fmoc reagents used are as follows.

Fmoc-L-Trp-OH
Fmoc-L-Leu-OH
Fmoc-Gly-OH
Fmoc-L-Arg(Mtr)-OH
Fmoc-L-Glu(OtBu)-OH
Fmoc-D-Asp(OtBu)-OH The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 44.4 minutes. Yielded amount, 180 mg; yield, 36.0%.

EXAMPLE 60

H-D-Trp-L-Leu-Gly-L-Arg-L-Glu-L-Asp-OH

Fmoc-D-Trp-L-Leu-Gly-L-Arg-L-Glu-L-Asp-OH (50 mg), was dissolved in 0.5 ml of dimethylsulfoxide and 0.5 ml of piperidine was added to the solution. After reacting for an hour, the reaction mixture was neutralized with acetic acid under cooling.

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 28.7 minutes. Yielded amount, 40 mg; yield, 100%.

EXAMPLE 61

H-L-Trp-D-Leu-Gly-L-Arg-L-Glu-L-Asp-OH

Fmoc-L-Trp-D-Leu-Gly-L-Arg-L-Glu-L-Asp-OH (50 mg), was dissolved in 0.5 ml of dimethylsulfoxide and 0.5 ml of piperidine was added to the solution. After reacting for an hour, the reaction mixture was neutralized with acetic acid under cooling.

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 29.1 minutes. Yielded amount, 37.5 mg; yield, 96.4%.

EXAMPLE 62

H-L-Trp-L-Leu-Gly-L-Arg-D-Glu-L-Asp-OH

Fmoc-L-Trp-L-Leu-Gly-L-Arg-D-Glu-L-Asp-OH (50 mg), was dissolved in 0.5 ml of dimethylsulfoxide and 0.5 ml of piperidine was added to the solution. After reacting for an hour, the reaction mixture was neutralized with acetic acid under cooling.

The peptide was purified by HPLC. The conditions are as follows.

ODS Column (19×300), manufactured by Waters Company

Moving phase A: water (0.1% TFA)

B: acetonitrile (0.1% TFA)

Linear gradient of A:B=95 : 5 to 5 : 95 (60 minutes)

Flow rate: 6 ml/min

The retention time of the peptide was 26.0 minutes. Yielded amount, 36.5 mg; yield, 93.8%.

EXAMPLE 63

H-L-Trp-L-Leu-Gly-L-Arg-D-Glu-L-Asp-OH

Fmoc-L-Trp-L-Leu-Gly-L-Arg-D-Glu-L-Asp-OH (50 mg), was dissolved in 0.5 ml of dimethylsulfoxide and 0.5 ml of piperidine was added to the solution. After reacting for an hour, the reaction mixture was neutralized with acetic acid under cooling.

The peptide was purified by HPLC. The conditions are as follows.

ODS Column (19×300), manufactured by Waters Company

Moving phase: A: water (0.1% TFA)

B: acetonitrile (0.1% TFA)

Linear gradient of A:B=95 : 5 to 5 : 95 (60 minutes)

Flow rate: 6 ml/min

The retention time of the peptide was 26.0 minutes. Yielded amount, 40 mg; yield, 100%.

EXAMPLE 64

The peptide synthesized in Example 5 was dissolved in 5 mM $MgCl_2$ and the solution was suitably diluted with 0.5% FCS-containing Hanks' medium. When macrophage chemotactic activity, was measured high activities were noted. Relative activities determined are shown in Table 1.

TABLE 1

| | Macrophage Chemotactic Activity |
|---|---|
| Culture Supernatant of hybridoma MCF-A51 | 100.0 |
| Medium alone | 10.0 |
| Synthetic peptide, $3 \times 10^{-8}$ M | 41.4 |

The peptide of the present invention showed a high MCF activity even when suspended in a solution containing ions such as $Cu^{++}$, $Zn^{++}$, $Ca^{++}$, $Mn^{++}$, $Sr^{++}$, $Co^{++}$, $Sn^{++}$, $Fe^{+++}$, $Pb^{++}$, etc.

EXAMPLE 65

The compounds of the present invention having a good macrophage chemotaxis showed a macrophage chemotactic activity shown in Table 2 in the test described in Example 64.

TABLE 2

| Compounds Having a Good Macrophage Chemotaxis | | |
|---|---|---|
| Compound No. | Compounds Having a Good Macrophage Chemotaxis | Activity |
| 1. | H—L—Trp—L—Leu—Gly—L—Arg—L—Glu—L—Asp—Gly—L—Ser—L—Glu—OH | 100 |
| 2. | H—L—Trp—L—Leu—Gly—L—Arg—L—Gln—L—Asp—Gly—L—Ser—L—Glu—OH | 80 |
| 3. | H—L—Lys—L—Trp—L—Leu—Gly—L—Arg—L—Glx—L—Asp—Gly—L—Ser—L—Glu—OH | 80 |
| 4. | H—L—Trp—L—Leu—Gly—L—Arg—L—Glx—L—Asp—Gly—L—Ser—L—Asp—OH | 10 |
| 5. | H—L—Trp—L—Leu—Gly—L—Arg—L—Glx—L—Asn—Gly—L—Ser—L—Glu—OH | <10 |
| 6. | H—L—Trp—L—Leu—L—Ile—L—Arg—L—Glx—L—Asp—Gly—L—Ser—L—Glu—OH | <10 |
| 7. | H—L—Phe—L—Leu—Gly—L—Arg—L—Glx—L—Asp—Gly—L—Ser—L—Glu—OH | <10 |
| 8. | H—L—Trp—L—Leu—Gly—L—Lys—L—Glx—L—Asp—Gly—L—Ser—L—Glu—OH | <10 |
| 9. | H—L—Trp—L—Ala—Gly—L—Arg—L—Glx—L—Asp—Gly—L—Ser—L—Glu—OH | <10 |
| 10. | H—L—Trp—L—Pro—L—Arg—L—Glx—L—Asp—Gly—L—Ser—L—Glu—OH | <10 |
| 11. | H—L—Trp—L—Leu—Gly—L—Arg—L—Gln—L—Asn—Gly—L—Ser—L—Gln—$NH_2$ | <10 |
| 12. | H—L—Trp—L—Leu—Gly—L—Arg—L—Glx—L—Asp—Gly—L—Ser—L—Glu—$NH_2$ | <10 |
| 13. | Fmoc—L—Trp—L—Leu—Gly—L—Arg—L—Glx—L—Asp—Gly—L—Ser—L—Glu—OH | <10 |
| 14. | H—L—Trp—L—Leu—Gly—D—Arg—L—Glx—L—Asp—Gly—L—Ser—L—Glu—OH | 80 |
| 15. | H—L—Trp—D—Nle—Gly—L—Arg—L—Glx—L—Asp—Gly—L—Ser—L—Glu—OH | <10 |

TABLE 2-continued

| Compound No. | Compounds Having a Good Macrophage Chemotaxis | Activity |
|---|---|---|
| | Compounds Having a Good Macrophage Chemotaxis | |
| 16. | H—L—Trp—L—Leu—Gly—L—Arg—L—Glx—L—Asp—Gly—L—Ser—L—Glu—OH | <10 |
| 17. | H—L—Trp—L—Leu—Gly—L—Arg—L—Glx—L—Asp—Gly—L—Cys—L—Glu—OH | <10 |
| 18. | H—L—Trp—L—Leu—Gly—L—Tyr—L—Glx—L—Asp—Gly—L—Ser—L—Glu—OH | 50 |
| 19. | H—L—Trp—L—Leu—Gly—L—Gln—L—Arg—L—Ser—OH | |
| 20. | H—L—Trp—L—Leu—Gly—L—Arg—L—Glx—L—Asp—Gly—L—Ala—L—Glu—OH | <10 |
| 21. | H—L—Trp—L—Leu—Gly—L—Arg—L—Glx—L—Asp—Gly—L—Ser—OH | 10 |
| 22. | H—L—Trp—L—Leu—Gly—L—Arg—L—Glx—L—Asp—Gly—OH | <10 |
| 23. | H—L—Trp—L—Leu—Gly—L—Arg—L—Glx—L—Asp—OH | 10 |
| 24. | H—L—Trp—L—Leu—Gly—L—Arg—L—Glx—OH | <10 |
| 25. | H—L—Glx—L—Asp—Gly—L—Ser—L—Glu—OH | <10 |
| 26. | H—L—Trp—L—Leu—Gly—L—Arg—L—Glx—L—Asp—$NH_2$ | 10 |
| 27. | H—L—Trp—L—Leu—Gly—L—Arg—OH | <10 |
| 28. | H—L—Trp—L—Leu—Gly—L—Arg—L—Glx—L—Asp—Gly—L—Ser—L—Gln—OH | <10 |
| 29. | Fmoc—L—Trp—L—Leu—Gly—L—Arg—L—Glx—L—Asp—OH | <10 |
| 30. | Fmoc—D—Trp—L—Leu—Gly—L—Arg—L—Glx—L—Asp—OH | <10 |
| 31. | H—D—Trp—L—Leu—Gly—L—Arg—L—Glx—L—Asp—OH | |
| 32. | Fmoc—L—Trp—D—Leu—Gly—L—Arg—L—Glx—L—Asp—OH | <10 |
| 33. | H—L—Trp—D—Leu—Gly—L—Arg—L—Glx—L—Asp—OH | |
| 34. | Fmoc—L—Trp—L—Leu—Gly—L—Arg—D—Glx—L—Asp—OH | <10 |
| 35. | H—L—Trp—L—Leu—Gly—L—Arg—D—Glx—L—Asp—OH | |
| 36. | H—L—Trp—L—Leu—Gly—L—Arg—L—Glx—L—Asp—Gly—D—Ser—L—Glu—OH | <10 |
| 37. | H—L—Trp—D—Leu—Gly—L—Arg—L—Glx—L—Asp—Gly—L—Ser—L—Glu—OH | <10 |
| 38. | H—L—Trp—L—Leu—Gly—L—Arg—L—Glx—L—Glu—Gly—L—Ser—OH | <10 |
| 39. | Fmoc—L—Trp—L—Leu—Gly—L—Arg—L—Glx—D—Asp—OH | 10 |
| 40. | H—L—Trp—L—Leu—Gly—L—Arg—L—Glx—D—Asp—OH | |
| 41. | H—L—Trp—L—Leu—Gly—L—Arg—D—Glx—L—Asp—Gly—L—Ser—L—Glu—OH | <10 |
| 42. | H—L—Trp—L—Ala—Gly—L—Arg—L—Glx—L—Asp—OH | <10 |
| 43. | H—L—Trp—L—Ile—L—Ile—L—Arg—L—Glx—L—Asp—Gly—L—Ser—L—Glu—OH | <10 |
| 44. | H—L—Trp—L—Ala—Gly—L—Arg—L—Glx—L—Asp—Gly—L—Ser—L—Glu—$NH_2$ | <10 |
| 45. | H—L—Trp—L—Ala—Gly—L—His—L—Glx—L—Asp—Gly—L—Ser—L—Glu—OH | |
| 46. | H—L—Trp—L—Leu—Gly—L—Arg—L—Glx—L—Asp—Gly—L—Leu—L—Leu—$NH_2$ | <10 |
| 47. | H—L—Met—L—Trp—L—Leu—Gly—L—Arg—L—Glx—L—Asp—OH | <10 |
| 48. | H—L—Trp—L—Leu—Gly—L—Arg—Gly—L—Asp—Gly—L—Ser—L—Glu—OH | <10 |
| 49. | H—L—Trp—L—Leu—Gly—L—Leu—L—Glx—L—Asp—Gly—L—Ser—L—Glu—OH | 10 |
| 50. | H—L—Trp—L—Val—L—Arg—L—Glx—L—Asp—Gly—L—Ser—L—Glu—OH | <10 |
| 51. | H—L—Leu—Gly—L—Arg—L—Glx—L—Asp—Gly—L—Ser—L—Glu—OH | <10 |
| 52. | H—L—Trp—Gly—Gly—Arg—L—Glx—L—Asp—Gly—L—Ser—L—Glu—OH | <10 |
| 53. | H—L—Trp—L—Leu—Gly—L—Arg—Gly—L—Asp—L—Ser—OH | |
| 54. | H—L—Trp—L—Arg—Gly—L—Asp—L—Ser—OH | |
| 55. | H—L—Arg—L—Leu—Gly—L—Arg—L—Glx—L—Asp—Gly—OH | |
| 56. | H—L—Arg—L—Leu—Gly—L—Arg—L—Glx—L—Asp—Gly—$NH_2$ | |
| 57. | H—L—Arg—L—Leu—Gly—L—Arg—L—Glx—L—Asp—L—Lys—OH | |
| 58. | H—L—Arg—L—Leu—Gly—L—Arg—L—Glx—L—Asp—OH | |
| 59. | H—L—Arg—L—Leu—Gly—L—Arg—L—Glx—L—Asp—$NH_2$ | |
| 60. | H—L—Arg—L—Leu—Gly—L—Arg—L—Glx—OH | |

In the table, Glx indicates Glu or Gln.

EFFECTS OF THE INVENTION

The novel peptide of the present invention has a high macrophage chemotactic activity and is thus useful as the reagent for study of delayed-type hypersensitivity and further expected to be effectively used for medical application as an antitumor agent.

We claim:

1. A peptide having the following amino acid sequence:

H-Trp-Leu-Gly-Arg-X-Asp-Gly-Ser-Glu-OH or

H-Arg-Leu-Gly-Arg-X-Asp-Gly-Ser-Glu-OH wherein X represents Glu or Gln, and a salt thereof.

2. A peptide represented by formula:

m-A-B-C-D-E-F-G-H-I-n wherein m is:

(a) hydrogen, (b) H-Lys, (c) Fmoc or (d) L-Met;

A is:

(a) absent, (b) L-Trp, (c) L-Phe, (d) D-Trp, (e) L-Arg or (f) L-Lys;

B is:

(a) absent, (b) L-Leu, (c) L-Ala, (d) L-Pro, (e) D-Leu, (f) L-Ile, (g) D-Nle, (h) Gly or (i) L-Val;

C is:

(a) absent, (b) Gly or (c) L-Ile;

D is:

(a) absent, (b) L-Arg,
(c) L-Lys,
(d) D-Arg,
(e) L-Tyr,
(f) L-Asp,
(g) L-His or
(h) L-Gln;

E is:
(a) absent,
(b) L-Glu,
(c) L-Gln,
(d) D-Glu,
(e) Gly or
(f) L-Arg;

F is:
(a) absent,
(b) L-Asp,
(c) L-Asn,
(d) L-Glu,
(e) D-Asp or
(f) L-Ser;

G is:
(a) absent,
(b) Gly or
(c) L-Lys;

H is:
(a) absent,
(b) L-Ser,
(c) L-Cys,
(d) L-Ala,
(e) D-Ser or
(f) L-Leu;

I is:
(a) absent,
(b) L-Glu,
(c) L-Asp,
(d) L-Glu or
(e) L-Leu;

n is:
(a) hydroxy or
(b) amino group.

* * * * *